(12) United States Patent
Conner et al.

(10) Patent No.: US 7,256,324 B2
(45) Date of Patent: Aug. 14, 2007

(54) PLANT REGULATORY SEQUENCES FOR SELECTIVE CONTROL OF GENE EXPRESSION

(75) Inventors: Timothy W. Conner, Wildwood, MO (US); Patrice Dubois, Richmond Heights, MO (US); Marianne Malven, Ellisville, MO (US); James D. Masucci, Manchester, MO (US)

(73) Assignee: Monsanto Technology LLC, St. Louis, MO (US)

( * ) Notice: Subject to any disclaimer, the term of this patent is extended or adjusted under 35 U.S.C. 154(b) by 267 days.

(21) Appl. No.: 10/660,208

(22) Filed: Sep. 11, 2003

(65) Prior Publication Data

US 2004/0133946 A1    Jul. 8, 2004

Related U.S. Application Data

(62) Division of application No. 09/846,903, filed on May 1, 2001, now abandoned.

(60) Provisional application No. 60/201,255, filed on May 1, 2000.

(51) Int. Cl.
*C12N 15/82* (2006.01)
*A01H 5/00* (2006.01)

(52) U.S. Cl. .................. 800/287; 800/298; 536/24.1; 435/252.3; 435/419; 435/468; 435/91.41

(58) Field of Classification Search ............ 536/24.1
See application file for complete search history.

(56) References Cited

U.S. PATENT DOCUMENTS 5,589,610 A    12/1996    De Beuckeleer et al. ... 800/303

FOREIGN PATENT DOCUMENTS

| WO | WO90/08825 | 8/1990 |
|----|------------|--------|
| WO | WO96/40925 | 12/1996 |
| WO | WO97/44448 | 11/1997 |
| WO | WO99/43797 | 9/1999 |

OTHER PUBLICATIONS

Kim Y.et al. A 20 nucleotide upstream element is essential for the nopaline synthase (nos) promoter activity. Plant Mol Biol. Jan. 1994;24(1):105-17.*

Eyal Y. et al. Pollen specificity elements reside in 30 bp of the proximal promoters of two pollen-expressed genes. Plant Cell. Mar. 1995;7(3):373-84.*

Tacke E. et al. GenBank Accession No. X88779, Z.mays Glossy2 locus DNA, May 9, 1996.*

Ainley M. et al. Geneseq Accession Nos. AAV63717 and, AAV63730, Apr. 12, 1999.*

Ainley et al., GenBank Accession No. AAV63717, and, AAV63730, Apr. 12, 1999.

Custers et al., "Analysis of micro-specific promoters in transgenic tobacco," *Plant Mol. Biol.*, 35:689-699, 1997.

Eyal et al., "Pollen specificity elements reside in 30 bp of the proximal promoters of two pollen-expressed genes," *Plant Cell*, 7(3):373-384, 1995.

Hamilton et al., "A monocot pollen-specific promoter contains separable pollen-specific and quantitative elements," *Plant Mol. Biol.*, 38:663-669, 1998.

Kim et al., "A 20 nucleotide upstream element is essential for the nopaline synthase (nos) promoter activity," *Plant Mol. Biol.*, 24(1):105-117, 1994.

Tacke et al., GenBank Accession No. X88779, zmays Glossy2 locus DNA, May 9, 1996.

Terada et al., "A type I element composed of the hexamer (ACGTCA) and octamer (CGCGGATC) motifs plays a role(s) in meristematic expression of a wheat histone H3 gene in transgenic rice plants," *Plant Molecular Biology*, 24:17-26, 1995.

Tsuchiya et al., "Molecular characterization of rice genes specifically expressed in the anther tapetum," *Plant Mol. Biol.*, 26:1737-1746, 1994.

Twell et al., "Promoter analysis of genes that are coordinately expressed during pollen development reveals pollen-specific enhancer sequences and shared regulatory elements," *Genes & Development*, 5:496-507, 1991.

Walbot, EMBL Accession No. AW562753, Mar. 15, 2000.

Walbot, EMBL Accession No. AW566088 Mar. 10, 2000.

Zabaleta et al., "Promoters of nuclear-encoded respiratory chain complex I genes from *Arabidopsis thaliana* contain a region essential for anther/pollen-specific expression," *The Plant Journal*, 15:49-59, 1998.

* cited by examiner

*Primary Examiner*—Cynthia Collins
(74) *Attorney, Agent, or Firm*—Fulbright & Jaworski L.L.P.

(57) ABSTRACT

Promoters from male reproductive tissues were isolated from corn (*Zea mays*). These promoters can be used in plants to regulate transcription of target genes including genes for control of fertility, insect or pathogen tolerance, herbicide tolerance or any gene of interest.

9 Claims, 2 Drawing Sheets

SEQUENCE LISTING

```
<160> NUMBER OF SEQ ID NOS: 98

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: adaptor
                        sequence

<400> SEQUENCE: 1
gtaatacgac tcactatagg gc                                          22

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: adaptor
                        sequence

<400> SEQUENCE: 2
actatagggc acgcgtggt                                              19

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: adaptor
                        sequence

<400> SEQUENCE: 3
agggcaagct tggtcgacgg cccgggctgg                                  30

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: fully
                        synthesized primer

<400> SEQUENCE: 4
ctgacggagg cgctacg                                                17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: fully
                        synthesized primer

<400> SEQUENCE: 5
gttgaagtcg atgcagc                                                17

<210> SEQ ID NO 6
<211> LENGTH: 17
```

```
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 6
cgtcgggtat agattta                                                17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 7
ccatgactca cttcctg                                                17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 8
cgaatctgct acggatc                                                17

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 9
acacggtatc tctgagc                                                17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 10
cacacgtaat cgtaatg                                                17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 11
ccatgcacca gctgcag                                                17

<210> SEQ ID NO 12
<211> LENGTH: 17
<212> TYPE: DNA
```

```
<213> ORGANISM: Artificial Sequence
<220> FEATURE:
<223> OTHER INFORMATION: Description of Artificial Sequence: fully
      synthesized primer

<400> SEQUENCE: 12
cgaatctgct acggatc                                                   17

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 13
atgcgcagac gttgagg                                                   17

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 14 ggacccagc gtccgtagcg cctc                                            24

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 15
ggatcccagc tccgacagcg agatcttacc gtc                                 33

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 16
ggatccagat ctgtccgccg tctccgacat tagcg                               35

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 17
ggatccagat ctagcgaatc tgctacggat caata                               35

<210> SEQ ID NO 18
<211> LENGTH: 17
<212> TYPE: DNA
<213> ORGANISM: Artificial Sequence
```

```
<220> FEATURE:
<223> OTHER INFORMATION: Description of Artificial Sequence: fully
      synthesized primer

<400> SEQUENCE: 18
ggacatcacc atccagc                                                    17

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 19
catcgagcgt gccggag                                                    17

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 20
ggatgccatc gaagctggat ggtgatg                                         27

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 21
ggatccagat ctaagtagag agggcccacc aggtagtc                             38

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 22
ggatccagat ctcccctttg ctagttctct cctcgcc                              37

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 23
acgacctgga caagtac                                                    17

<210> SEQ ID NO 24
<211> LENGTH: 17
<212> TYPE: DNA
<213> ORGANISM: Artificial Sequence
<220> FEATURE:
```

```
<223> OTHER INFORMATION: Description of Artificial Sequence: fully
      synthesized primer

<400> SEQUENCE: 24
tcgccttcac gttgtcg                                                    17

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 25
cagctcgccg tgtacttgtc caggtcg                                         27

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 26
ggatccagat ctaggttgcc atccagctgg atggcgatg                            39

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 27
cacccggaga gcgttgtgtg cggaagc                                         27

<210> SEQ ID NO 28
<211> LENGTH: 37
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 28
ggatccagat ctccttcctg tggccgccgg ctctcct                              37

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 29
gtggcatcat cgtcagc                                                    17

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: fully
```

-continued

```
                       synthesized primer

<400> SEQUENCE: 30
cctcgcacag cgtcgagcag                                              20

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: fully
                       synthesized primer

<400> SEQUENCE: 31
ctgccctcgc acagcgtcga gcagaag                                      27

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: fully
                       synthesized primer

<400> SEQUENCE: 32
ggatccagat cttcggcgat tgttgatgga tcggagaag                         39

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: fully
                       synthesized primer

<400> SEQUENCE: 33
ccatggccaa gaagggt                                                 17

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: fully
                       synthesized primer

<400> SEQUENCE: 34
cccttctcct tgatgtccac c                                            21

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: fully
                       synthesized primer

<400> SEQUENCE: 35
ccttcttggc catggcgccg aacgcc                                       26

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence: fully
                       synthesized primer
```

```
<400> SEQUENCE: 36
ggatccagat ctcgaagtgg tacgccgcga taggctcat                                39

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 37
ggatccagat ctcatgtccg tagatgtgca ccac                                     34

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 38
gccggcgaga gcatggcgat g                                                   21

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 39
cgttgctgtg gtctgcttg                                                      19

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 40
gccgacacca gggtgacctc caggacac                                            28

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 41
ggatccagat ctcatgctct cgccggcgaa ggtgttttgc                               40

<210> SEQ ID NO 42
<211> LENGTH: 34
<212> TYPE: DNA
<213> ORGANISM: Artificial Sequence
<220> FEATURE:
<223> OTHER INFORMATION: Description of Artificial Sequence: fully
      synthesized primer
```

<400> SEQUENCE: 42
ggatccagat ctctcgccgg cgaaggtgtt ttgc                               34

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 43
ctacgactag ctagattcc                                                19

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 44
gcggattctg ttcttgcc                                                 18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 45
gcggattctg ttcttccc                                                 18

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 46
acgcggatcc tggtgggcgc catcgcg                                       27

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 47
ggatccagat cttgggcgcc atcgcgcgtg gaatctagc                          39

<210> SEQ ID NO 48
<211> LENGTH: 32
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 48
ggatccagat ctcgtttgcg gtgttcgcgt tg                32

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: fully
                        synthesized primer

<400> SEQUENCE: 49
ccgctttagt tcagt                                    15

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: fully
                        synthesized primer

<400> SEQUENCE: 50
cccgcatttc atttc                                    15

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: fully
                        synthesized primer

<400> SEQUENCE: 51
gtctgttgtc catgcgattc acgctac                       27

<210> SEQ ID NO 52
<211> LENGTH: 43
<212> TYPE: DNA
<213> ORGANISM: Artificial Sequence
<220> FEATURE:
<223> OTHER INFORMATION: Description of Artificial Sequence: fully
                        synthesized primer

<400> SEQUENCE: 52
ggatccagat ctcatgcgat tcacgctaca gccaaatgat cga     43

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: fully
                        synthesized primer

<400> SEQUENCE: 53
ggatccagat ctgcccggtc agacatgttt ac                 32

<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence: fully
                        synthesized primer

<400> SEQUENCE: 54

```
ggatccagat ctgctcggcg cgttggtcgg tcg                          33
```

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 55

```
atgagggttc ttgtagag                                           18
```

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 56

```
cccatcagtc cgctgttg                                           18
```

<210> SEQ ID NO 57
<211> LENGTH: 40
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 57

```
ggatcctaga tctaaacaca gagactaaca gcttctctac                   40
```

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 58

```
tgccgtgtga tcatattcta gagacac                                 27
```

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 59

```
aaacacagag actaacagct tctctac                                 27
```

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 60

```
attctccagc gcaggtag                                           18
```

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: fully
        synthesized primer

<400> SEQUENCE: 61
tgccctggct cgtcgaag                                              18

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: fully
        synthesized primer

<400> SEQUENCE: 62
cctgccacga catctttgcc cggtcag                                    27

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: fully
        synthesized primer

<400> SEQUENCE: 63
tcgcacatca ggtgctcgtc cacgtac                                    27

<210> SEQ ID NO 64
<211> LENGTH: 38
<212> TYPE: DNA
<213> ORGANISM: Artificial Sequence
<220> FEATURE:
<223> OTHER INFORMATION: Description of Artificial Sequence: fully
        synthesized primer

<400> SEQUENCE: 64
ggatcctaga tctctgcgct ggagaatgga tcggagag                        38

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: fully
        synthesized primer

<400> SEQUENCE: 65
gaatcatcgg aataatggc                                             19

<210> SEQ ID NO 66
<211> LENGTH: 16
<212> TYPE: DNA
<213> ORGANISM: Artificial Sequence
<220> FEATURE:
<223> OTHER INFORMATION: Description of Artificial Sequence: fully
        synthesized primer

<400> SEQUENCE: 66
taggagcggg agcatc                                                16

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 67
catcggcgga tgccatggac ctaccct                                        27

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 68
gccaggagga gcacgacgag gaacacg                                        27

<210> SEQ ID NO 69
<211> LENGTH: 40
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 69
ggatcctaga tctgccagga ggagcacgac gaggaacacg                          40

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 70
caaacgctgc tgcgctctc                                                 19

<210> SEQ ID NO 71
<211> LENGTH: 16
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 71
gagcgtggcg acgacg                                                    16

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 72
gcgccatttt ctccaggttg ttctctc                                        27

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 73
caccgatcaa aacgacaggc tcctctg                                27

<210> SEQ ID NO 74
<211> LENGTH: 40
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 74
ggatcctaga tctcaccgat caaaacgaca ggctcctctg                  40

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 75
caaggaggtg ttccacagcg tggcc                                  25

<210> SEQ ID NO 76
<211> LENGTH: 25
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 76
tggcgttgcg cacgacggag tgcat                                  25

<210> SEQ ID NO 77
<211> LENGTH: 27
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 77
accgtgaagt tgtcgccggc cttcttg                                27

<210> SEQ ID NO 78
<211> LENGTH: 40
<212> TYPE: DNA
<213> ORGANISM: Artificial Sequence
<220> FEATURE:
<223> OTHER INFORMATION: Description of Artificial Sequence: fully
      synthesized primer

<400> SEQUENCE: 78
ggatcctaga tctacgagga tcgccgatag gccacctagg                  40

<210> SEQ ID NO 79

-continued

```
<211> LENGTH: 2213
<212> TYPE: DNA
<213> ORGANISM: Zea mays

<400> SEQUENCE: 79
cctgtccttc ggcatttctg tagctactct cgacgatgag gtcttcgtcg cctcatcggt        60
aggcaaagtg tcctattgca cctctaagga ggtaggacta atcaactccc tagtgacacc       120
tatgtaggcc atctgagcag aggcaatgat ctttcactaa gactgattca gccaaagtta       180
actcttgaag tgctcctaaa caaataactt tggagcaaag tgaattttgg caattgttag       240
gtgaaggcag taaatgtgat ctgccctcac ctcctcagcc acttttatac tgaaaatgca       300
catgacgcga cacgggtcat ggaaattgtt cccgcgcagc gtcccaagtc cccctcgat       360 gatttaactt ctaggtcaac cgtttttact tcaaatgtat caccttcttc ttaaacaagc       420
tttaggaagt tgttttttcgg atctttggaa ttgggcctcc aagttataat ttttgcaatc      480
taagctcttt gcaaagaaaa caaactcata tcgcaatggg ctacttttgg ggaccttcta       540
tgttgaagat cacttgctta aacttttact ttgacacaag ctagtgtgtt tcaggaatat       600
ctctactgat gcacgaagcc aaccttcggt cgggaaggcg tgcagagaag cattgcacat       660
gaaaggtgaa agggtattaa ccaaagttga tagcttcgat gacagcaaag gagcttcaga       720
tacaagccaa aggaaaaggc gacgaaggcc taaatccgag cagccgaaga tggggaaaat       780
acgctactgc cctaacaaca tttgtaaaca gtgagggta caattgtaat tatgtactaa        840
gtcggttcgt ctcccctata aatagatgaa cagtaacccg cataaattac attttgccag       900
gtgctacagc tttgtatagc tcaggctcca aaacacattc gtgctatctt gcactaagaa       960
gtcaatggta tgattgtaaa cttgttttct ataagagaaa tgaaattcta aggcacatga      1020
gatgagttct catatcttcg tcatgttttt atgtattcta gtcgattaca tccaaccttc      1080
gtccttgagt agttatccca aagacttaac acttcaagga tgaaggcttc tactttttaa      1140
cattgtgttg tcttgttttt tatttcattt agcaattaaa agcaagtgac taacacatgg      1200
ttaaacccaa gatccgaaaa gaggctaaaa ttgagcaaga atgaacaaaa gttggtaaga      1260
ggaacataaa ccaaccttc ttagcaacat tcttccaaaa aaagaagatc aaaacatgta       1320
cccttgtatt ttgtgaaaac tggatctcca aaattgccta caatggaagg tggctacgag      1380
aaacggttat aatcgaggag gtagagagaa ttttatgcta caaccttcac aggcggtttc      1440
cctaagaaac atccactcta aatgtctttg cacatacggt tcacttaaaa aaccgcaaat      1500
gcaaattgtt cattttcact ggaggttttt taagcgaacc gctagaggaa atctcatttg      1560
caccggcgat ccttaagaca tatcatgagc gaggttgcct tggaagccgg aagagttggt      1620
caatgaccta taaaaagcag aggacacagg agtgccctat tcaagcattg cctaaaaata      1680
gcaaaggcca aacgaccatt tcgtgtacat agcaaacggt gctcctctct ctcaagaaag      1740
gatatcttcg ggaacatcca tccatcccca atccccaaag gcgaggagag aactagcaaa      1800
ggggaaatgg ctgcttccac aaacaacact ctcagggtgc tgttcaccct aatggttgta      1860
tgcgccgcag tatgcacagc gaaaggact gtagcaaagg caggagactt ggcgccagcc       1920
cctgctccgt taggagcagg aggcgccacc gcagcccag aagtgcggc tagagccagc        1980 aggacgttcg acatatcgaa gttcggcgcg accagcgacg gcaagacgga ctcgacacag      2040
gttgcattgc attgcattgc attgcattgc atgttggcac ggtggtgtga ctgatgcact      2100
ggttcaatga tctatcaggc agtccaggac acgtggacgt cagcgtgcgg agcgatggga      2160
gacgcaacga tgctcatccc caagggcgac tacctggtgg gccctctcta ctt            2213
```

<210> SEQ ID NO 80
<211> LENGTH: 809
<212> TYPE: DNA
<213> ORGANISM: Zea mays

<400> SEQUENCE: 80

```
aaaaaaccca cggggttcacg ggtttgggta ctataggaac aaacccgtac caataaaccc      60
gtcgggtata gatttatgcc cattaacaaa cccatggata tgaaaattga tccaaacccg     120
taccctaata gggtaaaaac ccatcgggtt tcgggtttcg agtacccatt gtcatcttta     180
acaggaagtg agtcatgggc ctcttgtgcg tttgcgcttc tcgcttcatg gtccgtgact     240
ttccacgggt acacatatgg gccctaccat ggctctctta tcaactgggc ctcgaagcct     300
agctagttga tggcttgcat aattgcattg catggtctcc tctgctccgt ccgactgagc     360
gattcttccg gtaggggagc tgcagtgcag ctggtgcatg gcgatggatg gctgcgagtg     420
gtccaagaat ttctccccgg catgtcctct cctccagacc tccaccgatg cagcaggctc     480
ctggtagagc taactaaatc ggggacccct tctcaagttt tcatcactat atatgcagca     540
gataccctaga agagcacgac cgagctagga aagcgcgaa cgccgtgcatg cgcagacgtt     600
gaggtcgagg gacacggtat ctctgagctt catcggagag cgacccgcca ccgccacgct     660
tggccgcaag ccgagaagag tgccgggccg ggagaccgga cgattattga tccgtagcag     720
attcgctaat ggcggatacg gcggacatgg agcggatctt caagcggttc gacaccaacg     780
gcgacggtaa gatctcgctg tcggagctg                                       809
```

<210> SEQ ID NO 81
<211> LENGTH: 910
<212> TYPE: DNA
<213> ORGANISM: Zea mays

<400> SEQUENCE: 81

```
ccgtgactttt ccacgggtac acatatgggc cctaccatgg ctctcttatc aactgggcct     60
cgaagcctag ttagttgatg gcttgcataa ttgcattgca taattgcgct tctccctacc    120
atgtgcctgt ttgtttcggc ttctgacagc ttctggccac caaaagctgc tgcggactgc    180
caaacgctct gcttttcagt cagcttctat aaaattcgtt ggggcaaaaa ccatccaaaa    240
tcaatataaa cacataatcg gttgagtcgt tgtaatagtt ggaatccgtc actttctaga    300
tattgaaccc tatgaacaac tttatcttcc tccacacgta atcgtaatga tactcagatt    360
cttttccacag ccaaattccc ccacagccaa attttcagaa aagctggtca gaaaaaagct    420
gaaccaaaca ggcccatggt ctcctctgct ccgtccggct gagcgattct tccggtggga    480
gagctgcagc tgttgcatgg cgatggatgg cagcgaggtg gtccaagaat ttctccccgg    540
catgtcctct cctccagacc tccaccgatg cagcaggctc ctggtagagc taactaaatc    600
ggggacccct tctcaagttt tcatcactat atatgcagca gataccctaga agagcacgac    660
cgagctagga aagcgcgaa cgccgtgcat gcgcagacgt tgaggtcgag ggacacggta    720
tctctgagct tcatcggaga gcgacccgcc accgccacgc ttggccgcaa gccgagaaga    780
gtgccgggcc gggagaccgg acgattattg atccgtagca gattcgctaa tggcggagac    840
ggcggacatg gagcggatct tcaagcggtt cgacaccaac ggcgacggta agatctcgct    900
gtcggagctg                                                           910
```

<210> SEQ ID NO 82

```
<211> LENGTH: 1511
<212> TYPE: DNA
<213> ORGANISM: Zea mays

<400> SEQUENCE: 82
atcgtgtaag gtgatttagt tcatttgttg tgagggaagt gtggtgcttg gtggtctgtt      60
ccacgtggtt cctttgctcg agttttcatg ttctcatcat tcttgccttt gtttgagagg     120
cgaggttatt gtcttctcca ctggagctgg gcagattttg ggttgaacca tcgcgatgta     180
gctagtgaac ctgtggtctt ttgacattaa ttaaggtagt gttcggttct ggagccagtt     240
gggatggagt ggctccgttc gagagatttt ggggagttgg atggctcggt atttgaatat     300
aatttccctt tttagaacca ctctatcttg taaaggattg gcactcaggg ttttcttagc     360
tcaaccgtca gtggaaatcg atttctgctc atggttgtct taactgaacc gccaatgaaa     420
aacgattttc actagcggtt atcgtttacc tgcctatgaa ataattatt tctactggtc      480 tctaacgctg gaggttctga aaaacgccag tgcaaataag tttcgaacca tctctataaa     540
acttctttct actagtgaca tggaaccaat ccgaacaaca ttaaattgag agtgaagtgg     600
cttgatccaa ctatagtcca gaaatcaaac actgcctaga aggctgctgg gcacgaggac     660
ttgaactcta aaaagatgt ggtgctggtg ctcttcaaaa tatttgattg ttgttcagca      720
ttttgttttt gttttgtag gcgtagttcg atttacccat ttatatgatt cgctgtgata     780
caatatcata tgtaattaaa atcaactgac cccccgtttg gatcattgga attgaattcc     840
attctaataa tagtaattta gatatatatc aattaagcta attcagtttt ttgcaaaata     900
tatttgtata ttattattag caagatgtta gaaatattta tgtgctatat ttttactata    960
gaggggtgag acgaagagtg tcttgtaagt tacagagtag aaacaaattc tactaatgca    1020
taaaatcatt tctcatcctg cacccccatga atttgaaccc catgaatttg agataggctt    1080
atatctgaac tttgaaaagt ggtggaatgt caaatttcaa attaaataag ttaatttatt    1140
aggtgaattc caattccttt gaaacaaagg gatctaaacg tcccgtgaga aaatttgcat    1200
gtgcacaaaa gttcacaatt tgcatgctga cacacgcatc tctgggtccg tacgattggt    1260
aaaacttgat gaggttgcct ttgtctagca tccgcatcaa taggaccttt gaaacggtaa    1320
gagttggtca tcgagaacct gaaaaaaaac tagaggacag gagttctttta ttcaagcatg    1380 gcctcaaaat agcaaagtcc agacggtcat ttcgtgtaaa tagcagacgg tgctcctctg    1440
tctcttgcaa tcttccggaa catccatcga tctccccca gcggcgagga gagccggcgg    1500
ccacaggaag g                                                         1511

<210> SEQ ID NO 83
<211> LENGTH: 459
<212> TYPE: DNA
<213> ORGANISM: Zea mays

<400> SEQUENCE: 83
cgtatctagc gactacatgc tacaacatgc tcgatgtcat atacacctat acatgtcact       60
atggcgtatc atactttgtc attaaaatcc acatctaaga catgatccat gtacaactac      120
gataagatag gagtactagt taaatctctg ttgggcattg gaccagatca tgctcgtgct      180
gggctttcgg gcctcgtgtt ctctcaccaa ttatagtggg tagctagtaa atgcatgcat      240
ctatatatgg acatgtatgc atgctattag agtattagtt agaagcgtac cactgcacga      300
agagagaggt acgatcggga gggaaactct catggcccata cacctatcat ctccttttcg      360
tgacatccta ctgtgtatat ataaccaaca acgatcatgt tagttccaca agcaaattaa      420
```

<210> SEQ ID NO 84
<211> LENGTH: 1503
<212> TYPE: DNA
<213> ORGANISM: Zea mays

<400> SEQUENCE: 84

| | | |
|---|---|---|
| atcctccaag gtatcagcag tgggtccgga cccccatggg aaagtgctgg acccctgttt | 60 |
| atatggaccg gacctccagg taaggtccag gacctcacg ggcgcgaact gaacccttg | 120 |
| gatgggtccc ggacccctct gtgtgggatc cgggccactc acaacaaggt cccgggattc | 180 |
| tgggacaaag aataccttgga ccttgttgaa gaccaagcga gggtccggag ccgacacgtg | 240 |
| ttcgggccat gcggtgtacg cttctgctct ccactcaggt ggagacccga tgctgccacg | 300 |
| tggcccacca ccgtgacgta agccagcggg cgaagcctga cgtaaggcct ctgggccaca | 360 |
| cggcctctgc atttattaca gataagccgc atcgcgtgtc cactccactg gcaggcgatg | 420 |
| tgccgcctca gaatttaatg agccttgtcc actccactgg caggcgatgt gccgcctcag | 480 |
| catttaatgt gccctgtcca ctctgctgac aggcaacgac cagccatcct gcaggcggcg | 540 |
| tgcctgtcca ttccgttggc aagcagtacg cctatgctgc ggcatacact gtgctcatca | 600 |
| tcactcgcgt gttaccaagg aggcagcatg ggataccaat actatatgca ctacagacat | 660 |
| tatagcgctc ggggttcacc ctggcgttac gggcattagt tgcttccttc catttgtccc | 720 |
| tcggcccaca tgtcggggct cagcacccttt gtacgtgccc cccttgagct ataaaaggga | 780 |
| gggcacacga cgttacaagg aagacccaac ttaggctcac acactcactc aaactcacaa | 840 |
| gttcatacaa gctctcaagc tcaatacatc acacagtgga gtagggtatt acgctctggc | 900 |
| ggcccgaacc actctaaacc cttgtgtgtt cttgtgttct tcccgattcc atctagcagg | 960 |
| caaaacgctt gggcccctcc tcatcttagg atttagggcg ggtgcgttcc gccacccgac | 1020 |
| cggagaattc cctctccgac agtactcatg accacaaatt cagaccctgt ttgctagctc | 1080 |
| attcatcgta gcatagttcc attcactcat cgaagacaaa acatggttgc gattgtgagc | 1140 |
| accatgtggt cgtcgatgca ggcgcatgtg gcgatggtcg tggcattggc gttcctagtg | 1200 |
| agcggtgact ggtgcggtcc tcccaaggtt cccctggca agaacatcac ggccacctac | 1260 |
| ggcagcgact ggctggacgc taaagcgaca tggtatggca agccaacggg tgctggcccc | 1320 |
| gacgacaacg gtggcggctg cgggtacaag gacgtgaaca gcccccctt caatagcatg | 1380 |
| ggcgcgtgca gcaacatccc tatcttcaag gatggtctgg gatgtgggtc ctgcttcgag | 1440 |
| atcaagtgtg ataagcctgc ggagtgctct ggcaagcccg cggtggtgta catcacggac | 1500 |
| atg | 1503 |

<210> SEQ ID NO 85
<211> LENGTH: 658
<212> TYPE: DNA
<213> ORGANISM: Zea mays

<400> SEQUENCE: 85

| | | |
|---|---|---|
| aaattaatac aaataaaatc atataagtca ctccttctct aaatttatcg tatatacaaa | 60 |
| attattttga ttgttattga aaattaatat acaattatat gatgcaagtt tctttaatta | 120 |
| gcttattatc tatactatat aaaaatcagt atacacatgt tttatatatc atatggtact | 180 |
| tttttcatat tatagtattg atgaattttt cgcccctcta tgtcatactc ctggcttcac | 240 |

```
cctagtctac tacgtcaatt tttttcagta aatgcatcgc aaaatgattt tgcattttg    300 gtgtcctaaa tcttaatata tattcttaga caaatagagt taaacagatg ttaaacatag    360
atttgactta agataaaaat agattttaga aaatacagaa cagccccagt attctgcatt    420
gctaaaaaac actccgtgaa acaatgtgga ccgcaaaaag ttccttcaaa atcctgccat    480
ctgatgctat ttttggggcc aaactccatc accaaccaaa cacaacctct tggctttatt    540
taacttgtgc cttgcggatg ttttcgttgt cgagggaata cgaacgtcgt acgagaacct    600
ttctccctcc tccaccttc tccttttctt gccacggcaa acaccttcg ccggcgag      658
```

<210> SEQ ID NO 86
<211> LENGTH: 1173
<212> TYPE: DNA
<213> ORGANISM: Zea mays

<400> SEQUENCE: 86

```
gtcgtcaacc cggtgactgc catgggcccc atgattccgc ccaccatcaa ctgcagcatg     60
accgtgctcc tacgcctgct acaaggtgcg tggagtagtc gttgctttcc tgcttgctgc    120
tcgatatgca tgccgttcgc gttgccatgc gaatgagacg aagaagaaac taaggagga    180 tgccggcctg ttcgtggtcg caggttgcac ggaggagtac agggacatct ggatggggc    240 ggtgcatgtg cacgacgccg ccatggcgca tatcctggtg ttcgagagcc ggcggcgtc    300 cgggaggcac atctgcgccc agtccatctc ccactggagc gacttcgcgg ccaaggtcgc    360
cgagctgtac cctgagtaca aggtgcccaa gtaagcgacc cgaccatgtt ctgtgaaaat    420
gaaaacctgg atagatagag cattgcttag cttatagttg cgtacgttgc aggttcccca    480 aggatacca gcctgggctg gtgcgacagg gagccgagga ggggtccaag aagctcgtcg    540
cgttggggct gcacttcagc cctctggaga agatcatcag ggacgctgtg gaggccctca    600
agagcagagg ctacatttcg tagctagccg accgacggca gctatagtgg agtagtatgc    660
ctgtcgaatt tcgattccca agtggcaaat tctgcaaaac gagtccgcca atatgaacaa    720
taaataaaga acgttgtgat aaaataaagc agattttctg ttgcatttgg cccttcaaag    780
catccgtggt ggtaagattt cctatgatct gtcctggtcg gtcgggcctg agcacctttt    840
ttctgtagac ggatgcttta tcacctaggg attgttttat tatattgcta taatgcaaat    900
tggttgatcc aaattaaagc aggatctaaa atggtcgaca ggctaagctt ataatgaaca    960
cagaaataaa tcaaggtgga atgtgtccgc aatcgacgct gcgatttcga atgctaaata   1020
aataaatcgg taacacggac ggacgtagaa gagaagccat tatgcgtggc aggcagcaca   1080
agagctattc aaagccgcgg caacggaggg ctgcaattca caaacccaa aattaggtca   1140 ccccggccac tttcaacgcg aacaccgcaa acg                                1173
```

<210> SEQ ID NO 87
<211> LENGTH: 1587
<212> TYPE: DNA
<213> ORGANISM: Zea mays

<400> SEQUENCE: 87

```
actcttccca tttgcgagga atctccacaa gttggagcct ctcacccta caaagttatg    60 atcacaaaga aagcacaaga gtaaggatgg gagagcaaca cacgcaagac tcaaatccgt   120
agcacaatca cgcacacaag ccaagacttg agctcgaaac acagcacatg gagtttgcaa   180
ctcaaacaga gctcaaatca ctaacacagc gaatcaaatg cgtggagacg gagtctggga   240
gtcttagaat gtttcttgaa agcttggtgt tctgctccat gcgcctaggg gtcccttta   300
```

-continued

```
aacctccaag acagctagga gtcgttggag atcaacatgg aaggctgatc tttccttctg    360
ccgagtggcg caccggacag tccggtgcgc caccgggcag gtcctgtagc ttgtccggtg    420
tgcgatctcc ttccatatcg ggcgcatccg accgttgagc cggcggtctc gttggcgcat    480
cagacactgt acggtgtaca ccggacagtc tggtgtgccc aaccaaccgt tggcccgtcc    540
acgtgtcacc cgcagatttc gctgccgacc gttggccgtg agcgccgttg gctcatcgga    600
cagtcattag gaacgaagca taaacaaaag cgcgtgatgt ggacacacat tagggtattt    660
tgggctaact tgacacactt gagtatttat aagatgtgtc atgggcttga cgactctata    720
ggctagctag cacggcacat aattaggttt gtactttagc gtgccatgct agcctatatg    780
tgtataaggc cattctcaat tgaagtttta ttggagtttc attctcatta aatgttgtgc    840
cacataagca aacaagacga catgtcatac catttaatga agagagatat gagagagttt    900
aatggggaat aaagctctat ttacactatt tcctagacaa atattgatat ggtatccttg    960
gaattcgtat gatgaaatcc tcaattgaag aatggcttaa ctggcaccgc tacgtagggg   1020
ctattcaaga accaacaatg tacagttgtt gcaacgtgaa tggttatttg cttcagatta   1080
aagccaattg tttagactga tgcagctgca attcatagag acaaaaacag tgtagaagcc   1140
gtataagcat taagcaaaca agcgaacatt gcttagctac aaccaatttg ctgggcttcc   1200
atgggcatcg cagaagtatt gtggctgcat attgctgaaa ttatagcgag ggcccaaggc   1260
ccatcacttc acttcgaggt cagcattgta cttttgttaa cgtctcgata aatttgttca   1320
cttaaaatag accagttcaa ttctggttct agtcaacatg cctggatcca cggggggagcg   1380
aggagacgaa tgtgtggccc gccgcagtga ggccaagccg agcccggtcg tccgtccaac   1440
cacccctcg tttatactat atatacacag acgcacgata cccatatcgt ggtgctagaa   1500
gcaactgaaa acagccgagc gatctcctct ccctctccct ctccgatcca ttctccagcg   1560
cagcgaagta aacatgtctg accgggc                                        1587
```

<210> SEQ ID NO 88
<211> LENGTH: 665
<212> TYPE: DNA
<213> ORGANISM: Zea mays

<400> SEQUENCE: 88

```
aaagaaaatt ggatgaaagt tactcgaccc cgtcaattta acagtgacat tgaatttgtc     60
gaggctgttg agatgaagac atgccagatt gagggtattt tactaataag gagattttag    120
gtgtgaatga caaacgcttc agccgaatac ttaaaagact ggctaagaag aacaaagcta    180
atttggtgga ggtttcatcc aacagtgatg aggaaagaac accaactctg gtagaagtag    240
agtatgttgc tgcatcaaag agttttttt ttgtggaaaa cttcagcgtg tagttttatt    300
ggtcagcaat gtttgtttgg cagtagcatg catgagtccg attctctgac catctccatt    360
taccggtgcc ctggttatta tccccccatc acaagagtgg ccaacatgca gccctgaaa    420
cctggcgaag tccaaggggg agcgaggaga cgaacgtgtg ccacggtga ggtggggatc     480
cggtccttca cccctttcaac ttgggattcc ctctctattt agccatccgt ccggtgcacg    540
atgctacaag ctcctcgtca ccagtcagaa aacagtggga tcgagttgtt tcactgcacg    600
agcacatcct ccggcgacca ccggcctccc tctccgtcct ctagcgaccg accaacgcgc    660
cgagc                                                                665
```

<210> SEQ ID NO 89
<211> LENGTH: 833
<212> TYPE: DNA
<213> ORGANISM: Zea mays

<400> SEQUENCE: 89

| | | | | | |
|---|---|---|---|---|---|
| acggaaccta | aatatggatg | tcttacaaca | gctaattaga | tgcgaaaggt | tccagcatgc | 60 |
| ccattcgtta | ccctgtgaac | atgggcagat | ctacgggtat | tatgttctgg | cacaccctac | 120 |
| gtatccggta | tatcttgccg | attatgtttt | aatactatga | ggttgtttgt | ataatcacat | 180 |
| ttcacaaatg | agagctgaga | atttaatccg | tgcaaattag | tttatttaat | tgtttgggaa | 240 |
| tatgttttta | agtaggtgaa | gataacataa | ttaagatatc | gattatgtct | cttagtaagg | 300 |
| tctcagctaa | aaagtcgtat | gaactattag | catgactttt | cattgattta | tattgtaatt | 360 |
| tatgaatatt | tttaacttac | tttacaaatt | taaggattat | tatttatatt | ttgaacttat | 420 |
| cctataattt | aaaatttact | atgtaatttc | atgtaaaaat | ggtttctaat | ttgatcgagt | 480 |
| atatatatga | aaattttaga | tgacttatag | aaaaattcta | gatccgccat | ggctgcaga | 540 |
| gtgtagagga | tgtgcatgca | cagatgcact | tcattgttgt | tatatataca | acaagttttc | 600 |
| atgcaataca | agcctataaa | taaatgtcct | gactaagctt | tcgtccacag | aatttaccac | 660 |
| ttcttccgct | gagtactacc | gattcaacag | aacagataga | ccactcgtta | acactgtaca | 720 |
| cttctaccta | tatattcgct | tctctcctct | tgcaaatcat | attgtcaata | gtaacagtga | 780 |
| gaagaacaca | caaaatgagg | gttcttgtag | agaagctgtt | agtctctgtg | ttt | 833 |

<210> SEQ ID NO 90
<211> LENGTH: 823
<212> TYPE: DNA
<213> ORGANISM: Zea mays

<400> SEQUENCE: 90

| | | | | | |
|---|---|---|---|---|---|
| ctgcacggta | ctccaagtat | aagacacagc | taaaacacaa | cataatgcag | tggtcatgtc | 60 |
| taaaacatgt | gtcttaccat | attcattgta | tcaatcagaa | cattcaataa | attaaagtga | 120 |
| ccaatcagat | agtctcctgt | cccgaatata | gagctaagac | actgtgtctt | cgtcaagata | 180 |
| catgtcttga | gatttttac | attcacccccc | ctagacacac | tctaagcacac | aacttaagac | 240 |
| acccattgta | catgccctaa | ctggcaccgc | tacgtagggg | ctattcaaga | accaaccatg | 300 |
| tacagttgtt | gcaacgtgaa | tggttatttg | cttcagatta | aagctaatta | tttagactga | 360 |
| tgcagctgca | attcatagag | acaaaaacag | tgtagaagcc | gtataagcat | taagcaaaca | 420 |
| agcgaacatt | gcttagctac | aaccaatttg | ctgggcttcc | atgggcatcg | cagaagtatt | 480 |
| gtggctgcat | attgctgaaa | ttatagcgag | ggcccaaggc | ccatcacttc | acttcgaggt | 540 |
| cagcattgta | cttttgttaa | cgtctcgata | aatttgttca | cttaaaatag | accagttcaa | 600 |
| ttctggttct | agtcaacatg | cctggatcca | cgggggagcg | aggagacgaa | tgtgtggccc | 660 |
| gccgcagtga | ggccaagccg | agcccggtcg | tccgtccaac | cacccccctcg | tttatactat | 720 |
| atatacacag | acgcacgata | cccatatcgt | ggtgctagaa | gcaactgaaa | acagccgagc | 780 |
| gatctcctct | ccctctcccct | ctccgatcca | ttctccagcg | cag | | 823 |

<210> SEQ ID NO 91
<211> LENGTH: 1163
<212> TYPE: DNA
<213> ORGANISM: Zea mays

<400> SEQUENCE: 91

-continued

```
actacagccc gagggcgcct gtctacgggc ccctcggcgc agactatctg gttgtcccac        60
cggatagtcc ggtgcacacc agacaattac tgttcactgt ccggtgtgcc atcaggcgtt       120
ggttgactgc cttttcttg gatttcttcg cagtttcttt tgagcttctt ttgttcttga        180
gtcttggact tctatgcttc tttttatatc ttcttttgag gtgttgcatc ctcattgcct       240
tagtccaatc ctcttcgcat cctgtgaact acaaacataa acactagcaa acacattagt       300
ccacaggttg cgttgttcat caaacaccaa aaccttttga gccaaatggc acaggtccat       360
tttcattaca gccacccctcc tcagtcgttg gttgttagtt attttcgacg gctcacgtgt      420
atagccgcca aaatttggca aatttcggca ccacaatgtc caaccatcga aaattagaca       480
atagggaaaa tcacgggccg ccctttcatt tccacggcg aattagggtc accaaaccaa        540
aacaatcgaa aaccaaacca cgagccttaa tttttgtggc cttgaccgcc aaaaattaca      600
tgttttcttc tagtggtagg gggagttata agcaacaact ctaacaattg tagaaaaata      660
acattgggtg accaagatga gtaagagagg aatttaggat gagattaata tgtgtttatt     720
gctatctaaa cttttatacat gaggtttcta ggctcgtcat atgttataga gtcaaaaagt    780
atgacatgtt ttttagtca caacaaagtg tggctttcca cacttttgtg gtttatcttg       840
tttaactaag attagccatg acaattatg agcactcgca tgtttggcca cctatatata      900
gcgagacttg tgcatccaag acttcttccg tgcgagggta gtgcacgacc ataggacaag     960
aggagcttgc attcgcgcgt ctcaaggcaa caatctcccc taaaaatagc cacacaacat     1020
tcatgttgcc tatatataaa catcgtgcct cgcccgtccc atcatcacag tcgaaacaaa     1080
gccacaacac atacaggaaa gcaagcaaga atcatcggaa taatggctcg tgcatgcgtg    1140
ttcctcgtcg tgctcctcct ggc                                            1163

<210> SEQ ID NO 92
<211> LENGTH: 2126
<212> TYPE: DNA
<213> ORGANISM: Zea mays

<400> SEQUENCE: 92
cctccgaaat caccgaccac agagatacac ttgcacgggt gtgcgggcga tcagattttt     60
ggggagcgtc ttcgcgactg ctcgcgtgat cgtccacagc ttgctgttcg tcgccttccc    120
aagttgacgc gtgctgctgt tcttcttccc ggcgaccgtt cgagggactg cactgcgtac    180
atcttcctgc accgacttcg tacggctaca tcgaacaaac acacgagatg tctcgtgtga    240
atggagccac tggtgccttg agcatcggtc cctccgctgg gtacactctg ttcttcgtat     300
ttgtgcatgt tcattgctg tttactgctt atgcgagtag ttatacacat atgcacatac     360
atgtcatcac atatatcgca ctgattatct ggattaaatt aaaactaaaa atgcctaact     420
ttctaacaat atttgcactt gttcttacta ttcctgtttg atttggtttt ttgattgagt     480
gtgatgagtt gtgaagtaat gtctataatt gcatctaaat atatatatat gcataaaaat     540 atagaaaatac tcccataaaa acagatccat cttatcttga agattctat attatcctaa     600 tagatccatc ttgtcctgat aagcatactt attccaccctt agagtaacaa tcatgatcta     660
atccaaatta attagatcta atctaatcta atctaattca atataatcta atttgaccta     720
atttagtcaa aactagtcta atctaatctg aaactcttat cttattgatc tttcttgcct     780
atatctaaag gttagaacta attaacttat ctagtccaac ctaggagcaa acaacaaac      840 atgattctac atattctcat gaagcttaag ccacctatta agccatatgc tctacctact     900
```

```
gagctatttg gtgtacctac aaacccattt taaccataaa tcatttaatt tgcaattagt        960
gaacattgta attgtcctag ttgcctggtt tgttgtatta tatatttgag taacgagtaa       1020
tgacttcata tttggattga gctagtaact taactaattc caacttggat atggatgtat       1080
atatggttgt atccgtgggg gtggcctttg atttggttat atttcacttg agagagtagt       1140
attgtaatgt tctgaagagt tgttcagtat tttctggaac aaagaagata aatacttccg       1200
taaggttgca caacttatca tttgaaaggg gttactatgt ttggttgtga tgcatatagc       1260
tcatgctgaa actaatcatc tttgttgatt agaacggcta ggaggttagc agttgtagaa       1320
gttgcagtaa ttacagaaaa aaaaaggatg gatggaagca atccaatatg tgcatgcaaa       1380
atttgggttt gaacaaggac ttatggtaag agaaacatgc gcttgaacag tatgtgtagg       1440
agactcaaag gagttctgga gagagaggtt tcttctttt tttcttagtt ttgacttccg        1500
gtctataact aacattgtaa gagcaaaaat gagaaaaaaa catgactaaa gttaaaaata       1560
aggacaccag caaaaccaaa ggcaccacct taaaaaactg ttttcttttt ctgaacacag       1620
aatcaagggg atttatttgt tattaatact aacagaaaat gttagcagga gtgacagtct       1680
gttggagcag gattctgcga ggaagccgct tatccataga caggaatttt tttagtgata       1740
agtagggcac actcttaact ttgcatgagg agtttgggta ccaaatacag gtgaggggtg       1800
aggcttcgtc agtcgttgca caggtaaaga ttgatgattt gatgtaactt tgaaccgctc       1860
taactaacta aatcgtcctc gagtgtgcgg cgggtgcgag caacaaggcc gtccgctcct       1920
tgttcgtccc tgcatgtgtt ccgttcggtt ccatcaattc caccacgaaa taaggctgta       1980
taaatctttc ctgggcgttc cctctctctc ctgtgcatcg ccggacggaa ccaaacgcca       2040
aacgctgctg cgctctctcc ttctcgtcct gaccccccag agcgagaggg agggcaccc       2100 agaggagcct gtcgttttga tcggtg                                          2126

<210> SEQ ID NO 93
<211> LENGTH: 2508
<212> TYPE: DNA
<213> ORGANISM: Zea mays

<400> SEQUENCE: 93
actgcttgtg aaaagtaaac tgaattctgg ttgtgaacta cttgtttaag taaatgcgtg         60
tttctgtttt ttgttgtcag tgcatttctg tttttcactga tgaaaccacc atttctgctt       120
tcaatgaatc tattgaactg aactgcaaaa aaagaaattg ttctattttg tttgagtgca       180
caaacggaac tcaacggaac tagatctgaa tatgtttgag tgcacaaaca gaaattgttc       240
tgttctggtt tcagtgaact ccacaaatag aactgaatct attatgtttg agtgtagaaa       300
cagataccga aatgctacat ctagcactta atctggcaga atcagaaaat tggggcaaat       360
acaagttgtt taagagcaca aacagaaact gaatctgttt gattgcagaa accaataaaa       420
acagaaatat atgttgaaaa taattcataa gtaggcagtg gtggtgctat ggtgcatacc       480
aggttcttat tcaaatgatt tgctaaagtc aaatatatgc ttctggtctg attgatttgt       540
gaaactgaaa tggatatttt atttcggcac tatgaaataa actcactgtg atcctgaaac       600
atatcagttg tgtttgtttt tgtaaatctt ttataccact aggggagaaa attagcttag       660
ttcaatcgca tctcatatgt ctaattacca ggggagaaaa ttagcttagt tcattttgtt       720
gctgccatat gggtgaaaaa ataatgagac atctaaatca gtaaattgga aatatagcat       780
cttaaacctg caggtagttt cttaaacctg attctagcta caacttagta caactaccgg       840 tagttttta aacctgattc tagctacatg ttttatattg tggcacaaga acttttaaga       900
```

```
acatatgctg atgcccactg tatttagtta ctacttcaag accaactgta ttttagttac      960
aaatgtgttt tcaagattat agaaatttgt agctgaaatt atccacacca tatttgtgaa     1020
ctgacatcat ttctaagaat attactgatt agaatctttc acttttataa tgctttgcag     1080
gagtggcccc tctggagttg aatatgcagt tataaccaaa ttttaccccct tttatcctag    1140
aagagttgcc aagacacggt ataagaccat gataatagac taagagagga tttggctcta     1200
attactatat gttttattta tgcagtccca tgagaacttt gagtatttgc agattgcttt     1260
attaatttat taaagttaaa gattgtatgt gttgagtatg tatccactct tgttggaagt     1320
gtcttgcaat tccaatccaa ggatgtataa aatactgcat gggctaagta tgtgtttttt     1380
catgtatttg gagtatatat acttttttgtt gcttgagaac atgtatgtac actagaagct    1440
tgtcaattgt gtgaacttga gttgatccct gtctaacctg agtatatata tatatatata    1500
ttttgttgct tgagaacaag tatgtacaat agaggcttga caattgtgtg aacttgagtt    1560
gaacatgaat tttgataatc acaactcacc atccctttca atatgcttag aatatagctt    1620
tttataattt ttcaccctac aatacaaaat tgttctatga aggccatggt acatcatcat    1680
atcctgtatt atcaacctag gatttgtcta tttcgattaa taatggcatt gagtcaaatt    1740
ttggttgttt caaatgatag acttcgatat ttgttatgat ttatgagttg attcttgata    1800
gcattactaa aaaatgacct atgtatatac aagtgtcttc cgttgcaacg cacggacata    1860
tacctagtca atcactaaga ccctaatttt gaagttggga cttagacgtg ttccacgttt    1920
gtaaaggcaa gtatataggt gtatgtatat aagagccggt gtatacaaca attttttata    1980
agaaaacttg aacaagtagc caggtgttga aatcttcata tatgtgccga cgccattcaa    2040
catcatattt ggcttctggc gaggatcgta gtatcaagca acataaaagc aatgacaaac    2100
agcgaagcac aaagatctcc caggctcgtc ataaactaat cacaatgttg tttgtcctcc    2160
acaattagca caacccattt tagaaaaaga tgccacgatc gatcgagacg ttggccagct    2220
atcaaacaga taagaactac ccaaatattt cctaaatcca gaacggaaga cccattgact    2280
aggtccttac ctctcaaata gacagactat tcttctccac atcaaaatat agggactccc    2340
gatgcaacaa acacgggcca ccacacaaca atggtgaaat gaccatgcat gcatccacgt    2400
ccgtacgcag ccatttcgtc tataaatttg cttcccatcc gattcaacta caagcttgcg    2460
ggcaaaaatg gcaaaggctc tcctaggtgg cctatcggcg atcctcgt               2508

<210> SEQ ID NO 94
<211> LENGTH: 1797
<212> TYPE: DNA
<213> ORGANISM: Zea mays

<400> SEQUENCE: 94
aagctttagg aagttgtttt tcggatcttt ggaattgggc ctccaagtta taattttgc       60
aatctaagct ctttgcaaag aaaacaaact catatcgcaa tgggctactt ttggggacct     120
tctatgttga agatcacttg cttaaacttt tactttgaca caagctagtg tgtttcagga    180
atatctctac tgatgcacga agccaacctt cggtcgggaa ggcgtgcaga gaagcattgc    240
acatgaaagg tgaaagggta ttaaccaaag ttgatagctt cgatgacagc aaaggagctt    300
cagatacaag ccaaaggaaa aggcgacgaa ggcctaaatc cgagcagccg aagatgggga    360
aaatacgcta ctgccctaac aacatttgta aacagtgagg ggtacaattg taattatgta    420
ctaagtcggt tcgtctcccc tataaataga tgaacagtaa cccgcataaa ttacattttg    480
```

|  |  |  |  | |
|---|---|---|---|---|
| ccaggtgcta | cagctttgta | tagctcaggc | tccaaaacac attcgtgcta tcttgcacta | 540 |
| agaagtcaat | ggtatgattg | taaacttgtt | ttctataaga gaaatgaaat tctaaggcac | 600 |
| atgagatgag | ttctcatatc | ttcgtcatgt | ttttatgtat tctagtcgat tacatccaac | 660 |
| cttcgtcctt | gagtagttat | cccaaagact | taacacttca aggatgaagg cttctacttt | 720 |
| ttaacattgt | gttgtcttgt | tttttatttc | atttagcaat taaaagcaag tgactaacac | 780 |
| atggttaaac | ccaagatccg | aaaagaggct | aaaattgagc aagaatgaac aaaagttggt | 840 |
| aagaggaaca | taaaccaacc | tttcttagca | acattcttcc aaaaaaagaa gatcaaaaca | 900 |
| tgtacccttg | tattttgtga | aaactggatc | tccaaaattg cctacaatgg aaggtggcta | 960 |
| cgagaaacgg | ttataatcga | ggaggtagag | agaattttat gctacaacct tcacaggcgg | 1020 |
| tttccctaag | aaacatccac | tctaaatgtc | tttgcacata cggttcactt aaaaaaccgc | 1080 |
| aaatgcaaat | tgttcatttt | cactggaggt | tttttaagcg aaccgctaga ggaaatctca | 1140 |
| tttgcaccgg | cgatccttaa | gacatatcat | gagcgaggtt gccttggaag ccggaagagt | 1200 |
| tggtcaatga | cctataaaaa | gcagaggaca | caggagtgcc ctattcaagc attgcctaaa | 1260 |
| aatagcaaag | gccaaacgac | catttcgtgt | acatagcaaa cggtgctcct ctctctcaag | 1320 |
| aaaggatatc | ttcgggaaca | tccatccatc | cccaatcccc aaaggcgagg agagaactag | 1380 |
| caaagggaa | atggctgctt | ccacaaacaa | cactctcagg gtgctgttca ccctaatggt | 1440 |
| tgtatgcgcc | gcagtatgca | cagcgaaaag | gactgtagca aaggcaggag acttggcgcc | 1500 |
| agcccctgct | ccgttaggag | caggaggcgc | caccgcagcc ccagaaggtg cggctagagc | 1560 |
| cagcaggacg | ttcgacatat | cgaagttcgg | cgcgaccagc gacggcaaga cggactcgac | 1620 |
| acaggttgca | ttgcattgca | ttgcattgca | ttgcatgttg gcacggtggt gtgactgatg | 1680 |
| cactggttca | atgatctatc | aggcagtcca | ggacacgtgg acgtcagcgt gcggagcgat | 1740 |
| gggagacgca | acgatgctca | tccccaaggg | cgactacctg gtgggccctc tctactt | 1797 |

<210> SEQ ID NO 95
<211> LENGTH: 828
<212> TYPE: DNA
<213> ORGANISM: Zea mays

<400> SEQUENCE: 95

|  |  |  |  | |
|---|---|---|---|---|
| ccgtgacttt | ccacgggtac | acatatgggc | cctaccatgg ctctcttatc aactgggcct | 60 |
| cgaagcctag | ttagttgatg | gcttgcataa | ttgcattgca taattgcgct tctccctacc | 120 |
| atgtgcctgt | ttgtttcggc | ttctgacagc | ttctggccac caaaagctgc tgcggactgc | 180 |
| caaacgctct | gcttttcagt | cagcttctat | aaaattcgtt ggggcaaaaa ccatccaaaa | 240 |
| tcaatataaa | cacataatcg | gttgagtcgt | tgtaatagtt ggaatccgtc actttctaga | 300 |
| tattgaaccc | tatgaacaac | tttatcttcc | tccacacgta atcgtaatga tactcagatt | 360 |
| cttttccacag | ccaaattccc | ccacagccaa | attttcagaa aagctggtca gaaaaaagct | 420 |
| gaaccaaaca | ggcccatggt | ctcctctgct | ccgtccggct gagcgattct tccggtggga | 480 |
| gagctgcagc | tgttgcatgg | cgatggatgg | cagcgaggtg gtccaagaat ttctccccgg | 540 |
| catgtcctct | cctccagacc | tccaccgatg | cagcaggctc ctggtagagc taactaaatc | 600 |
| ggggacccct | tctcaagttt | tcatcactat | atatgcagca gatacctaga agagcacgac | 660 |
| cgagctagga | gaagcgcgaa | cgccgtgcat | gcgcagacgt tgaggtcgag ggacacggta | 720 |
| tctctgagct | tcatcggaga | gcgacccgcc | accgccacgc ttggccgcaa gccgagaaga | 780 |
| gtgccgggcc | gggagaccgg | acgattattg | atccgtagca gattcgct | 828 |

<210> SEQ ID NO 96
<211> LENGTH: 847
<212> TYPE: DNA
<213> ORGANISM: Zea mays

<400> SEQUENCE: 96

| | | | | | |
|---|---|---|---|---|---|
| ccgtgacttt | ccacgggtac | acatatgggc | cctaccatgg | ctctcttatc | aactgggcct | 60 |
| cgaagcctag | ttagttgatg | gcttgcataa | ttgcattgca | taattgcgct | tctccctacc | 120 |
| atgtgcctgt | ttgtttcggc | ttctgacagc | ttctggccac | caaaagctgc | tgcggactgc | 180 |
| caaacgctct | gcttttcagt | cagcttctat | aaaattcgtt | ggggcaaaaa | ccatccaaaa | 240 |
| tcaatataaa | cacataatcg | gttgagtcgt | tgtaatagtt | ggaatccgtc | actttctaga | 300 |
| tattgaaccc | tatgaacaac | tttatcttcc | tccacacgta | atcgtaatga | tactcagatt | 360 |
| cttt ccacag | ccaaattccc | ccacagccaa | attttcagaa | aagctggtca | gaaaaaagct | 420 |
| gaaccaaaca | ggcccatggt | ctcctctgct | ccgtccggct | gagcgattct | tccggtggga | 480 |
| gagctgcagc | tgttgcatgg | cgatggatgg | cagcgaggtg | gtccaagaat | ttctccccgg | 540 |
| catgtcctct | cctccagacc | tccaccgatg | cagcaggctc | ctggtagagc | taactaaatc | 600 |
| ggggacccct | tctcaagttt | tcatcactat | atatgcagca | gatacctaga | agagcacgac | 660 |
| cgagctagga | gaagcgcgaa | cgccgtgcat | gcgcagacgt | tgaggtcgag | ggacacggta | 720 |
| tctctgagct | tcatcggaga | gcgacccgcc | accgccacgc | ttggccgcaa | gccgagaaga | 780 |
| gtgccgggcc | gggagaccgg | acgattattg | atccgtagca | gattcgctaa | tggcggagac | 840 |
| ggcggac | | | | | | 847 |

<210> SEQ ID NO 97
<211> LENGTH: 727
<212> TYPE: DNA
<213> ORGANISM: Zea mays

<400> SEQUENCE: 97

| | | | | | |
|---|---|---|---|---|---|
| aaaaaaccca | cgggttcacg | ggtttgggta | ctataggaac | aaacccgtac | caataaaccc | 60 |
| gtcgggtata | gatttatgcc | cattaacaaa | cccatggata | tgaaaattga | tccaaacccg | 120 |
| taccctaata | gggtaaaaac | ccatcgggtt | tcgggtttcg | agtacccatt | gtcatcttta | 180 |
| acaggaagtg | agtcatgggc | ctcttgtgcg | tttgcgcttc | tcgcttcatg | gtccgtgact | 240 |
| ttccacgggt | acacatatgg | gccctaccat | ggctctctta | tcaactgggc | ctcgaagcct | 300 |
| agctagttga | tggcttgcat | aattgcattg | catggtctcc | tctgctccgt | ccgactgagc | 360 |
| gattcttccg | gtaggggagc | tgcagtgcag | ctggtgcatg | gcgatggatg | gctgcgagtg | 420 |
| gtccaagaat | ttctccccgg | catgtcctct | cctccagacc | tccaccgatg | cagcaggctc | 480 |
| ctggtagagc | taactaaatc | ggggacccct | tctcaagttt | tcatcactat | atatgcagca | 540 |
| gatacctaga | agagcacgac | cgagctagga | gaagcgcgaa | cgcgtgcatg | cgcagacgtt | 600 |
| gaggtcgagg | gacacggtat | ctctgagctt | catcggagag | cgacccgcca | ccgccacgct | 660 |
| tggccgcaag | ccgagaagag | tgccgggccg | ggagaccgga | cgattattga | tccgtagcag | 720 |
| attcgct | | | | | | 727 |

<210> SEQ ID NO 98
<211> LENGTH: 746
<212> TYPE: DNA
<213> ORGANISM: Zea mays

-continued

```
<400> SEQUENCE: 98
aaaaaaccca cgggttcacg ggtttgggta ctataggaac aaacccgtac caataaaccc        60
gtcgggtata gatttatgcc cattaacaaa cccatggata tgaaaattga tccaaacccg       120
taccctaata gggtaaaaac ccatcgggtt tcgggtttcg agtacccatt gtcatcttta       180
acaggaagtg agtcatgggc ctcttgtgcg tttgcgcttc tcgcttcatg gtccgtgact       240
ttccacgggt acacatatgg gccctaccat ggctctctta tcaactgggc ctcgaagcct       300
agctagttga tggcttgcat aattgcattg catggtctcc tctgctccgt ccgactgagc       360
gattcttccg gtaggggagc tgcagtgcag ctggtgcatg gcgatggatg gctgcgagtg       420
gtccaagaat ttctccccgg catgtcctct cctccagacc tccaccgatg cagcaggctc       480
ctggtagagc taactaaatc ggggaccct tctcaagttt tcatcactat atatgcagca        540
gatacctaga agagcacgac cgagctagga gaagcgcgaa cgcgtgcatg cgcagacgtt       600
gaggtcgagg gacacggtat ctctgagctt catcggagag cgacccgcca ccgccacgct       660
tggccgcaag ccgagaagag tgccgggccg ggagaccgga cgattattga tccgtagcag       720
attcgctaat ggcggatacg gcggac                                            746
```

PLANT REGULATORY SEQUENCES FOR SELECTIVE CONTROL OF GENE EXPRESSION

RELATED APPLICATION DATA

This application is a divisional of application Ser. No. 09/846,903 filed on May 1, 2001, now abandoned currently which claims priority to U.S. Provisional Application 60/201,255, filed on May 1, 2000 both of which are herein incorporated by reference in their entirety.

FIELD OF THE INVENTION

The present invention relates to the isolation and use of nucleic acid molecules for control of gene expression in plants, specifically novel plant promoters.

BACKGROUND OF THE INVENTION

One of the goals of plant genetic engineering is to produce plants with agronomically important characteristics or traits. Recent advances in genetic engineering have provided the requisite tools to transform plants to contain and express foreign genes (Kahl et al., 1995, World Journal of Microbiology and Biotechnology 11:449-460). Particularly desirable traits or qualities of interest for plant genetic engineering would include, but are not limited to, resistance to insects, fungal diseases, and other pests and disease-causing agents, tolerances to herbicides, enhanced stability, yield, or shelf-life, environmental tolerances, and nutritional enhancements. The technological advances in plant transformation and regeneration have enabled researchers to take pieces of DNA, such as a gene or genes from a heterologous source, or a native source, but modified to have different or improved qualities, and incorporate the exogenous DNA into the plant's genome. The gene or gene(s) can then be expressed in the plant cell to exhibit the added characteristic(s) or trait(s). In one approach, expression of a novel gene that is not normally expressed in a particular plant or plant tissue may confer a desired phenotypic effect. In another approach, transcription of a gene or part of a gene in an antisense orientation may produce a desirable effect by preventing or inhibiting expression of an endogenous gene.

Isolated plant promoters are useful for modifying plants through genetic engineering to have desired phenotypic characteristics. In order to produce such a transgenic plant, a vector that includes a heterologous gene sequence that confers the desired phenotype when expressed in the plant is introduced into the plant cell. The vector also includes a plant promoter that is operably linked to the heterologous gene sequence, often a promoter not normally associated with the heterologous gene. The vector is then introduced into a plant cell to produce a transformed plant cell, and the transformed plant cell is regenerated into a transgenic plant. The promoter controls expression of the introduced DNA sequence to which the promoter is operably linked and thus affects the desired characteristic conferred by the DNA sequence.

Because the promoter is a regulatory element that plays an integral part in the overall expression of a gene or gene(s), it would be advantageous to have a variety of promoters to tailor gene expression such that a gene or gene(s) is transcribed efficiently at the right time during plant growth and development, in the optimal location in the plant, and in the amount necessary to produce the desired effect. In one case, for example, constitutive expression of a gene product may be beneficial in one location of the plant, but less beneficial in another part of the plant. In other cases, it may be beneficial to have a gene product produced at a certain developmental stage of the plant, or in response to certain environmental or chemical stimuli. The commercial development of genetically improved germplasm has also advanced to the stage of introducing multiple traits into crop plants, often referred to as a gene stacking approach. In this approach, multiple genes conferring different characteristics of interest can be introduced into a plant. It is important when introducing multiple genes into a plant, that each gene is modulated or controlled for optimal expression and that the regulatory elements are diverse, to reduce the potential of gene silencing that can be caused by recombination of homologous sequences. In light of these and other considerations, it is apparent that optimal control of gene expression and regulatory element diversity are important in plant biotechnology.

The proper regulatory sequences must be present and in the proper location with respect to the DNA sequence of interest for the newly inserted DNA to be transcribed and thereby, if desired, translated into a protein in the plant cell. These regulatory sequences include, but are not limited to, a promoter, a 5' untranslated leader, and a 3' polyadenylation sequence. The ability to select the tissues in which to transcribe such foreign DNA and the time during plant growth in which to obtain transcription of such foreign DNA is also possible through the choice of appropriate promoter sequences that control transcription of these genes.

A variety of different types or classes of promoters can be used for plant genetic engineering. Promoters can be classified on the basis of range or tissue specificity. For example, promoters referred to as constitutive promoters are capable of transcribing operatively linked DNA sequences efficiently and expressing said DNA sequences in multiple tissues. Tissue-enhanced or tissue-specific promoters can be found upstream and operatively linked to DNA sequences normally transcribed in higher levels in certain plant tissues or specifically in certain plant tissues. Other classes of promoters would include, but are not limited to, inducible promoters that can be triggered by external stimuli such as chemical agents, developmental stimuli, or environmental stimuli. Thus, the different types of promoters desired can be obtained by isolating the regulatory regions of DNA sequences that are transcribed and expressed in a constitutive, tissue-enhanced, or inducible manner.

The technological advances of high-throughput sequencing and bioinformatics has provided additional molecular tools for promoter discovery. Particular target plant cells, tissues, or organs at a specific stage of development, or under particular chemical, environmental, or physiological conditions can be used as source material to isolate the mRNA and construct cDNA libraries. The cDNA libraries are quickly sequenced, and the expressed sequences can be catalogued electronically. Using sequence analysis software, thousands of sequences can be analyzed in a short period, and sequences from selected cDNA libraries can be compared. The combination of laboratory and computer-based subtraction methods allows researchers to scan and compare cDNA libraries and identify sequences with a desired expression profile. For example, sequences expressed preferentially in one tissue can be identified by comparing a cDNA library from one tissue to cDNA libraries of other tissues and electronically "subtracting" common sequences to find sequences only expressed in the target tissue of interest. The tissue enhanced sequence can then be used as a probe or primer to clone the corresponding full-length cDNA. A genomic library of the target plant can then be used to isolate the corresponding gene and the associated regulatory elements, including but not limited to promoter sequences.

Multiple genes that have a desired expression profile such as in male reproductive tissues can be isolated by selectively comparing cDNA libraries of target tissues of interest with non-target or background cDNA libraries to find the 5' regulatory regions associated with the expressed sequences in those target libraries. The promoter sequences can be isolated from the genomic DNA flanking the desired genes. The isolated promoter sequences can be used for selectively modulating expression of any operatively linked gene and provide additional regulatory element diversity in a plant expression vector in gene stacking approaches.

SUMMARY OF THE INVENTION

The present invention provides isolated plant promoter sequences that comprise nucleic acid regions located upstream of the 5' end of plant DNA structural coding sequences that are transcribed in male reproductive tissues. The plant promoter sequences are capable of modulating or initiating transcription of DNA sequences to which they are operably linked.

The present invention provides nucleic acid sequences comprising regulatory sequences as shown in SEQ ID NOS: 79-98 that are located upstream of the 5' end of plant DNA structural coding sequences and transcribed in male reproductive tissues.

In one aspect, the present invention provides nucleic acid sequences comprising a sequence selected from the group consisting of SEQ ID NOS: 79-98 or any fragments or regions of the sequence or cis elements of the sequence that are capable of regulating transcription of operably linked DNA sequences.

The present invention also provides nucleic acid sequences comprising a sequence selected from the group consisting of SEQ ID NOS: 79-98 that are promoters.

Another aspect of the present invention relates to the use of one or more cis elements, or fragments thereof of the disclosed 5' promoter sequences that can be combined to create novel promoters or used in a novel combination with another heterologous regulatory sequence to create a chimeric promoter capable of modulating transcription of an operably linked DNA sequence.

Hence, the present invention relates to the use of nucleic acid sequences disclosed in SEQ ID NOS: 79-98 or any fragment, region, or cis element of the disclosed sequences that are capable of regulating transcription of a DNA sequence when operably linked to the DNA sequence. Therefore, the invention not only encompasses the sequences as disclosed in SEQ ID NOS: 79-98, but also includes any truncated or deletion derivatives, or fragments or regions thereof that are capable of functioning independently as a promoter including cis elements that are capable of functioning as regulatory sequences in conduction with one or more regulatory sequences when operably linked to a transcribable sequence.

The present invention thus encompasses a novel promoter or chimeric or hybrid promoter comprising a nucleic acid of SEQ ID NOS: 79-98. The chimeric or hybrid promoters can consist of any length fragments, regions, or cis elements of the disclosed sequences of SEQ ID NOS: 79-98 combined with any other transcriptionally active minimal or full-length promoter. For example, a promoter sequence selected from SEQ ID NOS: 79-98 may be combined with a CaMV 35S or other promoter to construct a novel chimeric promoter. A minimal promoter can also be used in combination with the nucleic acid sequences of the present invention. A novel promoter also comprises any promoter constructed by engineering the nucleic acid sequences disclosed in SEQ ID NOS: 79-98 or any fragment, region, or cis element of the disclosed sequences in any manner sufficient to transcribe an operably linked DNA sequence.

Another aspect of the present invention relates to the ability of the promoter sequences of SEQ ID NOS: 79-98, or fragments, regions, or cis elements thereof to regulate transcription of operably linked transcribable sequences in male reproductive tissues. Fragments, regions, or cis elements of SEQ ID NOS: 79-98 that are capable of regulating transcription of operably linked DNA sequences in certain tissues may be isolated from the disclosed nucleic acid sequences of SEQ ID NOS: 79-98 and used to engineer novel promoters.

The present invention also encompasses DNA constructs comprising the disclosed sequences as shown in SEQ ID NOS: 79-98 or any fragments, regions, or cis elements thereof, including novel promoters generated using the disclosed sequences or any fragment, region, or cis element of the disclosed sequences.

The present invention also includes any transgenic cells and plants containing the DNA disclosed in the sequences as shown in SEQ ID NOS: 79-98, or any fragments, regions, or cis elements thereof.

The present invention also provides a method of regulating transcription of a DNA sequence comprising operably linking the DNA sequence to any promoter comprising a nucleic acid comprising all or any fragment, region or cis element of a sequence selected from the group consisting of SEQ ID NOS: 79-98.

In another embodiment the present invention provides a method of regulating expression of DNA sequences in male reproductive tissues by operably linking a sequence selected from the group consisting of SEQ ID NOS: 79-98, or any fragment, region, or cis element of the disclosed sequences to any transcribable DNA sequence. The fragments, regions, or cis elements of the disclosed promoters as shown in SEQ ID NOS: 79-98 can be engineered and used independently in novel combinations including multimers, or truncated derivatives and the novel promoters can be operably linked with a transcribable DNA sequence. Alternatively the disclosed fragments, regions, or cis elements of the disclosed sequences can be used in combination with a heterologous promoter including a minimal promoter to create a novel chimeric or hybrid promoter and the novel chimeric promoter can be operably linked to a transcribable DNA sequence.

The present invention also provides a method of making a transgenic plant by introducing into a cell of a plant a DNA construct comprising: (i) a promoter comprising a nucleic acid comprising a sequence selected from the group consisting of SEQ ID NOS: 79-98, or fragment, region, or cis element thereof, and operably linked to the promoter, (ii) a transcribable DNA sequence and (iii) a 3' untranslated region.

The present invention also provides a method of isolating at least one 5' regulatory sequence of a desired expression profile from a target plant of interest by evaluating a collection of nucleic acid sequences of ESTs derived from one or more cDNA libraries prepared from a plant cell type of interest, comparing EST sequences from at least one target plant cDNA library and one or more non-target cDNA libraries of ESTs from a different plant cell type, subtracting common EST sequences found in both target and non-target libraries, designing gene-specific primers from the remaining ESTs after the subtraction that are representative of the targeted expressed sequences, and isolating the corresponding 5' flanking and regulatory sequences, that includes promoter sequences from a genomic library prepared from the target plant using the gene specific primers.

The foregoing and other aspects of the invention will become more apparent from the following detailed description and accompanying drawings.

BRIEF DESCRIPTION OF THE SEQUENCE LISTING

Figure 1:
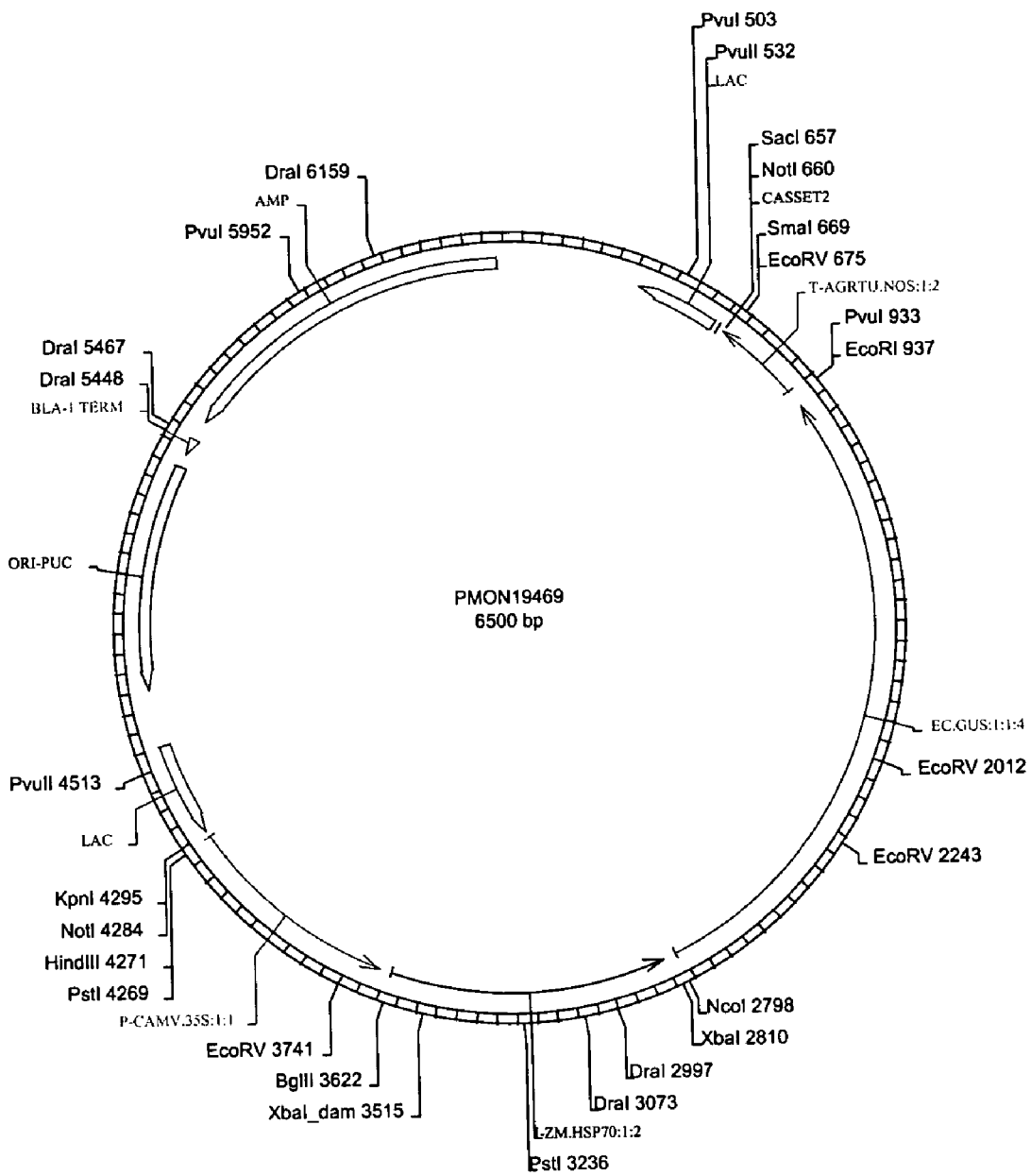
FIG. 1 is a plasmid map of pMON19469.

Seq ID NOs: 1-3 are adaptor sequences.

Seq ID NOs: 4-78 are fully synthesized primers derived from known *Zea mays* sequences.

Seq ID NOs: 79-98 are promoter sequences isolated from *Zea mays*.

DETAILED DESCRIPTION OF THE INVENTION

Definitions and Methods

The following definitions and methods are provided to better define the present invention and to guide those of ordinary skill in the art in the practice of the present invention. Unless otherwise noted, terms are to be understood according to conventional usage by those of ordinary skill in the relevant art. The nomenclature for DNA bases as set forth at 37 CFR § 1.822 is used. The standard one- and three-letter nomenclature for amino acid residues is used.

"Nucleic acid (sequence)" or "polynucleotide (sequence)" refers to single- or double-stranded DNA or RNA of genomic or synthetic origin, i.e., a polymer of deoxyribonucleotide or ribonucleotide bases, respectively, read from the 5' (upstream) end to the 3' (downstream) end. The nucleic acid can represent the sense or complementary (antisense) strand.

"Native" refers to a naturally occurring ("wild-type") nucleic acid sequence.

"Heterologous" sequence refers to a sequence that originates from a foreign source or species or, if from the same source, is modified from its original form.

An "isolated" nucleic acid sequence is substantially separated or purified away from other nucleic acid sequences that the nucleic acid is normally associated with in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids.

The term "substantially purified", as used herein, refers to a molecule separated from substantially all other molecules normally associated with it in its native state. More preferably, a substantially purified molecule is the predominant species present in a preparation. A substantially purified molecule may be greater than 60% free, preferably 75% free, more preferably 90% free from the other molecules (exclusive of solvent) present in the natural mixture. The term "substantially purified" is not intended to encompass molecules present in their native state.

A first nucleic acid sequence displays "substantial identity" to a reference nucleic acid sequence if, when optimally aligned (with appropriate nucleotide insertions or deletions totaling less than 20 percent of the reference sequence over the window of comparison) with the other nucleic acid (or its complementary strand), there is at least about 75% nucleotide sequence identity, preferably at least about 80% identity, more preferably at least about 85% identity, and most preferably at least about 90% identity over a comparison window of at least 20 nucleotide positions, preferably at least 50 nucleotide positions, more preferably at least 100 nucleotide positions, and most preferably over the entire length of the first nucleic acid. Optimal alignment of sequences for aligning a comparison window may be conducted by the local homology algorithm of Smith and Waterman (Adv. Appl. Math. 2: 482, 1981); by the homology alignment algorithm of Needleman and Wunsch (J. Mol. Biol. 48:443, 1970); by the search for similarity method of Pearson and Lipman (Proc. Natl. Acad. Sci. USA 85:2444, 1988); preferably by computerized implementations of these algorithms (GAP, BESTFIT, FASTA, and TFASTA) in the Wisconsin Genetics Software Package Release 7.0 (Genetics Computer Group, 575 Science Dr., Madison, Wis.). The reference nucleic acid may be a full-length molecule or a portion of a longer molecule. Alternatively, two nucleic acids have substantial identity if one hybridizes to the other under stringent conditions, as defined below.

A first nucleic acid sequence is "operably linked" with a second nucleic acid sequence when the sequences are so arranged that the first nucleic acid sequence affects the function of the second nucleic acid sequence. Preferably, the two sequences are part of a single contiguous nucleic acid molecule and more preferably are adjacent. For example, a promoter is operably linked to a gene if the promoter regulates or mediates transcription of the gene in a cell.

A "recombinant" nucleic acid is made by an artificial combination of two otherwise separated segments of sequence, e.g., by chemical synthesis or by the manipulation of isolated segments of nucleic acids by genetic engineering techniques. Techniques for nucleic-acid manipulation are well-known (see, e.g., Molecular Cloning: A Laboratory Manual, 2nd ed., vol. 1-3, ed. Sambrook et al., Cold Spring Harbor Laboratory Press, Cold Spring Harbor, N.Y., 1989, Sambrook et al., 1989; Current Protocols in Molecular Biology, ed. Ausubel et al., Greene Publishing and Wiley-Interscience, New York, 1992, with periodic updates, Ausubel et al., 1992; and PCR Protocols: A Guide to Methods and Applications, Academic Press: San Diego, Innis et al., 1990). Methods for chemical synthesis of nucleic acids are discussed, for example, in Beaucage and Carruthers (Tetra. Letts. 22:1859-1862, 1981), and Matteucci et al. (J. Am. Chem. Soc. 103:3185, 1981). Chemical synthesis of nucleic acids can be performed, for example, on commercial automated oligonucleotide synthesizers.

A "synthetic nucleic acid sequence" can be designed and chemically synthesized for enhanced expression in particular host cells and for the purposes of cloning into appropriate vectors. Host cells often display a preferred pattern of codon usage (Murray et al., 1989). Synthetic DNAs designed to enhance expression in a particular host should therefore reflect the pattern of codon usage in the host cell. Computer programs are available for these purposes including but not limited to the "BestFit" or "Gap" programs of the Sequence Analysis Software Package, Genetics Computer Group, Inc. (University of Wisconsin Biotechnology Center, Madison, Wis. 53711).

"Amplification" of nucleic acids or "nucleic acid reproduction" refers to the production of additional copies of a nucleic acid sequence and is carried out using polymerase chain reaction (PCR) technologies. A variety of amplification methods are known in the art and are described, inter alia, in U.S. Pat. Nos. 4,683,195 and 4,683,202 and by Innis et al. (PCR Protocols: A Guide to Methods and Applications, Academic Press, San Diego, 1990). In PCR, a primer refers to a short oligonucleotide of defined sequence that is annealed to a DNA template to initiate the polymerase chain reaction.

"Transformed", "transfected", or "transgenic" refers to a cell, tissue, organ, or organism into which has been introduced a foreign nucleic acid, such as a recombinant vector. Preferably, the introduced nucleic acid is integrated into the genomic DNA of the recipient cell, tissue, organ or organism such that the introduced nucleic acid is inherited by subsequent progeny. A "transgenic" or "transformed" cell or organism also includes progeny of the cell or organism and progeny produced from a breeding program employing such a "transgenic" plant as a parent in a cross and exhibiting an altered phenotype resulting from the presence of a recombinant construct or vector.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression. Some genes can be transcribed into mRNA and translated into polypeptides (structural genes); other genes can be transcribed into RNA (e.g., rRNA, tRNA); and other types of genes function as regulators of expression (regulator genes).

"Expression" of a gene refers to the transcription of a gene to produce the corresponding mRNA and translation of this mRNA to produce the corresponding gene product, i.e., a peptide, polypeptide, or protein. Gene expression is controlled or modulated by regulatory elements including 5' regulatory elements such as promoters.

"Genetic component" refers to any nucleic acid sequence or genetic element that may also be a component or part of an expression vector. Examples of genetic components include, but are not limited to, promoter regions, 5' untranslated leaders, introns, genes, 3' untranslated regions, and other regulatory sequences or sequences that affect transcription or translation of one or more nucleic acid sequences.

The terms "recombinant DNA construct", "recombinant vector", "expression vector" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner.

"Complementary" refers to the natural association of nucleic acid sequences by base-pairing (A-G-T pairs with the complementary sequence A-C-T). Complementarity between two single-stranded molecules may be partial, if only some of the nucleic acids pair are complementary, or complete, if all bases pair are complementary. The degree of complementarity affects the efficiency and strength of hybridization and amplification reactions.

"Homology" refers to the level of similarity between nucleic acid or amino acid sequences in terms of percent nucleotide or amino acid positional identity, respectively, i.e., sequence similarity or identity. Homology also refers to the concept of similar functional properties among different nucleic acids or proteins.

"ESTs" or Expressed Sequence Tags are short sequences of randomly selected clones from a cDNA (or complementary DNA) library that are representative of the cDNA inserts of these randomly selected clones (McCombie et al., Nature Genetics, 1:124, 1992; Kurata et al., Nature Genetics, 8: 365, 1994; Okubo et al., Nature Genetics, 2: 173, 1992).

The term "electronic Northern" refers to a computer-based sequence analysis that allows sequences from multiple cDNA libraries to be compared electronically based on parameters the researcher identifies including abundance in EST populations in multiple cDNA libraries, or exclusively to EST sets from one or combinations of libraries.

"Subsetting" refers to a method of comparing nucleic acid sequences from different or multiple sources that can be used to assess the expression profile of the nucleic acid sequences that reflects gene transcription activity and message stability in a particular tissue, at a particular time, or under particular conditions.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, organ, or cell type, a promoter may display "enhanced" expression, i.e., a higher level of expression, in one part (e.g., cell type, tissue, or organ) of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example, by chemical compounds (chemical inducers) or in response to environmental, hormonal, chemical, or developmental signals. Inducible or regulated promoters include, for example, promoters regulated by light, heat, stress, flooding or drought, phytohormones, wounding, or chemicals such as ethanol, jasmonate, salicylic acid, or safeners.

Any plant promoter can be used as a 5' regulatory sequence for modulating expression of a particular gene or genes. One preferred promoter would be a plant RNA polymerase II promoter. Plant RNA polymerase II promoters, like those of other higher eukaryotes, have complex structures and are comprised of several distinct elements. One such element is the TATA box or Goldberg-Hogness box, which is required for correct expression of eukaryotic genes in vitro and accurate, efficient initiation of transcription in vivo. The TATA box is typically positioned at approximately −25 to −35, that is, at 25 to 35 basepairs (bp) upstream (5') of the transcription initiation site, or cap site, which is defined as position +1 (Breathnach and Chambon, Ann. Rev. Biochem. 50:349-383, 1981; Messing et al., In: Genetic Engineering of Plants, Kosuge et al., eds., pp. 211-227, 1983). Another common element, the CCAAT box, is located between −70 and −100 bp. In plants, the CCAAT box may have a different consensus sequence than the functionally analogous sequence of mammalian promoters (the plant analogue has been termed the "AGGA box" to differentiate it from its animal counterpart; Messing et al., In: Genetic Engineering of Plants, Kosuge et al., eds., pp. 211-227, 1983). In addition, virtually all promoters include additional upstream activating sequences or enhancers (Benoist and Chambon, Nature 290: 304-310, 1981; Gruss et al., Proc. Natl. Acad. Sci. USA 78:943-947, 1981; and Khoury and Gruss, Cell 27:313-314, 1983) extending from around −100 bp to −1,000 bp or more upstream of the transcription initiation site. Enhancers have also been found 3' to the transcriptional start site.

When fused to heterologous DNA sequences, such promoters typically cause the fused sequence to be transcribed in a manner that is similar to that of the gene sequence that the promoter is normally associated with. Promoter fragments that include regulatory sequences can be added (for example, fused to the 5' end of, or inserted within, an active promoter having its own partial or complete regulatory sequences (Fluhr et al., Science 232:1106-1112, 1986; Ellis et al., EMBO J. 6:11-16, 1987; Strittmatter and Chua, Proc. Nat. Acad. Sci. USA 84:8986-8990, 1987; Poulsen and Chua, Mol. Gen. Genet. 214:16-23, 1988; Comai et al., Plant Mol. Biol. 15:373-381, 1991). Alternatively, heterologous regulatory sequences can be added to the 5' upstream region of an inactive, truncated promoter, e.g., a promoter including only the core TATA and, sometimes, the CCAAT elements (Fluhr et al., Science 232:1106-1112, 1986; Strittmatter and Chua, Proc. Nat. Acad. Sci. USA 84:8986-8990, 1987; Aryan et al., Mol. Gen. Genet. 225:65-71, 1991).

Promoters are typically comprised of multiple distinct "cis-acting transcriptional regulatory elements," or simply "cis-elements," each of which appears to confer a different aspect of the overall control of gene expression (Strittmatter and Chua, Proc. Nat. Acad. Sci. USA 84:8986-8990, 1987; Ellis et al., EMBO J. 6:11-16, 1987; Benfey et al., EMBO J. 9:1677-1684, 1990). Cis elements bind trans-acting protein factors that regulate transcription. Some cis elements bind more than one factor, and trans-acting transcription factors may interact with different affinities with more than one cis element (Johnson and McKnight, Ann. Rev. Biochem. 58:799-839, 1989). Plant transcription factors, corresponding cis elements, and analysis of their interaction are discussed, for example, in Martin (Curr. Opinions Biotech. 7:130-138, 1996), Murai (Methods in Plant Biochemistry and Molecular Biology, Dashek, ed., CRC Press, 1997, pp. 397-422), and Maliga et al. (Methods in Plant Molecular Biology, Cold Spring Harbor Press, 1995, pp. 233-300). The promoter sequences of the present invention can contain "cis elements" that can confer or modulate gene expression.

Cis elements can be identified by a number of techniques, including deletion analysis, i.e., deleting one or more nucleotides from the 5' end or internal to a promoter; DNA binding protein analysis using Dnase I footprinting; methylation interference; electrophoresis mobility-shift assays, in vivo genomic footprinting by ligation-mediated PCR; and other conventional assays; or by sequence similarity with known cis element motifs by conventional sequence comparison methods. The fine structure of a cis element can be further studied by mutagenesis (or substitution) of one or more nucleotides or by other conventional methods (see for example, Methods in Plant Biochemistry and Molecular Biology, Dashek, ed., CRC Press, 1997, pp. 397-422; and Methods in Plant Molecular Biology, Maliga et al., eds., Cold Spring Harbor Press, 1995, pp. 233-300).

Cis elements can be obtained by chemical synthesis or by cloning from promoters that include such elements, and they can be synthesized with additional flanking sequences that contain useful restriction enzyme sites to facilitate subsequent manipulation. In one embodiment, the promoters are comprised of multiple distinct "cis-acting transcriptional regulatory elements," or simply "cis-elements," each of which appears to confer a different aspect of the overall control of gene expression (Strittmatter and Chua, Proc. Nat. Acad. Sci. USA 84:8986-8990, 1987; Ellis et al., EMBO J. 6:11-16, 1987; Benfey et al., EMBO J. 9:1677-1684, 1990). In a preferred embodiment, sequence regions comprising "cis elements" of the nucleic acid sequences of SEQ ID NOS: 79-98 are identified using computer programs designed specifically to identify cis elements, or domains or motifs within sequences.

The present invention includes cis elements of SEQ ID NOS: 79-98, or homologues of cis elements known to affect gene regulation that show homology with the nucleic acid sequences of the present invention. A number of such elements are known in the literature, such as elements that are regulated by numerous factors such as light, heat, or stress; elements that are regulated or induced by pathogens or chemicals, and the like. Such elements may either positively or negatively regulated gene expression, depending on the conditions. Examples of cis elements would include, but are not limited to, oxygen responsive elements (Cowen et al., J. Biol. Chem. 268(36):26904, 1993), light regulatory elements (see for example, Bruce and Quaill, Plant Cell 2(11): 1081, 1990; and Bruce et al., EMBO J. 10:3015, 1991), a cis element reponsive to methyl jasmonate treatment (Beaudoin and Rothstein, Plant Mol. Biol. 33:835, 1997), salicylic acid responsive elements (Strange et al., Plant J. 11:1315, 1997), heat shock response elements (Pelham et al., Trends Genet. 1:31, 1985), elements responsive to wounding and abiotic stress (Loace et al., Proc. Natl. Acad. Sci. U.S.A. 89:9230, 1992; Mhiri et al., Plant Mol. Biol. 33:257, 1997), low temperature elements (Baker et al., Plant Mol. Biol. 24:701, 1994; Jiang et al., Plant Mol. Biol. 30:679, 1996; Nordin et al., Plant Mol. Biol. 21:641, 1993; Zhou et al., J. Biol. Chem. 267:23515, 1992), and drought responsive elements, (Yamaguchi et al., Plant Cell 6:251-264, 1994; Wang et al., Plant Mol. Biol. 28:605, 1995; Bray, Trends in Plant Science 2:48, 1997).

The present invention therefore encompasses fragments or cis elements of the disclosed nucleic acid molecules, and such nucleic acid fragments can include any region of the disclosed sequences. The promoter regions or partial promoter regions of the present invention as shown in SEQ ID NOS: 79-98 can contain one or more regulatory elements including but not limited to cis elements or domains that are capable of regulating expression of operably linked DNA sequences, preferably in male reproductive tissues.

Plant promoters can include promoters produced through the manipulation of known promoters to produce synthetic, chimeric, or hybrid promoters. Such promoters can also combine cis elements from one or more promoters, for example, by adding a heterologous regulatory sequence to an active promoter with its own partial or complete regulatory sequences (Ellis et al., EMBO J. 6:11-16, 1987; Strittmatter and Chua, Proc. Nat. Acad. Sci. USA 84:8986-8990, 1987; Poulsen and Chua, Mol. Gen. Genet. 214:16-23, 1988; Comai et al., Plant. Mol. Biol. 15:373-381, 1991). Chimeric promoters have also been developed by adding a heterologous regulatory sequence to the 5' upstream region of an inactive, truncated promoter, i.e., a promoter that includes only the core TATA and, optionally, the CCAAT elements (Fluhr et al., Science 232:1106-1112, 1986; Strittmatter and Chua, Proc. Nat. Acad. Sci. USA 84:8986-8990, 1987; Aryan et al., Mol. Gen. Genet. 225:65-71, 1991).

The design, construction, and use of chimeric or hybrid promoters comprising one or more of cis elements of SEQ ID NOS: 79-98 for modulating or regulating the expression of operably linked nucleic acid sequences is also encompassed by the present invention.

The promoter sequences, fragments, regions or cis elements thereof of SEQ ID NOS: 79-98 are capable of transcribing operably linked DNA sequences in male reproductive tissues and therefore can selectively regulate expression of genes in these tissues.

The promoter sequences of the present invention are useful for regulating gene expression in male reproductive tissues such as tassels, anthers, and pollen. For a number of agronomic traits, transcription of a gene or genes of interest is desirable in multiple tissues in order to confer the desired characteristic(s). The availability of suitable promoters that regulate transcription of operably linked genes in selected target tissues of interest is important because it may not be desirable to have expression of a gene in every tissue, but only in certain tissues. For example, if one desires to selectively express a target gene for controlling fertility in corn, it would be advantageous to have a promoter that confers enhanced expression in reproductive tissues. The promoter sequences of the present invention are capable of regulating operably linked DNA sequence particularly in male reproductive tissues and have utility for regulating transcription of any target gene including, but not limited to, genes for control of fertility, insect or pathogen tolerance, herbicide tolerance or any gene of interest. Consequently, it is important to have a wide variety of choices of 5' regulatory elements for any plant biotechnology strategy.

The advent of genomics, which comprises molecular and bioinformatics techniques, has resulted in rapid sequencing and analyses of a large number of DNA samples from a vast number of targets, including but not limited to plant species of agronomic importance. To identify the nucleic acid sequences of the present invention from a database or collection of cDNA sequences, the first step involves constructing cDNA libraries from specific plant tissue targets of interest. Briefly, the cDNA libraries are first constructed from these tissues that are harvested at a particular developmental stage or under particular environmental conditions. By identifying differentially expressed genes in plant tissues at different developmental stages or under different conditions, the corresponding regulatory sequences of those genes can be identified and isolated. Transcript imaging enables the identification of tissue-preferred sequences based on specific imaging of nucleic acid sequences from a cDNA library. By transcript imaging as used herein is meant an analysis that compares the abundance of expressed genes in one or more libraries. The clones contained within a cDNA library are sequenced and the sequences compared with sequences from publicly available databases. Computer-based methods allow the researcher to provide queries that compare sequences from multiple libraries. The process enables quick identification of clones of interest compared with conventional hybridization subtraction methods known to those of skill in the art.

Using conventional methodologies, cDNA libraries can be constructed from the mRNA (messenger RNA) of a given tissue or organism using poly dT primers and reverse transcriptase (Efstratiadis et al., Cell 7:279, 1976; Higuchi et al., Proc. Natl. Acad. Sci. U.S.A. 73:3146, 1976; Maniatis et al., Cell 8:163, 1976; Land et al., Nucleic Acids Res. 9:2251, 1981; Okayama et al., Mol. Cell. Biol. 2:161, 1982; Gubler et al., Gene 25:263, 1983).

Several methods can be employed to obtain full-length cDNA constructs. For example, terminal transferase can be used to add homopolymeric tails of dC residues to the free 3' hydroxyl groups (Land et al., Nucleic Acids Res. 9:2251, 1981). This tail can then be hybridized by a poly dG oligo that can act as a primer for the synthesis of full length second strand cDNA. Okayama and Berg, reported a method for obtaining full-length cDNA constructs (Mol. Cell Biol. 2:161, 1982). This method has been simplified by using synthetic primer adapters that have both homopolymeric tails for priming the synthesis of the first and second strands and restriction sites for cloning into plasmids (Coleclough et al., Gene 34:305, 1985) and bacteriophage vectors (Krawinkel et al., Nucleic Acids Res. 14:1913, 1986; Han et al., Nucleic Acids Res. 15:6304, 1987).

These strategies can be coupled with additional strategies for isolating rare mRNA populations. For example, a typical mammalian cell contains between 10,000 and 30,000 different mRNA sequences (Davidson, Gene Activity in Early Development, 2nd ed., Academic Press, New York, 1976). The number of clones required to achieve a given probability that a low-abundance mRNA will be present in a cDNA library is $N=(\ln(1-P))/(\ln(1-1/n))$ where N is the number of clones required, P is the probability desired, and 1/n is the fractional proportion of the total mRNA that is represented by a single rare mRNA (Sambrook et al., 1989).

One method to enrich preparations of mRNA for sequences of interest is to fractionate by size. One such method is to fractionate by electrophoresis through an agarose gel (Pennica et al., Nature 301:214, 1983). Another method employs sucrose gradient centrifugation in the presence of an agent, such as methylmercuric hydroxide, that denatures secondary structure in RNA (Schweinfest et al., Proc. Natl. Acad. Sci. U.S.A. 79:4997-5000, 1982).

A frequently adopted method is to construct equalized or normalized cDNA libraries (Ko, Nucleic Acids Res. 18:5705, 1990; Patanjali et al., Proc. Natl. Acad. Sci. U.S.A. 88:1943, 1991). Typically, the cDNA population is normalized by subtractive hybridization (Schmid et al., J. Neurochem. 48:307, 1987; Fargnoli et al., Anal. Biochem. 187: 364, 1990; Travis et al., Proc. Natl. Acad. Sci. U.S.A. 85:1696, 1988; Kato, Eur. J. Neurosci. 2:704, 1990; Schweinfest et al., Genet. Anal. Tech. Appl. 7:64, 1990). Subtraction represents another method for reducing the population of certain sequences in the cDNA library (Swaroop et al., Nucleic Acids Res. 19:1954, 1991). Normalized libraries can be constructed using the Soares procedure (Soares et al., Proc. Natl. Acad. Sci. U.S.A. 91:9228, 1994). This approach is designed to reduce the initial 10,000-fold variation in individual cDNA frequencies to achieve abundance within one order of magnitude while maintaining the overall sequence complexity of the library. In the normalization process, the prevalence of high-abundance cDNA clones decreases dramatically, clones with mid-level abundance are relatively unaffected, and clones for rare transcripts are effectively increased in abundance.

ESTs can be sequenced by a number of methods. Two basic methods can be used for DNA sequencing, the chain termination method (Sanger et al., Proc. Natl. Acad. Sci. U.S.A. 74: 5463, 1977) and the chemical degradation method (Maxam and Gilbert, Proc. Nat. Acad. Sci. U.S.A.

74: 560, 1977). Automation and advances in technology, such as the replacement of radioisotopes with fluorescence-based sequencing, have reduced the effort required to sequence DNA (Craxton, Methods, 2: 20, 1991; Ju et al., Proc. Natl. Acad. Sci. U.S.A. 92: 4347, 1995; Tabor and Richardson, Proc. Natl. Acad. Sci. U.S.A. 92: 6339, 1995). Automated sequencers are available from a number of manufacturers including Pharmacia Biotech, Inc., Piscataway, N.J. (Pharmacia ALF); LI-COR, Inc., Lincoln, Nebr. (LI-COR 4,000); and Millipore, Bedford, Mass. (Millipore BaseStation).

ESTs longer than 150 bp have been found to be useful for similarity searches and mapping (Adams et al., Science 252:1651, 1991). EST sequences normally range from 150-450 bases. This is the length of sequence information that is routinely and reliably generated using single run sequence data. Typically, only single run sequence data is obtained from the cDNA library (Adams et al., Science 252:1651, 1991). Automated single run sequencing typically results in an approximately 2-3% error or base ambiguity rate (Boguski et al., Nature Genetics, 4:332, 1993).

EST databases have been constructed or partially constructed from, for example, *C. elegans* (McCombrie et al., Nature Genetics 1:124, 1992); human liver cell line HepG2 (Okubo et al., Nature Genetics 2:173, 1992); human brain RNA (Adams et al., Science 252:1651, 1991; Adams et al., Nature 355:632, 1992); *Arabidopsis*, (Newman et al., Plant Physiol. 106:1241, 1994); and rice (Kurata et al., Nature Genetics 8:365, 1994). The present invention uses ESTs from a number of cDNA libraries prepared from male reproductive tissues of corn as a tool for the identification of genes expressed in these target tissues, which then facilitates the isolation of 5' regulatory sequences such as promoters that regulate the genes.

Computer-based sequence analyses can be used to identify differentially expressed sequences including, but not limited to, those sequences expressed in one tissue compared with another tissue. For example, a different set of sequences can be found from cDNA isolated from root tissue versus leaf tissue. Accordingly, sequences can be compared from cDNA libraries prepared from plants grown under different environmental or physiological conditions. Once the preferred sequences are identified from the cDNA library of interest, the genomic clones can be isolated from a genomic library prepared from the plant tissue, and corresponding regulatory sequences including but not limited to 5' regulatory sequences can be identified and isolated.

In one preferred embodiment, expressed sequence tags (EST) sequences from a variety of cDNA libraries are catalogued in a sequence database. This database is used to identify promoter targets from a particular tissue of interest. The selection of expressed sequence tags for subsequent promoter isolation is reflective of the presence of one or more sequences among the representative ESTs from a random sampling of an individual cDNA library or a collection of cDNA libraries. For example, the identification of regulatory sequences that direct the expression of transcripts in male reproductive tissues is conducted by identifying ESTs found in tissues such as tassel and anther, and absent or in lower abundance in other cDNA libraries in the database. The identified EST leads are then evaluated for relative abundance within the library and the expression profile for a given EST is assessed. By abundance as used herein is meant the number of times a clone or cluster of clones appears in a library. The sequences that are enhanced or in high abundance in a specific tissue or organ that represent a target expression profile are identified in this manner and primers can be designed from the identified EST sequences. A PCR-based approach can be used to amplify flanking regions from a genomic library of the target plant of interest. A number of methods are known to those of skill in the art to amplify unknown DNA sequences adjacent to a core region of known sequence. Methods include but are not limited to inverse PCR (IPCR), vectorette PCR, Y-shaped PCR, and genome walking approaches.

In a preferred embodiment, genomic DNA ligated to an adaptor is subjected to a primary round of PCR amplification with a gene-specific primer and a primer that anneals to the adaptor sequence. The PCR product is next used as the template for a nested round of PCR amplification with a second gene-specific primer and second adaptor. The resulting fragments from the nested PCR reaction are then isolated, purified and subcloned into an appropriate vector. The fragments are sequenced, and the translational start sites can be identified when the EST is derived from a truncated cDNA. The fragments can be cloned into plant expression vectors as transcriptional or translational fusions with a reporter gene such as β-glucuronidase (GUS). The constructs can be tested in transient analyses, and subsequently the 5' regulatory regions are operably linked to other genes and regulatory sequences of interest in a suitable plant transformation vector and the transformed plants are analyzed for the expression of the gene(s) of interest, by any number of methods known to those of skill in the art.

Any plant can be selected for the identification of genes and regulatory sequences. Examples of suitable plant targets for the isolation of genes and regulatory sequences would include but are not limited to Acadia, alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassaya, castorbean, cauliflower, celery, cherry, chicory, cilantro, citrus, clementines, clover, coconut, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lily, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. Particularly preferred plant targets would include corn, cotton, rice, soybean, and wheat.

The nucleic acid molecules of the present invention are isolated from corn (*Zea mays*). The corn plant develops about 20-21 leaves, silks about 65 days post-emergence, and matures about 125 days post-emergence. Normal corn plants follow a general pattern of development, but the time interval between different stages and morphology varies between different hybrids, growth and environmental conditions.

There are a number of identifiable stages in corn plant development. The stages are defined as vegetative (V) and reproductive (R) stages. Subdivisions of the V stages are numerically designated as V1, V2, V3, etc., through V(n) where (n) represents the last leaf stage before tasseling (VT) and the first V stage is the emergence (VE) stage. For example, VE is the emergence from the soil of a seedling leaf, V1 represents the first true leaf, V2 represents the second leaf, etc. The reproductive stages include the first appearance of silk to the mature seed and are represented as follows: R1 is silking, R2 is blistering, R3 is the milk stage, R4 is the dough stage, R5 is the dent stage, and R6 is physiological maturity (see for example, Ritchie et al. (1986) *How a Corn Plant Develops*, Iowa State University of Science and Technology Cooperative Exension Service, Ames, Iowa 48: 1-21).

Any type of plant tissue can be used as a target tissue for the identification of genes and associated regulatory sequences. For the present invention, corn male reproductive tissue is used. More preferably corn tassel tissues are the target tissues for identification of promoter sequences. Corn cDNA libraries can be constructed from several different plant developmental stages. More preferably corn plants at stages V6-V9 are used. Background or non-target libraries can include but are not limited to libraries such as leaf, root, embryo, callus, shoot, seedling, endosperm, culm, ear, and silks.

Any method that allows a differential comparison between different types or classes of sequences can be used to isolate genes or regulatory sequences of interest. For example, in one differential screening approach, a cDNA library from mRNA isolated from a particular tissue can be prepared in a bacteriophage host using a commercially available cloning kit. The plaques are spread onto plates containing lawns of a bacterial host such as *E. coli* to generate bacteriophage plaques. About $10^5$-$10^6$ plaques can be lifted onto DNA-binding membranes. Duplicate membranes are probed using probes generated from mRNA from the target and non-target or background tissue. The probes are labeled to facilitate detection after hybridization and development. Plaques that hybridize to target tissue-derived probes but not to non-target tissue derived probes that display a desired differential pattern of expression can be selected for further analysis. Genomic DNA libraries can also be prepared from a chosen species by partial digestion with a restriction enzyme and size selecting the DNA fragments within a particular size range. The genomic DNA can be cloned into a suitable vector including but not limited to a bacteriophage and prepared using a suitable vector such as a bacteriophage using a suitable cloning kit from any number of vendors (see for example Stratagene, La Jolla Calif. or Gibco BRL, Gaithersburg, Md.).

Differential hybridization techniques as described are well known to those of skill in the art and can be used to isolate a desired class of sequences. By classes of sequences as used herein is meant sequences that can be grouped based on a common identifier including but not limited to sequences isolated from a common target plant, a common library, or a common plant tissue type. In a preferred embodiment, sequences of interest are identified based on sequence analyses and querying of a collection of diverse cDNA sequences from libraries of different tissue types. The disclosed method provides an example of a differential screening approach based on electronic sequence analyses of plant ESTs derived from diverse cDNA libraries.

A number of methods used to assess gene expression are based on measuring the mRNA level in an organ, tissue, or cell sample. Typical methods include but are not limited to RNA blots, ribonuclease protection assays and RT-PCR. In another preferred embodiment, a high-throughput method is used whereby regulatory sequences are identified from a transcript profiling approach. The development of cDNA microarray technology enables the systematic monitoring of gene expression profiles for thousands of genes (Schena et al, Science, 270: 467, 1995). This DNA chip-based technology arrays thousands of cDNA sequences on a support surface. These arrays are simultaneously hybridized to multiple labeled cDNA probes prepared from RNA samples of different cell or tissue types, allowing direct comparative analysis of expression. This technology was first demonstrated by analyzing 48 *Arabidopsis* genes for differential expression in roots and shoots (Schena et al, Science, 270:467, 1995). More recently, the expression profiles of over 1400 genes were monitored using cDNA microarrays (Ruan et al, The Plant Journal 15:821, 1998). Microarrays provide a high-throughput, quantitative and reproducible method to analyze gene expression and characterize gene function. The transcript profiling approach using microarrays thus provides another valuable tool for the isolation of regulatory sequences such as promoters associated with those genes.

The present invention uses high throughput sequence analyses to form the foundation of rapid computer-based identification of sequences of interest. Those of skill in the art are aware of the resources available for sequence analyses. Sequence comparisons can be done by determining the similarity of the test or query sequence with sequences in publicly available or proprietary databases ("similarity analysis") or by searching for certain motifs ("intrinsic sequence analysis") (e.g., cis elements) (Coulson, Trends in Biotechnology, 12:76, 1994; Birren et al., Genome Analysis, 1:543, 1997).

The nucleotide sequences provided in SEQ ID NOS: 79-98 or fragments thereof, or complements thereof, or a nucleotide sequence at least 90% identical, preferably 95% identical even more preferably 99% or 100% identical to the sequence provided in SEQ ID NOS: 79-98 or fragment thereof, or complement thereof, can be "provided" in a variety of mediums to facilitate use. Such a medium can also provide a subset thereof in a form that allows one of skill in the art to examine the sequences.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable media can be used to create a manufacture comprising computer readable medium having recorded thereon a nucleotide sequence of the present invention.

By providing one or more of nucleotide sequences of the present invention, those of skill in the art can routinely access the sequence information for a variety of purposes. Computer software is publicly available that allows one of skill in the art to access sequence information provided in a computer readable medium. Examples of public databases would include but are not limited to the DNA Database of Japan (DDBJ) (http://www.ddbj.nig.acjp/);Genbank (http://www.ncbi.nlm.nih.gov/web/Genbank/Index.html); and the European Molecular Biology Laboratory Nucleic Acid Sequence Database (EMBL) (http://www.ebi.ac.uk/ebi_docs/embl_db.html) or versions thereof. A number of different search algorithms have been developed, including but not limited to the suite of programs referred to as BLAST programs. There are five implementations of BLAST, three designed for nucleotide sequence queries (BLASTN, BLASTX, and TBLASTX) and two designed for protein sequence queries (BLASTP and TBLASTN) (Coulson, Trends in Biotechnology, 12:76-80, 1994; Birren et al., Genome Analysis, 1:543, 1997).

Any program designed for motif searching also has utility in the present invention. Sequence analysis programs designed for motif searching can be used for identification of cis elements. Preferred computer programs would include but are not limited to MEME, SIGNAL SCAN, and GENES-CAN. MEME is a program that identifies conserved motifs (either nucleic acid or peptide) in a group of unaligned sequences. MEME saves these motifs as a set of profiles. These profiles can be used to search a database of sequences. A MEME algorithm (version 2.2) can be found in version 10.0 of the GCG package; MEME (Bailey and Elkan, Machine Learning, 21(1-2):51-80, 1995 and the location of the website is http://www.sdsc.edu/MEME/meme/website/COPYRIGHT.html. SIGNALSCAN is a program that identifies known motifs in the test sequences using information from other motif databases (Prestridge, CABIOS 7, 203-206, 1991). SIGNALSCAN version 4.0 information is available at the following website: http://ibiosci.cbs.umn.edu/software/sigscan.html. The ftp site for SIGNALSCAN is ftp://biosci.cbs.umn.edu/software/sigscan.html. Databases used with SIGNALSCAN include PLACE (http://www.dna.affrc.go.ip/htdocs/PLACE; Higo et al., Nucleic Acids Research 27(1):297-300, 1999) and TRANSFAC (Heinemeye, X. et al., Nucleic Acid Research 27(1):318-322) that can be found at the following website: http://transfac.gbf.de/. GENESCAN is another suitable program for motif searching (Burge and Karlin, J. Mol. Biol. 268, 78-94, 1997), and version 1.0 information is available at the following website: http://gnomic.stanford.edu/GENESCAN-W.html. As used herein, "a target structural motif" or "target motif" refers any rationally selected sequence or combination of sequences in which the sequence(s) are chosen based on a three-dimensional configuration that is formed upon the folding of the target motif. There are a variety of target motifs known to those of skill in the art. Protein target motifs include, but are not limited to, enzymatic active sites and signal sequences. Preferred target motifs of the present invention would include but are not limited to promoter sequences, cis elements, hairpin structures and other expression elements such as protein binding sequences.

As used herein, "search means" refers to one or more programs that are implemented on the computer-based system to compare a target sequence or target structural motif with the sequence information stored within the data storage means. Search means are used to identify fragments or regions of the sequences of the present invention that match a particular target sequence or target motif. Multiple sequences can also be compared in order to identify common regions or motifs that may be responsible for specific functions. For example, cis elements or sequence domains that confer a specific expression profile can be identified when multiple promoter regions of similar classes of promoters are aligned and analyzed by certain software packages.

The present invention further provides systems, particularly computer-based systems, that contain the sequence information described herein. As used herein, a "computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means.

Those of skill in the art can appreciate that any one of the available computer-based systems are suitable for use in the present invention.

SEQ ID NOS: 4-76 are primers designed from the cDNA sequences identified from the computer-based sequence comparisons. These sequences are used to extend the nucleic acid sequence using polymerase chain reaction (PCR) amplification techniques (see for example, Mullis et al., Cold Spring Harbor Symp. Quant. Biol. 51:263, 1986; Erlich et al., European Patent Appln. 50,424; European Patent Appln. 84,796, European Patent Appln. 258,017, European Patent Appln. 237,362; Mullis, European Patent Appln. 201,184; Mullis et al., U.S. Pat. No. 4,683,202; Erlich, U.S. Pat. No. 4,582,788; and Saiki et al., U.S. Pat. No. 4,683,194). A number of PCR amplification methods are known to those of skill in the art and are used to identify nucleic acid sequences adjacent to a known sequence. For example, inverse PCR (IPCR) methods to amplify unknown DNA sequences adjacent to a core region of known sequence have been described. Other methods are also available such as capture PCR (Lagerstrom et al., PCR Methods Applic. 1:111, 1991), and walking PCR (Parker et al., Nucleic Acids Res 19:3055, 1991). A number of manufacturers have also developed kits based on modifications of these methods for the purposes of identifying sequences of interest. Technical advances including improvements in primer and adaptor design, improvements in the polymerase enzyme, and thermocycler capabilities have facilitated quicker, more efficient methods for isolating sequences of interest.

In a preferred embodiment, the flanking sequences containing the 5' regulatory elements of the present invention are isolated using a genome-walking approach (Universal GenomeWalker™ Kit, CLONTECH Laboratories, Inc., Palo Alto, Calif.). In brief, the purified genomic DNA is subjected to a restriction enzyme digest that produces genomic DNA fragments with ends that are ligated with GenomeWalker™ adaptors. GenomeWalker™ primers are used along with gene specific primers in two consecutive PCR reactions (primary and nested PCR reactions) to produce PCR products containing the 5' regulatory sequences that are subsequently cloned and sequenced.

In addition to their use in modulating gene expression, the promoter sequences of the present invention also have utility as probes or primers in nucleic acid hybridization experiments. The nucleic acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure (see for example Sambrook et al., 1989, at 9.52-9.55 and 9.47-9.52, 9.56-9.58; Kanehisa, Nucl. Acids Res. 12:203-213, 1984; Wetmur and Davidson, J. Mol. Biol. 31:349-370, 1968). Appropriate stringency conditions that promote DNA hybridization are, for example, 6.0× sodium chloride/sodium citrate (SSC) at about 45° C., followed by a wash of 2.0×SSC at 50° C., and they are known to those skilled in the art or can be found in laboratory manuals including but not limited to Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. For example, hybridization using DNA or RNA probes or primers can be performed at 65° C. in 6×SSC, 0.5% SDS, 5× Denhardt's, 100 µg/mL nonspecific DNA (e.g., sonicated salmon sperm DNA) with washing at 0.5×SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA fragments. Detection of DNA segments via hybridization is well-known to those of skill in the art. Thus depending on the application envisioned, one will desire to employ varying hybridization conditions to achieve varying degrees of selectivity of probe towards target sequence and the method of choice will depend on the desired results.

The nucleic acid sequences in SEQ ID NOS: 79-98, and any variants thereof, are capable of hybridizing to other nucleic acid sequences under appropriately selected conditions of stringency. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low stringency" conditions. Similarly, the molecules are said to be "complementary" if they can hybridize to one another with sufficient stability to permit them to remain annealed to one another under conventional "high stringency" conditions. Conventional stringency conditions are described by Sambrook et al. (Molecular Cloning, A Laboratory Manual, $2^{nd}$ Ed., Cold Spring Harbor Press, Cold Spring Harbor, N.Y., 1989), and by Haymes et al. (Nucleic Acid Hybridization, A Practical Approach, IRL Press, Washington, D.C., 1985).

In a preferred embodiment, the nucleic acid sequences SEQ ID NOS: 79-98 or a fragment, region, cis element, or oligomer of these sequences may be used in hybridization assays of other plant tissues to identify closely related or homologous genes and associated regulatory sequences. These include but are not limited to Southern or northern hybridization assays on any substrate including but not limited to an appropriately prepared plant tissue, cellulose, nylon, or combination filter, chip, or glass slide. Such methodologies are well known in the art and are available in a kit or preparation that can be supplied by commercial vendors.

Of course, nucleic acid fragments can also be obtained by other techniques such as by directly synthesizing the fragment by chemical means, as is commonly practiced by using an automated oligonucleotide synthesizer. Fragments can also be obtained by application of nucleic acid reproduction technology, such as the PCR™ (polymerase chain reaction) technology or by recombinant DNA techniques generally known to those of skill in the art of molecular biology. Regarding the amplification of a target nucleic-acid sequence (e.g., by PCR) using a particular amplification primer pair, "stringent PCR conditions" refer to conditions that permit the primer pair to hybridize only to the target nucleic-acid sequence to which a primer having the corresponding wild-type sequence (or its complement) would bind and preferably to produce a unique amplification product.

A fragment of a nucleic acid as used herein is a portion of the nucleic acid that is less than full-length. For example, for the present invention any length of nucleotide sequence that is less than the disclosed nucleotide sequences of SEQ ID NOS: 79-98 is considered to be a fragment. A fragment can also comprise at least a minimum length capable of hybridizing specifically with a native nucleic acid under stringent hybridization conditions as defined above. The length of such a minimal fragment is preferably at least 8 nucleotides, more preferably 15 nucleotides, even more preferably at least 20 nucleotides, and most preferably at least 30 nucleotides of a native nucleic acid sequence.

The nucleic acid sequences of the present invention can also be used as probes and primers. Nucleic acid probes and primers can be prepared based on a native gene sequence. A "probe" is an isolated nucleic acid to which is attached a conventional detectable label or reporter molecule, e.g., a radioactive isotope, ligand, chemiluminescent agent, or enzyme. "Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

Probes and primers are generally 15 nucleotides or more in length, preferably 20 nucleotides or more, more preferably 25 nucleotides, and most preferably 30 nucleotides or more. Such probes and primers hybridize specifically to a target DNA or RNA sequence under high stringency hybridization conditions and hybridize specifically to a target native sequence of another species under lower stringency conditions. Preferably, probes and primers according to the present invention have complete sequence similarity with the native sequence, although probes differing from the native sequence and that retain the ability to hybridize to target native sequences may be designed by conventional methods. Methods for preparing and using probes and primers are described (see Sambrook et al., 1989; Ausubel et al., 1992, and Innis et al., 1990). PCR-primer pairs can be derived from a known sequence, for example, by using computer programs intended for that purpose such as Primer (Version 0.5, © 1991, Whitehead Institute for Biomedical Research, Cambridge, Mass.). Primers and probes based on the native promoter sequences disclosed herein can be used to confirm and, if necessary, to modify the disclosed sequences by conventional methods, e.g., by re-cloning and re-sequencing.

In another embodiment, the nucleotide sequences of the promoters disclosed herein can be modified. Those skilled in the art can create DNA molecules that have variations in the nucleotide sequence. The nucleotide sequences of the present invention as shown in SEQ ID NOS: 79-98 may be modified or altered to enhance their control characteristics.

One preferred method of alteration of a nucleic acid sequence is to use PCR to modify selected nucleotides or regions of sequences. These methods are known to those of skill in the art. Sequences can be modified, for example by insertion, deletion or replacement of template sequences in a PCR-based DNA modification approach. "Variant" DNA molecules are DNA molecules containing changes in which one or more nucleotides of a native sequence is deleted, added, and/or substituted, preferably while substantially maintaining promoter function. In the case of a promoter fragment, "variant" DNA can include changes affecting the transcription of a minimal promoter to which it is operably linked. Variant DNA molecules can be produced, for example, by standard DNA mutagenesis techniques or by chemically synthesizing the variant DNA molecule or a portion thereof.

In another embodiment, the nucleotide sequences as shown in SEQ ID NOS: 79-98 include any length of said nucleotide sequences that are capable of regulating an operably linked DNA sequence. For example, the sequences as disclosed in SEQ ID NOS: 79-98 may be truncated or portions deleted and still be capable of regulating transcription of an operably linked DNA sequence. In a related embodiment, a cis element of the disclosed sequences may confer a particular specificity such as conferring enhanced expression of operably linked DNA sequences in certain tissues. Consequently, any sequence fragments, portions, or regions of the disclosed sequences of SEQ ID NOS: 79-98 can be used as regulatory sequences including but not limited to cis elements or motifs of the disclosed sequences. For example, one or more base pairs may be deleted from the 5' or 3' end of a promoter sequence to produce a "truncated" promoter. One or more base pairs can also be inserted, deleted, or substituted internally to a promoter sequence. Promoters can be constructed such that promoter fragments or elements are operably linked for example, by placing such a fragment upstream of a minimal promoter. A minimal or basal promoter is a piece of DNA that is capable of recruiting and binding the basal transcription machinery. One example of basal transcription machinery in eukaryotic cells is the RNA polymerase II complex and its accessory proteins. The enzymatic components of the basal transcription machinery are capable of initiating and elongating transcription of a given gene, utilizing a minimal or basal promoter. That is, there are not added cis-acting sequences in the promoter region that are capable of recruiting and binding transcription factors that modulate transcription, e.g., enhance, repress, render transcription hormone-dependent, etc. Substitutions, deletions, insertions or any combination thereof can be combined to produce a final construct.

Native or synthetic nucleic acids according to the present invention can be incorporated into recombinant nucleic acid constructs, typically DNA constructs, capable of introduction into and replication in a host cell. In one preferred embodiment, the nucleotide sequences of the present invention as shown in SEQ ID NOS: 79-98 or fragments, variants or derivatives thereof are incorporated into an expression vector cassette that includes the promoter regions of the present invention operably linked to a genetic component such as a selectable, screenable, or scorable marker gene. The disclosed nucleic acid sequences of the present invention are preferably operably linked to a genetic component such as a nucleic acid that confers a desirable characteristic associated with plant morphology, physiology, growth and development, yield, nutritional enhancement, disease or pest resistance, or environmental or chemical tolerance. These genetic components such as marker genes or agronomic genes of interest can function in the identification of a transformed plant cell or plant, or a produce a product of agronomic utility.

In a preferred embodiment, one genetic component produces a product that serves as a selection device and functions in a regenerable plant tissue to produce a compound that would confer upon the plant tissue resistance to an otherwise toxic compound. Genes of interest for use as a selectable, screenable, or scorable marker would include but are not limited to GUS (coding sequence for beta-glucuronidase), GFP (coding sequence for green fluorescent protein), LUX (coding gene for luciferase), antibiotic resistance marker genes, or herbicide tolerance genes. Examples of transposons and associated antibiotic resistance genes include the transposons Tns (b1a), Tn5 (nptII), Tn7 (dhfr), penicillins, kanamycin (and neomycin, G418, bleomycin); methotrexate (and trimethoprim); chloramphenicol; and tetracycline.

Characteristics useful for selectable markers in plants have been outlined in a report on the use of microorganisms (Advisory Committee on Novel Foods and Processes, July 1994). These include stringent selection with minimum number of nontransformed tissues, large numbers of independent transformation events with no significant interference with the regeneration, application to a large number of species, and availability of an assay to score the tissues for presence of the marker.

A number of selectable marker genes are known in the art and several antibiotic resistance markers satisfy these criteria, including those resistant to kanamycin (nptII), hygromycin B (aph IV) and gentamycin (aac3 and aacC4). Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase). A useful strategy for selection of transformants for herbicide resistance is described, e.g., in Vasil (Cell Culture and Somatic Cell Genetics of Plants, Vols. I-III, Laboratory Procedures and Their Applications Academic Press, New York, 1984). Particularly preferred selectable marker genes for use in the present invention would include genes that confer resistance to compounds such as antibiotics like kanamycin and herbicides like glyphosate (Della-Cioppa et al., Bio/Technology 5(6), 1987; U.S. Pat. No. 5,463,175; U.S. Pat. No. 5,633,435). Other selection devices can also be implemented and would still fall within the scope of the present invention.

For the practice of the present invention, conventional compositions and methods for preparing and using vectors and host cells are employed, as discussed, inter alia, in Sambrook et al., 1989. In a preferred embodiment, the host cell is a plant cell. A number of vectors suitable for stable transfection of plant cells or for the establishment of transgenic plants have been described in, e.g., Pouwels et al. (Cloning Vectors: A Laboratory Manual, 1985, supp. 1987); Weissbach and Weissbach (Methods for Plant Molecular Biology, Academic Press, 1989); Gelvin et al. (Plant Molecular Biology Manual, Kluwer Academic Publishers, 1990); and Croy (Plant Molecular Biology LabFax, BIOS Scientific Publishers, 1993). Plant expression vectors can include, for example, one or more cloned plant genes under the transcriptional control of 5' and 3' regulatory sequences. They can also include a selectable marker as described to select for host cells containing the expression vector. Such plant expression vectors also contain a promoter regulatory region (e.g., a regulatory region controlling inducible or constitutive, environmentally or developmentally regulated, or cell- or tissue-specific expression), a transcription initiation start site, a ribosome binding site, an RNA processing signal, a transcription termination site, and a polyadenylation signal. Other sequences of bacterial origin are also included to allow the vector to be cloned in a bacterial host. The vector will also typically contain a broad host range prokaryotic origin of replication. In a particularly preferred embodiment, the host cell is a plant cell and the plant expression vector comprises a promoter region as disclosed in SEQ ID NOS: 79-98, an operably linked transcribable sequence, and a transcription termination sequence. Other regulatory sequences envisioned as genetic components in an expression vector include, but is not limited to, non-translated leader sequence that can be coupled with the promoter. Plant expression vectors also can comprise additional sequences including but not limited to restriction enzyme sites that are useful for cloning purposes.

A number of promoters have utility for plant gene expression for any gene of interest including but not limited to selectable markers, scorable markers, genes for pest tolerance, disease tolerance, nutritional enhancements and any other gene that confers a desirable trait or characteristic. Examples of constitutive promoters useful for plant gene expression include, but are not limited to, the cauliflower mosaic virus (CaMV) 35S promoter, which confers constitutive, high-level expression in most plant tissues (see, e.g., Odel et al., Nature 313:810, 1985), including monocots (see, e.g., Dekeyser et al., Plant Cell 2:591, 1990; Terada and Shimamoto, Mol. Gen. Genet. 220:389, 1990); the nopaline synthase promoter (An et al., Plant Physiol. 88:547, 1988); the octopine synthase promoter (Fromm et al., Plant Cell 1:977, 1989); and the figwort mosaic virus (FMV) promoter as described in U.S. Pat. No. 5,378,619.

A variety of plant gene promoters that are regulated in response to environmental, hormonal, chemical, and/or developmental signals can be used for expression of an operably linked gene in plant cells, including promoters regulated by (1) heat (Callis et al., Plant Physiol. 88:965, 1988), (2) light (e.g., pea rbcS-3A promoter, Kuhlemeier et al., Plant Cell 1:471, 1989; maize rbcS promoter, Schaffner and Sheen, Plant Cell 3:997, 1991; or chlorophyll a/b-binding protein promoter, Simpson et al., EMBO J. 4:2723, 1985), (3) hormones, such as abscisic acid (Marcotte et al., Plant Cell 1:969, 1989), (4) wounding (e.g., wunI, Siebertz et al., Plant Cell 1:961, 1989); or (5) chemicals such as methyl jasmonate, salicylic acid, or safener. It may also be advantageous to employ (6) organ-specific promoters (e.g., Roshal et al., EMBO J. 6:1155, 1987; Schernthaner et al., EMBO J. 7:1249, 1988; Bustos et al., Plant Cell 1:839, 1989). The promoters of the present invention are plant promoters that are capable of transcribing operably linked DNA sequences in male reproductive tissues and can be operably linked to any gene of interest in an expression vector.

Plant expression vectors can include RNA processing signals, e.g., introns, which may be positioned upstream or downstream of a polypeptide-encoding sequence in the transgene. In addition, the expression vectors may include additional regulatory sequences from the 3'-untranslated region of plant genes (Thornburg et al., Proc. Natl. Acad. Sci. USA 84:744, 1987; An et al., Plant Cell 1:115, 1989), e.g., a 3' terminator region to increase mRNA stability of the mRNA, such as the PI-II terminator region of potato or the octopine or nopaline synthase 3' terminator regions. Five-end non-translated regions of a mRNA can play an important role in translation initiation and can also be a genetic component in a plant expression vector. For example, non-translated 5' leader sequences derived from heat shock protein genes have been demonstrated to enhance gene expression in plants (see, for example U.S. Pat. No. 5,362,865). These additional upstream and downstream regulatory sequences may be derived from a source that is native or heterologous with respect to the other elements present on the expression vector.

The promoter sequences of the present invention are used to control gene expression in plant cells. The disclosed promoter sequences are genetic components that are part of vectors used in plant transformation. The promoter sequences of the present invention can be used with any suitable plant transformation plasmid or vector containing a selectable or screenable marker and associated regulatory elements, as described, along with one or more nucleic acids expressed in a manner sufficient to confer a particular desirable trait. Examples of suitable structural genes of agronomic interest envisioned by the present invention would include but are not limited to one or more genes for insect tolerance, such as a B.t., pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, fertilizer, growth, development, morphology or plant product(s).

Alternatively, the DNA coding sequences can effect these phenotypes by encoding a non-translatable RNA molecule that causes the targeted inhibition of expression of an endogenous gene, for example via antisense- or cosuppression-mediated mechanisms (see, for example, Bird et al., Biotech. Gen. Engin. Rev. 9:207, 1991). The RNA could also be a catalytic RNA molecule (i.e., a ribozyme) engineered to cleave a desired endogenous mRNA product (see for example, Gibson and Shillitoe, Mol. Biotech. 7:125, 1997). Thus, any gene that produces a protein or mRNA that expresses a phenotype or morphology change of interest is useful for the practice of the present invention.

In addition to regulatory elements or sequences located upstream (5') or within a DNA sequence, there are downstream (3') sequences that affect gene expression and thus the term regulatory sequence as used herein refers to any nucleotide sequence located upstream, within, or downstream to a DNA sequence that controls, mediates, or affects expression of a gene product in conjunction with the protein synthetic apparatus of the cell.

The promoter sequences of the present invention may be modified, for example for expression in other plant systems. In another approach, novel hybrid promoters can be designed or engineered by a number of methods. Many promoters contain upstream sequences that activate, enhance or define the strength and/or specificity of the promoter (Atchison, Ann. Rev. Cell Biol. 4:127, 1988). T-DNA genes, for example, contain "TATA" boxes defining the site of transcription initiation and other upstream elements located upstream of the transcription initiation site modulate transcription levels (Gelvin, In: Transgenic Plants, Kung and Us, eds, San Diego: Academic Press, pp. 49-87, 1988). Ni and colleagues combined a trimer of the octopine synthase (ocs) activator to the mannopine synthase (mas) activator plus promoter and reported an increase in expression of a reporter gene (Ni et al., The Plant Journal 7:661, 1995). The upstream regulatory sequences of the present invention can be used for the construction of such chimeric or hybrid promoters. Methods for construction of variant promoters of the present invention include but are not limited to combining control elements of different promoters or duplicating portions or regions of a promoter (see for example U.S. Pat. No. 5,110,732 and U.S. Pat. No. 5,097,025). Those of skill in the art are familiar with the standard resource materials that describe specific conditions and procedures for the construction, manipulation and isolation of macromolecules (e.g., DNA molecules, plasmids, etc.), generation of recombinant organisms and the screening and isolation of genes, (see for example Sambrook et al., Molecular Cloning: A Laboratory Manual, Cold Spring Harbor Press, 1989; Maliga et al., Methods in Plant Molecular Biology, Cold Spring Harbor Press, 1995; Birren et al., Genome Analysis: volume 1, Analyzing DNA, (1997), volume 2, Detecting Genes, (1998), volume 3, Cloning Systems, (1999) volume 4, Mapping Genomes, (1999), Cold Spring Harbor, N.Y.).

The promoter sequences of the present invention may be incorporated into an expression vector using screenable or scorable markers as described and tested in transient analyses that provide an indication of gene expression in stable plant systems. Methods of testing gene expression in transient assays are known to those of skill in the art. Transient expression of marker genes has been reported using a variety of plants, tissues and DNA delivery systems. For example, types of transient analyses can include but are not limited to direct gene delivery via electroporation or particle bombardment of tissues in any transient plant assay using any plant species of interest. Such transient systems would include but are not limited to protoplasts from suspension cultures in wheat (Zhou et al., Plant Cell Reports 12:612. 1993, electroporation of leaf protoplasts of wheat (Sethi et al., J. Crop Sci. 52: 152, 1983; electroporation of protoplast prepared from corn tissue (Sheen, The Plant Cell 3: 225, 1991), or particle bombardment of specific tissues of interest. The present invention encompasses the use of any transient expression system to evaluate regulatory sequences operatively linked to selected reporter genes, marker genes or agronomic genes of interest. Examples of plant tissues envisioned to test in transients via an appropriate delivery system would include, but are not limited to, leaf base tissues, callus, cotyledons, roots, endosperm, embryos, floral tissue, pollen, and epidermal tissue.

Any scorable or screenable marker can be used in a transient assay. Preferred marker genes for transient analyses of the promoters or 5' regulatory sequences of the present invention include a GUS gene or a GFP gene. The expression vectors containing the 5' regulatory sequences operably linked to a marker gene are delivered to the tissues and the tissues are analyzed by the appropriate mechanism, depending on the marker. The quantitative or qualitative analyses are used as a tool to evaluate the potential expression profile of the 5' regulatory sequences when operatively linked to genes of agronomic interest in stable plants. Ultimately, the 5' regulatory sequences of the present invention are directly incorporated into suitable plant transformation expression vectors comprising the 5' regulatory sequences operatively linked to a transcribable DNA sequence interest, transformed into plants and the stably transformed plants and progeny thereof analyzed for the desired expression profile conferred by the 5' regulatory sequences.

Those of skill in the art are aware of the vectors suitable for plant transformation. Suitable vectors would include but are not limited to disarmed Ti-plasmids for *Agrobacterium*-mediated methods. These vectors can contain a resistance marker, 1-2 T-DNA borders, and origins of replication for *E. coli* and *Agrobacterium* along with one or more genes of interest and associated regulatory regions. Those of skill in the art are aware that for *Agrobacterium*-mediated approaches a number of strains and methods are available. Such strains would include but are not limited to *Agrobacterium* strains C58, LBA4404, EHA101 and EHA105. Particularly preferred strains are *Agrobacterium tumefaciens* strains. Other DNA delivery systems for plant transformation are also known to those of skill in the art and include, but are not limited to, particle bombardment of selected plant tissues.

Exemplary nucleic acids that may be introduced by the methods encompassed by the present invention include, for example, DNA sequences or genes from another species, or even genes or sequences that originate with or are present in the same species but are incorporated into recipient cells by genetic engineering methods rather than classical reproduction or breeding techniques. However, the term exogenous is also intended to refer to genes that are not normally present in the cell being transformed, or perhaps simply not present in the form, structure, etc., as found in the transforming DNA segment or gene, or genes that are normally present yet which one desires, e.g., to have over-expressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

The plant transformation vectors containing the promoter sequences of the present invention may be introduced into plants by any plant transformation method. Several methods are available for introducing DNA sequences into plant cells and are well known in the art. Suitable methods include but are not limited to bacterial infection, binary bacterial artificial chromosome vectors, direct delivery of DNA (e.g. via PEG-mediated transformation, desiccation/inhibition-mediated DNA uptake, electroporation, agitation with silicon carbide fibers), and acceleration of DNA coated particles (reviewed in Potrykus, Ann. Rev. Plant Physiol. Plant Mol. Biol., 42: 205, 1991).

Methods for specifically transforming dicots primarily use *Agrobacterium tumefaciens*. For example, transgenic plants reported include but are not limited to cotton (U.S. Pat. No. 5,004,863; U.S. Pat. No. 5,159,135; U.S. Pat. No. 5,518,908, WO 97/43430), soybean (U.S. Pat. No. 5,569,834; U.S. Pat. No. 5,416,011; McCabe et al., Bio/Technology, 6:923, 1988; Christou et al., Plant Physiol., 87:671, 1988); *Brassica* (U.S. Pat. No. 5,463,174), and peanut (Cheng et al., Plant Cell Rep., 15: 653, 1996).

Similar methods have been reported in the transformation of monocots. Transformation and plant regeneration using these methods have been described for a number of crops including but not limited to asparagus (*Asparagus officinalis*; Bytebier et al., Proc. Natl. Acad. Sci. U.S.A., 84: 5345, 1987); barley (*Hordeum vulgarae*; Wan and Lemaux, Plant Physiol., 104: 37, 1994); maize (*Zea mays*; Rhodes et al., Science, 240: 204, 1988; Gordon-Kamm et al., Plant Cell, 2: 603, 1990; Fromm et al., Bio/Technology, 8: 833, 1990; Koziel et al., Bio/Technology, 11: 194, 1993); oats (*Avena sativa*; Somers et al., Bio/Technology, 10: 1589, 1992); orchardgrass (*Dactylis glomerata*; Horn et al., Plant Cell Rep., 7: 469, 1988); rice (*Oryza sativa*, including indica and japonica varieties, Toriyama et al., Bio/Technology, 6: 10, 1988; Zhang et al., Plant Cell Rep., 7: 379, 1988; Luo and Wu, Plant Mol. Biol. Rep., 6: 165, 1988; Zhang and Wu, Theor. Appl. Genet., 76: 835, 1988; Christou et al., Bio/Technology, 9: 957, 1991); sorghum (*Sorghum bicolor*; Casas et al., Proc. Natl. Acad. Sci. U.S.A., 90: 11212, 1993); sugar cane (*Saccharum* spp.; Bower and Birch, Plant J., 2: 409, 1992); tall fescue (*Festuca arundinacea*; Wang et al., Bio/Technology, 10: 691, 1992); turfgrass (*Agrostis palustris*; Zhong et al., Plant Cell Rep., 13: 1, 1993); wheat (*Triticum aestivum*; Vasil et al., Bio/Technology, 10: 667, 1992; Weeks et al., Plant Physiol., 102: 1077, 1993; Becker et al., Plant, J. 5: 299, 1994), and alfalfa (Masoud et al., Transgen. Res., 5: 313, 1996). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoter sequences of the present invention. Those of skill in the art are aware of the numerous methods available for the analysis of transformed plants. A variety of methods are used to assess gene expression and determine if the introduced gene(s) is integrated, functioning properly, and inherited as expected. For the present invention the promoters can be evaluated by determining the expression levels of genes to which the promoters are operatively linked. A preliminary assessment of promoter function can be determined by a transient assay method using reporter genes, but a more definitive promoter assessment can be determined from the analysis of stable plants. Methods for plant analysis include but are not limited to Southern blots or northern blots, PCR-based approaches, biochemical analyses, phenotypic screening methods, field evaluations, and immunodiagnostic assays.

The methods of the present invention including but not limited to cDNA library preparation, genomic library preparation, sequencing, sequence analyses, PCR technologies, vector construction, transient assays, and plant transformation methods are well known to those of skill in the art and are carried out using standard techniques or modifications thereof.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Plant Material DNA Isolation and Library Construction

The target cDNA libraries included three tassel libraries. The background cDNA libraries included cDNA libraries prepared from leaf; root, embryo, callus, shoot, seedling, endosperm, culm, ear, and silks.

Plant Growth Conditions

Seeds are planted at a depth of about 3 cm in soil into 2"-3" pots containing Metro 200 growing medium and transplanted into larger 10" pots containing the same soil after 2-3 weeks. Plants were fertilized as needed. A total of about 900 mg Fe is added to each pot. Corn plants are grown in the greenhouse in 15 hr day/9 hr night cycles. The daytime temperature is 26.7° C. and the night temperature is 21.1° C. Lighting is provided by 1000 W sodium vapor lamps.

Tissue Isolation

The corn immature tassel cDNA library (SATMON001) is generated using maize (B73, Illinois Foundation Seeds, Champaign, Ill. U.S.A.). The corn plant is at the V6 plant developmental stage. The tassel is an immature tassel 2-3 cm in length. The immature tassel is frozen in liquid nitrogen and the harvested tissue is stored at −80° C. until the RNA is prepared.

The corn immature tassel cDNA library (SATMON021) is generated using maize (DK604, Dekalb Genetics, Dekalb Ill., U.S.A.). The corn plant is at the V8 plant developmental stage. The tassels, which are about 15-20 cm in length, are collected and frozen in liquid nitrogen. The harvested tissue is stored at −80° C. until the RNA is prepared.

The corn immature tassel cDNA library (SATMON024) containing tassel with glume, anthers, and pollen is generated using maize (DK604, Dekalb Genetics, Dekalb, Ill. U.S. A.). The corn plant is at the V9 plant developmental stage. The tassel is at the rapidly developing stage, and a tassel about 37 cm along with the glume, anthers, and pollen are collected and frozen in liquid nitrogen. The harvested tissue is stored at −80° C. until the RNA is prepared.

The RNA is purified using Trizol reagent available from Life Technologies (Gaithersburg, Md.) essentially as recommended by the manufacturer. Poly A+ RNA (mRNA) is purified using magnetic oligo dT beads essentially as recommended by the manufacturer (Dynabeads, Dynal Corporation, Lake Success, N.Y.). Two modifications to the Trizol protocol include centrifuging the ground tissue samples at 12,000×g for 10 minutes at 4° C. after the addition of Trizol to remove insoluble material, and precipitating the RNA with 0.25 mL isopropanol and 0.25 mL 0.8M NaCl per 1.0 mL Trizol used. All the samples are precipitated with 0.1 volume of 3M NaOAc and 3.0 volumes of ethanol. RNAs are resuspended in distilled water at a concentration of 2 µg/µL. The RNAs are DNase treated for 10 minutes at room temperature with RNase free DNase (BMB, Indianapolis, Ind.) and samples are extracted with phenol/chloroform and isopropanol precipitated as described, and resuspended in distilled water at a concentration of 1 µg/µL.

Construction of cDNA libraries is well-known in the art and a number of cloning strategies exist. A number of cDNA library construction kits are commercially available. The Superscript™ Plasmid System for cDNA synthesis and Plasmid Cloning (Gibco BRL, Life Technologies, Gaithersburg, Md.) is used, following the conditions suggested by the manufacturer.

The cDNA libraries are plated on LB agar containing the appropriate antibiotics for selection and incubated at 37° C. for a sufficient time to allow the growth of individual colonies. Single colonies are individually placed in each well of a 96-well microtiter plate containing LB liquid including selective antibiotics. The plates are incubated overnight at approximately 37° C. with gentle shaking to promote growth of the cultures. The plasmid DNA is isolated from each clone using Qiaprep Plasmid Isolation kits, using the conditions recommended by the manufacturer (Qiagen Inc., Santa Clara, Calif.).

Template plasmid DNA clones are used for subsequent sequencing. For sequencing, the ABI PRISM dRhodamine Terminator Cycle Sequencing Ready Reaction Kit with AmpliTaq® DNA Polymerase, FS, is used (PE Applied Biosystems, Foster City, Calif.).

After cDNA synthesis, the samples are diluted with one volume of water, and one microliter is used for each tissue-specificity PCR assay. Corn cDNAs were synthesized for tissue specificity testing methods well known in the art include leaf, root, rachus, early anther, kernals from 6 cm ear, kernals from 4 cm ears, silk, glumme/lemma/palea, mature anther and pollen, meristem, microspores, culm, tassel, ear, and husk.

Example 2

Promoter Lead Identification

The database of EST sequences derived from the cDNA libraries prepared from various corn tissues is used to identify the genes with the correct expression profile from which promoter candidates can be isolated for expression of operably linked DNA sequences in male reproductive tissues. The sequences are also used as query sequences against GenBank databases that contain previously identified and annotated sequences and searched for regions of homology using BLAST programs. The selection of expressed sequence tags (ESTs) for subsequent promoter isolation is reflective of the presence of one or more sequences among the representative ESTs from a random sampling of an individual cDNA library or collection of cDNA libraries. To identify regulatory sequences that regulate the expression of transcripts in the target tissues of interest from EST sequences in the database, a subsetting function is done, requesting ESTs found in target libraries such as the three tassel libraries and EST clones in all other libraries were subtracted. The background or non-target libraries included the following: SATMON013 (corn meristem), SATMON020 (corn callus), SATMON022 (corn immature ear), SATMON023 (corn ear, growing silks), SATMON025 (corn regenerating callus), SATMON004 (corn leaf), SATMON009 (corn leaf, V8 stage), SATMON011 (corn leaf, undeveloped), SATMON016 (corn sheath), SATMON026 (corn leaf), SATMON027 (corn leaf, water stressed 6 days), SATMON031 (corn leaf V4 stage), SATMONN01 (corn leaf normalize), SATMON003 (corn root), SATMON007 (corn primary root), SATMON010 (corn root V8 stage), SATMON028 (corn root, water stressed 6 days), SATMON030 (corn root V4 stage), SATMONN05 (corn root, normalize), SATMON014 (corn endosperm, 14 days after pollination), SATMON017 (corn embryo, 21 days after pollination), SATMON033 (corn embryo, 13 days after pollination), SATMON036 (corn endosperm 22 days after pollination), SATMONN04 (corn embryo, 21-DAP, normalized), SATMONN06 (corn embryo, 21-DAP, normalized), SATMON008 (corn primary shoot), SATMON012 (corn seedling, 2 days post-germination), SATMON019 (corn culm), SATMON029 (corn seedling, etiolated 4 days), and SATMON034 (corn seedling, cold stressed). The cDNA clones identified from the subsetting are candidates for tissue-enhanced/specific genes and are further pursued. Rt-PCR reactions are performed for each of the leads to determine if a male-specific/enhanced pattern of expression is observed. The EST sequences that were detectable predominantly in male tissues are used to isolate the tissue enhanced/specific promoters.

Table 1 provides background clone ID (EST) information and GenBank identifier (gi) information for the ESTs used for subsequent isolation of the promoter sequences of SEQ ID NOS: 79-98. The promoter leads were all obtained from the SATMON024 library source as described above. Sequence annotation is listed for the clone IDs based on a GenBank BLAST search with a p-value cut-off of $10^{-8}$. The information is subject to change as new sequences are submitted to the sequence databases. The annotations for the ESTs are listed as follows with the annotation information in parentheses: Clone ID 700352826); Clone ID 700353038 (*Cynodon dactylon* calcium-binding pollen allergen gene, partial cds; p value 7e -53); Clone ID 700354918 (*Phleum pratense* mRNA for polygalacturonase, partial: p-value 1e -08); Clone ID 700353844 (*Z. mays* pollen specific mRNA C-terminal (clone 4H7) p-value 6e -26); Clone ID 700355306 (*Holcus lanatus* mRNA for major group I allergen Hol 1 1; p-value 1e-21)); Clone ID 700353142); Clone ID 700282503); Clone ID 700282409 (*Z. mays* ZmPRO1 mRNA for profilin 1; p value 2e-34); Clone ID 700352616); Clone ID 700354681 (*Z. mays* ZmPRO2 mRNA for profilin 2; p-value e-137); 700353007); 700352625); and Clone ID 700382630 (*Z. mays* mRNA for pectin methylesterase-like protein; p value 1e-08).

TABLE 1

Promoter Summary Information

| Clone ID | SEQ ID NO. | GenBank Identifier (gi) |
|---|---|---|
| 700352826 | 79 | none |
| 700353038 | 80, 81 | g1864023 |
| 700354918 | 82 | aj238848 |
| 700353844 | 83 | x57275 |
| 700355306 | 84 | aj012714 |
| 700353142 | 85 | none |
| 700282503 | 86 | none |
| 700282409 | 87 | x73279 |
| 700282409 | 88 | x73279 |
| 700352616 | 89 | none |
| 700354681 | 90 | x73280 |
| 700353007 | 91 | none |
| 700352625 | 92 | none |
| 700382630 | 93 | y13285 |
| 700352826 | 94 | none |
| 700353038 | 95, 96, 97, 98 | g1864023 |

Example 3

Genomic Library Construction PCR Amplification and Promoter Isolation

A number of methods are known to those of skill in the art for genomic library preparation. For genomic libraries of the present invention, corn DNA (Maize hybrid Fr27 X FrMo17) is isolated by a CsCl purification protocol according to Ausubel et al. (1992) or by a CTAB purification method (Rogers and Bendich, Plant Mol. Biol., 5:69, 1988). Reagents are available commercially (see, for example Sigma Chemical Co., St. Louis, Mo.). The libraries are prepared according to manufacturer instructions (GENOME WALKER, a trademark of CLONTECH Laboratories, Inc, Palo Alto, Calif.). In separate reactions, genomic DNA is subjected to restriction enzyme digestion overnight at 37° C. with the following blunt-end endonucleases: EcoRV, ScaI, DraI, PvuII, or StuI (CLONTECH Laboratories, Inc., Palo Alto, Calif.). The reaction mixtures are extracted with phenol:chloroform, ethanol precipitated, and resuspended in Tris-EDTA buffer. The purified blunt-ended genomic DNA fragments are then ligated to the GenomeWalker™ adaptors and ligation of the resulting DNA fragments to adaptors were done according to manufacturer protocol. The GenomeWalker™ sublibraries are aliquoted and stored at −20° C.

Genomic DNA ligated to the GenomeWalker™ adaptor (above) is subjected to a primary round of PCR amplification with gene-specific primer 1 (GSP1) and a primer that anneals to the Adaptor sequence, adaptor primer 1 (AP1) (SEQ ID NO:1). A diluted (1:50) aliquot of the primary PCR reaction is used as the input DNA for a nested round of PCR amplification with gene-specific primer 2 (GSP2) and adaptor primer 2 (AP2) (SEQ ID NO:2), or adaptor primer 3 (AP3) (SEQ ID NO:3). The annealing temperatures of the GenomeWalker™ primary primer (AP1) and nested primer (AP2) are 59° C. and 71° C., respectively. Generally, gene specific primers are designed to have the following characteristics: 26-30 nucleotides in length, GC content of 40-60% with resulting temperatures for most of the gene specific primers in the high 60° C. range or about 70° C. The Taq polymerase used is Amplitaq Gold™ or Expand HiFidelity (Boehringer Mannheim) available through Perkin-Elmer Biosystems (Branchbury, N.J.). A number of temperature cycling instruments and reagent kits are commercially available for performing PCR experiments and include those available from PE Biosystems (Foster City, Calif.), Stratagene (La Jolla, Calif.), and MJ Research Inc. (Watertown, Mass.). Following the primary PCR reaction, an aliquot is taken (10-15 μL) for agarose gel analysis. Isolation of each unknown sequence required amplification from 5 sub-genomic libraries and a negative control (without DNA).

The PCR components and conditions generally used are outlined below:

PRIMARY PCR

| Component | Amount/Volume reciuired |
|---|---|
| Sub-library aliquot | 1 μL |
| Gene-specific primer 1 | 1 μL (100 pmol) |
| GenomeWalker ™ Adaptor primer 1 (AP1) | 1 μL |
| dNTP mix (10 mM of each dNTP) | 1 μL |
| DMSO | 2.5 μL (or 2–5% final concentration) |
| 10X PCR buffer (containing MgCl$_2$) | 5 μL (final concentration of 1X) |
| Amplitaq Gold ™ or Expand HiFidelity | 0.5 μL |
| Distilled Water | For final reaction volume of 50 μL |

Reaction Conditions for Primary PCR:

A. 1 minutes at 95° C.

B. 94° C. for 2 seconds, 70° C. for 3 minutes; repeat 94° C./70° C. cycling for total of 7 times C. 94° C. for 2 seconds, 65° C. for 3 minutes; repeat 94° C./65° C. cycling for total of 36 times D. 65° C. for 4 minutes as a final extension E. 10° C. for an extended incubation NESTED PCR (secondary PCR reaction)

| Component | Amount/Volume Required |
|---|---|
| 1:50 dilution of the primary PCR reaction | 1 μL |
| Gene-specific primer 2 | 1 μL (100 pmol) |
| GenomeWalker ™ Adaptor primer 2 or 3 (AP2 or AP3)) | 1 μL |
| dNTP mix (10 mM of each dNTP) | 1 μL |
| DMSO | 2.5 μL |
| 10X PCR buffer (containing MgCl$_2$) | 5 μL (final concentration of 1X) |
| Amplitaq Gold ™ | 0.5 μL |
| Distilled water | to final reaction volume of 50 μL |

Reaction Conditions for Nested PCR:

A. 1 minutes at 95° C.

B. 94° C. for 2 seconds, 70° C. for 3 minutes; repeat 94° C./70° C. cycling for total of 5 times C. 94° C. for 2 seconds, 65° C. for 3 minutes; repeat 94° C./65° C. cycling for total of 24 times D. 65° C. for 4 minutes as a final extension E. 10° C. for an extended incubation For RT-PCR the corn inbred line H99 is used and the generic PCR reaction conditions are outlined below:

1 uL cDNA 5 uL 10×BMB PCR reaction buffer (supplied with taq DNA polymerase)

1 uL 10 mM dNTPs 1 uL 10 uM primer 1

1 uL 10 uM primer 2

0.5 uL taq DNA polymerase (BMB, Indianapolis, Ind.)

40.5 uL H2O 1 uL DMSO (optional)

3a. 700353038 Clone ID Analysis and Promoter Isolation

To determine the distribution of the clone ID 700353038 transcripts in corn, RT-PCR is performed using the SEQ ID NO:4 and SEQ ID NO:5 primers following a standard RT-PCR protocol using cDNA derived from anther, 6 cm ear, glume/lemma/palea, husk, kernel from 4 cm ears, leaf, meristem, mature anther/pollen, microspores, rachis, root, or silk. Taq DNA polymerase from BMB (Indianapolis, Ind.) is used in combination with the supplied reaction buffer. Cycling parameters are as follows: 94° C. 1 minute and 35 cycles of 94° C. 5 seconds, 52° C. 30 seconds and 72° C. 30 seconds. PCR products are amplified for this clone using cDNA derived from anther, glume/lemma/palea, microspores, and pollen but not with cDNA derived from ear, husk, kernel, meristem, rachis, leaf, root, or silk.

For the isolation of the clone ID 700353038 promoter, SEQ ID NO:14 is used in combination with SEQ ID NO:1 in a standard GenomeWalker™ PCR reaction with the following conditions: Expand Hi Fidelity DNA Polymerase (BMB Indianapolis, Ind.) is used in conjunction with the supplied buffer #2, 2 μL of a 1:2 dilution of GenomeWalker™ libraries made according to the manufacturer's protocol (Clontech, Palo Alto, Calif.) and made with maize genomic DNA. The following cycling parameters are used: 94° C. 1 minute, 7 cycles of 94° C. 4 seconds, 70° C. 3 min, and 33 cycles 94° C. 4 seconds, 68° C. 3 minutes. For the nested, secondary PCR reaction, 1 μL of the primary reaction was used with SEQ ID No: 15 and SEQ ID NO: 3 (AP3) in a standard GenomeWalker™ PCR reaction using Expand Hi Fidelity DNA Polymerase (BMB Indianapolis, Ind.) with the supplied buffer #2. The reactions are carried out under the following cycling conditions: 94° C. 1 minute, 5 cycles of 94° C. 4 seconds, 72° C. 3 minutes, and cycles of 94° C. 4 seconds and 67° C. 3 minutes.

Twenty five microliters of the secondary PCR reaction is analyzed by agarose gel electrophoresis, and bands of approximately 900 bp and 800 bp are cut out, purified using the Qiaquick gel extraction kit (Qiagen, Valencia, Calif.) and eluted with 30 μL 10 mM Tris pH. 8.5. Five microliters of the purified band is ligated to 50 ng of pGEM-T-Easy vector (Promega, Madison, Wis.). DNA from individual clones are isolated using the Qiagen Plasmid Mini kit (Qiagen, Valencia, Calif.) and sequenced using the M13 forward primers and M13 reverse primers. Sequence analysis indicated the two fragments shared 3' homology but diverged at their 5' end. The promoter sequences are shown in SEQ ID NO:80 and SEQ ID NO: 81.

To determine if the large open reading frames identified in the isolated genomic fragments are transcribed, RT-PCR is performed using the following primer pairs: 1. SEQ ID NOS:6 and 7; 2. SEQ ID NOS:8 and 9; 3. SEQ ID NOS:10 and 11; and 4. SEQ ID NOS:12 and 13. RT-PCR is performed using a standard RT-PCR protocol using cDNA derived from anther, 6 cm ear, glume/lemma/palea, husk, kernel from 4 cm ears, leaf, meristem, mature anther/pollen, microspores, rachis, root, or silk. Taq DNA polymerase from BMB (Indianapolis, Ind.) is used in combination with the supplied reaction buffer. Cycling parameters are as follows: 94° C. 1 minute and 35 cycles of 94° C. 5 seconds, 52° C. 30 seconds and 72° C. 30 seconds.

Two "ATG" sequences are identified, in frame with an ORF in the EST sequence. Primers are designed to the sequences 5' to each of these putative start codons (SEQ ID NO:16 and SEQ ID NO:17). To isolate the promoter fragment and 5' leader sequence by PCR, the SEQ ID NO:16 primer and the SEQ ID NO:17 primer are separately used with the AP3 primer (SEQ ID NO:3) in a standard PCR reaction containing 1 μL of DNA from either the 800 bp or 900 bp clone ID 700353038 promoter fragment, using 0.5 uL BMB taq polymerase and the supplied buffer. The cycling parameters are as follows: 94° C. 1 minute, 20 cycles of 94° C. 5 seconds 55° C. 15 seconds and 72° C. 30 seconds.

The amplified promoter fragments are analyzed by agarose gel electrophoresis, and bands of approximately 850 bp and 750 bp are cut out and purified using the Qiaquick gel extraction kit (Qiagen, Valencia, Calif.) following the conditions recommended by the manufacturer. The resulting bands are designated SEQ ID NOS: 95 and 96 (amplified from SEQ ID NO: 81), and SEQ ID NOS: 97 and 98 (amplified from SEQ ID NO: 80). The fragments are eluted with 30 μL 10 mM Tris pH. 8.5. Five microliter of the purified band is ligated to 50 ng of pGEM-T-Easy vector (Promega, Madison, Wis.). DNA from individual clones is isolated using the Qiagen Plasmid Mini kit (Qiagen, Valencia, Calif.). The DNA is digested with Hind III and Bgl II, and the resulting promoter fragments are analyzed by agarose gel electrophoresis and bands of approximately 850 bp and 750 bp are cut out, purified using the Qiaquick gel extraction kit (Qiagen, Valencia, Calif.) and eluted with 30 μL 10 mM Tris pH. 8.5. Five microliter of the purified band is ligated to 1 μL of an expression vector such as pMON19469 shown in FIG. 1, that is prepared by digesting 10 μg with BglII and HindIII, separating by agarose gel electrophoresis and purified using the Qiaquick gel extraction kit (Qiagen, Valencia, Calif.) and eluted with 30 μL 10 mM Tris pH. 8.5. The resulting plasmids contain the promoter fragments, hsp70 intron, and GUS gene and are used to assay promoter activity of the promoter fragments.

3b. 700352826 Clone ID Analysis and Promoter Isolation

To determine the distribution of the clone ID 700352826 transcripts in corn, RT-PCR was performed using the SEQ ID NO:18 and SEQ ID NO:19 primers following a standard RT-PCR protocol using cDNA derived from anther, 6 cm ear, glume/lemma/palea, husk, kernel from 4 cm ears, leaf, meristem, mature anther/pollen, microspores, rachis, root, and silk. Taq DNA polymerase from BMB (Indianapolis, Ind.) is used in combination with the supplied reaction buffer. Cycling parameters are as follows: 94° C. 1 minute and 35 cycles of 94° C. 5 seconds, 52° C. 30 seconds and 72° C. 30 seconds. PCR products are obtained with cDNA derived from anther, glume/lemma/palea, micropsores, and pollen but not with cDNA derived from ear, husk, kernel, meristem, rachis, leaf, root, or silk.

For the isolation of the clone ID 700352826 promoter, SEQ ID NO:20 is used in combination with SEQ ID NO:1 AP1 in a standard GenomeWalker™ PCR reaction with the following conditions: Expand Hi Fidelity DNA Polymerase (BMB Indianapolis, Ind.) is used in conjunction with the supplied buffer #2, 2 μL of a 1:2 dilution of GenomeWalker™ libraries made according to the manufacturer's protocol (Clontech, Palo Alto, Calif.) and made with maize genomic DNA. The following cycling parameters are used: 94° C. 1 minute, 7 cycles of 94° C. 4 seconds, 70° C. 3 min, and 33 cycles 94° C. 4 seconds, 68° C. 3 minutes. For the nested, secondary PCR reaction, 1 μL of the primary reaction is used with SEQ ID NO:21 and SEQ ID NO:3 (AP3) in a standard GenomeWalker™ PCR reaction using Expand Hi Fidelity DNA Polymerase (BMB Indianapolis, Ind.) with the supplied buffer #2. The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes.

Twenty five microliters of the secondary PCR reaction is analyzed by agarose gel electrophoresis and bands of approximately 500 bp and 3000 bp are cut out, purified using the Qiaquick gel extraction kit (Qiagen, Valencia, Calif.) and eluted with 30 μL 10 mM Tris pH. 8.5. Five microliters of the purified bands is ligated to 50 ng of pGEM-T-Easy vector (Promega, Madison, Wis.). DNA from individual clones is isolated using the Qiagen Plasmid Mini kit (Qiagen, Valencia, Calif.) and is sequenced using M13 forward primers and M13 reverse primers.

The sequence for clone ID 700352826 is derived from a truncated cDNA. A BLAST comparison of the promoter sequence against the GenBank database identified polygalacturase clones that allowed the determination of the translational initiation codon. SEQ ID NO:22 is designed just upstream of the predicted ATG. To isolate the functional promoter fragment and 5' leader sequence by PCR of clone ID 700352826, the SEQ ID NO:22 primer and SEQ ID NO: 3 (AP3) primer are used in a standard PCR reaction containing 1 μL of cloned DNA containing clone ID 700352826 promoter fragment, using BMB taq polymerase and the supplied buffer. The cycling parameters are as follows: 94° C. 1 minute, 20 cycles of 94° C. 5 seconds 55° C. 15 seconds and 72° C. 30 seconds. The sequence of the promoter is SEQ ID NO:79.

The amplified promoter fragments are analyzed by agarose gel electrophoresis and purified using the Qiaquick gel extraction kit (Qiagen, Valencia, Calif.) and eluted with 30 μL 10 mM Tris pH. 8.5 and subsequently cloned into a plasmid as shown in FIG. 1 (pMON19469).

3c. 700354918 Clone Analysis and Promoter Isolation

To determine the distribution of the clone ID 700354918 transcripts in corn, RT-PCR is performed using the SEQ ID NO:23 and SEQ ID NO:24 primers following a standard RT-PCR protocol using cDNA derived from anther, 6 cm ear, glume/lemma/palea, husk, kernel from 4 cm ears, leaf, meristem, mature anther/pollen, microspores, rachis, root, and silk. Taq DNA polymerase from BMB (Indianapolis, Ind.) is used in combination with the supplied reaction buffer. Cycling parameters are as follows: 94° C. 1 minute and 35 cycles of 94° C. 5 seconds, 52° C. 30 seconds and 72° C. 30 seconds. PCR products are produced with cDNA derived from anther, glume/lemma/palea, micropores, and pollen but not with cDNA derived from ear, husk, kernel, meristem, rachis, root, leaf, or silk.

For the isolation of the clone ID 700354918 promoter, SEQ ID NO:25 is used in combination with SEQ ID NO:1 (AP1) in a standard GenomeWalker™ PCR reaction using Expand Hi Fidelity DNA Polymerase (BMB, Indianapolis, Ind.) in conjunction with the supplied buffer #2. Each reaction contains 2 μL of a 1:2 dilution of the GenomeWalker™ libraries made according to the manufacturer's protocol (Clontech, Palo Alto, Calif.) using maize genomic DNA. The following cycling parameters are used: 94° C. 1 minute, 7 cycles of 94° C. 4 seconds, 70° C. 3 min, and 33 cycles 94° C. 4 seconds, 68° C. 3 minutes. For the nested, secondary PCR reaction, 1 μL of the primary reaction is used with SEQ ID NO:26 and SEQ ID NO:3 (AP3) in a standard GenomeWalker™ PCR reaction using Expand Hi Fidelity DNA Polymerase (BMB, Indianapolis, Ind.) with the supplied buffer #2. The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes.

Twenty five microliters of the secondary PCR reaction is analyzed by agarose gel electrophoresis and a 700 bp band is isolated, purified using the Qiaquick gel extraction kit (Qiagen, Valencia, Calif.), and eluted with 30 μL 10 mM Tris pH. 8.5. Five microliters of the purified band is ligated to 50 ng of pGEM-T-Easy vector (Promega, Madison, Wis.). DNA from individual clones is isolated using the Qiagen Plasmid Mini kit (Qiagen, Valencia, Calif.) and sequenced using the M13 forward primers and M13 reverse primers.

The clone ID 700354918 sequence is derived from a truncated cDNA and the translation initiation codon was unknown. A BLAST of the 5' end of the promoter against the GenBank database produced polygalacturase clones that allowed the prediction of the translational initiation codon 67 nucleotides from the 5' end of promoter. To isolate the functional promoter fragment and 5' leader sequence of clone ID 700354918 by PCR, SEQ ID NO:27 is used in combination with SEQ ID NO: 1 (AP1) in a standard GenomeWalker™ PCR reaction using Expand Hi Fidelity DNA Polymerase (BMB, Indianapolis, Ind.) in conjunction with the supplied buffer #2. Each reaction contains 2 μL of a 1:2 dilution of GenomeWalker™ libraries made according to the manufacturer's protocol (Clontech, Palo Alto, Calif.) and made with maize genomic DNA. The following cycling parameters are used: 94° C. 1 minute, 7 cycles of 94° C. 4 seconds, 70° C. 3 min, and 33 cycles 94° C. 4 seconds, 68° C. 3 minutes. For the nested, secondary PCR reaction, 1 μL of the primary reaction is used with SEQ ID NO:28 and SEQ ID NO:3 (AP3) in a standard GenomeWalker™ PCR reaction using Expand Hi Fidelity DNA Polymerase (BMB, Indianapolis, Ind.) with the supplied buffer #2. The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes.

The PCR products are purified by gel electrophoresis as described and cloned into a vector such as shown in FIG. 1 (pMON19469). The promoter sequence is shown in SEQ ID NO:82.

3d. 700353844 Clone Analysis and Promoter Isolation

To determine the distribution of the clone ID 700353844 transcripts in corn, RT-PCR is performed using the SEQ ID NO:29 and SEQ ID NO:30 primers following a standard RT-PCR protocol using cDNA derived from anther, 6 cm ear, glume/lemma/palea, husk, kernel from 4 cm ears, leaf, meristem, mature anther/pollen, microspores, rachis, root, and silk. Taq DNA polymerase from BMB (Indianapolis, Ind.) is used in combination with the supplied reaction buffer. Cycling parameters are as follows: 94° C. 1 minute and 35 cycles of 94° C. 5 seconds, 52° C. 30 seconds and 72° C. 30 seconds. PCR products are obtained with cDNA derived from anther, glume/lemma/palea, micropsores, and pollen but not with cDNA derived from ear, husk, kernel, meristem, rachis, leaf, root, or silk.

For the isolation of the clone ID 700353844 promoter, SEQ ID NO:31 is used in combination with SEQ ID NO:1 (AP 1) in a standard GenomeWalker™PCR reaction using Expand Hi Fidelity DNA Polymerase (BMB, Indianapolis, Ind.) in conjunction with the supplied buffer #2. Each reaction contains 2 μL of a 1:2 dilution of the Genome Walker libraries made according to the manufacturer's protocol (Clontech, Palo Alto, Calif.) using maize genomic DNA. The following cycling parameters are used: 94° C. 1 minute, 7 cycles of 94° C. 4 seconds, 70° C. 3 min, and 33 cycles 94° C. 4 seconds, 68° C. 3 minutes. For the nested, secondary PCR reaction, 1 μL of the primary reaction is used with SEQ ID NO:32 and SEQ ID NO:3 (AP3) in a standard GenomeWalker™ PCR reaction using Expand Hi Fidelity DNA Polymerase (BMB Indianapolis, Ind.) with the supplied buffer #2. The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes.

Twenty five microliters of the secondary PCR reaction is analyzed by agarose gel electrophoresis and a 500 bp band is isolated, purified using the Qiaquick gel extraction kit (Qiagen, Valencia, Calif.) and eluted with 30 μL 10 mM Tris pH. 8.5. Five microliters of the purified band is ligated to 50 ng of pGEM-T-Easy vector (Promega, Madison, Wis.). DNA from 2 individual clones is isolated using the Qiagen Plasmid Mini kit (Qiagen, Valencia, Calif.) and sequenced using the M13 forward primers and M13 reverse primers. The sequence of the promoter fragment is shown in SEQ ID NO:83. The promoter fragment is subsequently cloned into a plasmid as shown in FIG. 1 (pMON19469).

3e. 700355306b Clone Analysis and Promoter Isolation

To determine the distribution of the clone ID 700355306b transcripts in corn, RT-PCR is performed using the SEQ ID NO:33 and SEQ ID NO:34 primers following a standard RT-PCR protocol using cDNA derived from anther, 6 cm ear, glume/lemma/palea, husk, kernel from 4 cm ears, leaf, meristem, mature anther/pollen, microspores, rachis, root, and silk. Taq DNA polymerase from BMB (Indianapolis, Ind.) is used in combination with the supplied reaction buffer. Cycling parameters are as follows: 95° C. 1 minute and 35 cycles of 95° C. 15 seconds, 50° C. 30 seconds and 72° C. 30 seconds followed by a 10-minute incubation at 72C. Bands are amplified with cDNA derived from anther, micropsores, and pollen but not with cDNA derived from ear, husk, glume/lemma/palea, kernel, meristem, rachis, leaf, root, or silk.

For the isolation of the clone ID 700355306b promoter, SEQ ID NO:35 is used in combination with SEQ ID NO:1 (AP1) in a standard GenomeWalker™ PCR reaction using Expand Hi Fidelity DNA Polymerase (BMB Indianapolis, Ind.) in conjunction with the supplied buffer #2. Each reaction contains 2 μL of a 1:2 dilution of the GenomeWalker™ libraries made according to the manufacturer's protocol (Clontech, Palo Alto, Calif.) using maize genomic DNA. The following cycling parameters are used: 94° C. 1 minute, 7 cycles of 94° C. 4 seconds, 70° C. 3 min, and 33 cycles 94° C. 4 seconds, 68° C. 3 minutes. For the nested, secondary PCR reaction, 1 μL of the primary reaction is used with SEQ ID NO: 36 and SEQ ID NO:2 (AP2) in a standard GenomeWalker™ PCR reaction using Expand Hi Fidelity DNA Polymerase (BMB, Indianapolis, Ind.) with the supplied buffer #2. The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C.

Twenty five microliters of the secondary PCR reaction is analyzed by agarose gel electrophoresis bands are isolated, purified using the Qiaquick gel extraction kit (Qiagen, Valencia, Calif.), and eluted with 30 μL 10 mM Tris pH. 8.5. To add a HindIII restriction site to the 5' end of the 700355306b promoter fragment, 1 μL of the isolated DNA is amplified under standard GenomeWalker™ PCR conditions using Expand Hi Fidelity DNA Polymerase (BMB, Indianapolis, Ind.) with the supplied buffer #2 in combination with primers SEQ ID NO:37 and SEQ ID NO:3 (AP3). The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C.

Twenty five microliters of the tertiary PCR reaction is analyzed by agarose gel electrophoresis, the promoter band is isolated, purified using the Qiaquick gel extraction kit (Qiagen, Valencia, Calif.) and eluted with 30 μL 10 mM Tris pH. 8.5. Five microliters of the purified band is ligated to 50 ng of pGEM-T-Easy vector (Promega, Madison, Wis.). DNA from individual clones is isolated using the Qiagen Plasmid Mini kit (Qiagen, Valencia, Calif.) and sequenced by the using the M13 forward primers and M13 reverse primers. The sequence of the promoter fragment is SEQ ID NO:84. The promoter fragment is subsequently cloned into a plasmid as shown in FIG. 1 (pMON19469).

3f. 700353142 Clone Analysis and Promoter Isolation

To determine the distribution of the clone ID 700353142 transcripts in corn, RT-PCR is performed using the SEQ ID NO:38 and SEQ ID NO:39 primers following a standard RT-PCR protocol using cDNA derived from anther, 6 cm ear, glume/lemma/palea, husk, kernel from 4 cm ears, leaf, meristem, mature anther/pollen, microspores, rachis, root, and silk. Taq DNA polymerase from BMB (Indianapolis, Ind.) is used in combination with the supplied reaction buffer. Cycling parameters are as follows: 95° C. 1 minute and 35 cycles of 95° C. 15 seconds, 50° C. 30 seconds and 72° C. 30 seconds followed by a 10-minute incubation at 72° C. Bands are amplified with cDNA derived from anther, micropsores, glume/lemma/palea, husk, meristem, and pollen but not with cDNA derived from ear, kernel, rachis, leaf, root, or silk.

For the isolation of the clone ID 700353142 promoter, SEQ ID NO:40 is used in combination with SEQ ID NO:1 (AP1) in a standard GenomeWalker™ PCR reaction using Expand Hi Fidelity DNA Polymerase (BMB, Indianapolis, Ind.) in conjunction with the supplied buffer #2. Each reaction contained 2 μL of a 1:2 dilution of the GenomeWalker™ libraries made according to the manufacturer's protocol (Clontech, Palo Alto, Calif.) using maize genomic DNA. The following cycling parameters are used: 94° C. 1 minute, 7 cycles of 94° C. 4 seconds, 70° C. 3 min, and 33 cycles 94° C. 4 seconds, 68° C. 3 minutes. For the nested, secondary PCR reaction, 1 μL of the primary reaction is used with SEQ ID NO:41 and SEQ ID NO:2 (AP2) in a standard GenomeWalker™ PCR reaction using Expand Hi Fidelity DNA Polymerase (BMB Indianapolis, Ind.) with the supplied buffer #2. The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C.

Twenty five microliters of the secondary PCR reaction is analyzed by agarose gel electrophoresis, and PCR products are isolated, purified using the Qiaquick gel extraction kit (Qiagen, Valencia, Calif. cat # 28704) and eluted with 30 μL 10 mM Tris pH. 8.5. To add a HindIII restriction site to the 5' end of the 700353142 promoter fragment, 1 μL of the isolated DNA is amplified under standard GenomeWalker™ PCR conditions using Expand Hi Fidelity DNA Polymerase (BMB, Indianapolis, Ind.) with the supplied buffer #2 in combination with primers SEQ ID NO:42 and SEQ ID NO:3 (AP3). The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C.

Twenty five microliters of the tertiary PCR reaction is analyzed by agarose gel electrophoresis. The promoter band is isolated, purified using the Qiaquick gel extraction kit (Qiagen, Valencia, Calif.), and eluted with 30 μL 10 mM Tris pH. 8.5. Five microliters of the purified band is ligated to 50 ng of pGEM-T-Easy vector (Promega, Madison, Wis.). DNA from individual clones is isolated using the Qiagen Plasmid Mini kit (Qiagen, Valencia, Calif.) and sequenced using the M13 forward primers and M13 reverse primers. The sequence of the promoter is SEQ ID NO:85

3g. 700282503 Clone Analysis and Promoter Isolation

To determine the distribution of the clone ID 700282503 transcripts in corn, 2 RT-PCR experiments are performed. In one experiment SEQ ID NO: 43 and SEQ ID NO:44 primers are used following a standard RT-PCR protocol using cDNA derived from anther, 6 cm ear, glume/lemma/palea, husk, kernel from 4 cm ears, leaf, meristem, mature anther/pollen, microspores, rachis, root, and silk. Taq DNA polymerase from BMB (Indianapolis, Ind.) is used in combination with the supplied reaction buffer. Cycling parameters are as follows: 95° C. for 1 minute and 35 cycles of 95° C. 15 seconds, 50° C. 30 seconds and 72° C. 30 seconds followed by a 10-minute incubation at 72° C. Bands are amplified with cDNA derived from anther, micropsores, glume/lemma/palea, husk, kernal, and pollen but not with cDNA derived from ear, rachis, leaf, root, meristem, or silk. In the second RT-PCR reaction SEQ ID NO:43 and SEQ ID NO:44 primers are used following a standard RT-PCR protocol using cDNA derived from anther, 6 cm ear, glume/lemma/palea, husk, kernel from 4 cm ears, leaf, meristem, mature anther/pollen, microspores, rachis, root, and silk. Taq DNA polymerase from BMB (Indianapolis, Ind.) is used in combination with the supplied reaction buffer. Cycling parameters, are as follows: 95° C. 1 minute and 35 cycles of 95° C. 15 seconds, 50° C. 30 seconds and 72° C. 30 seconds followed by a 10-minute incubation at 72° C. Bands are amplified with cDNA derived from anther, kernal, and pollen but not with cDNA derived from ear, rachis, leaf, root, glume/lemma/palea, microspore, husk, meristem, or silk.

For the isolation of the clone ID 700282503 promoter, SEQ ID NO:46 is used in combination with SEQ ID NO:1 (AP1) in a standard GenomeWalker™ PCR reaction using Expand Hi Fidelity DNA Polymerase (BMB, Indianapolis, Ind.) in conjunction with the supplied buffer #2. Each reaction contains 2 µl of a 1:2 dilution of the GenomeWalker™ libraries made according to the manufacturer's protocol (Clontech, Palo Alto, Calif.) using maize genomic DNA. The following cycling parameters are used: 94° C. 1 minute, 7 cycles of 94° C. 4 seconds, 70° C. 3 min, and 33 cycles 94° C. 4 seconds, 68° C. 3 minutes. For the nested, secondary PCR reaction, 1 µL of the primary reaction was used with SEQ ID NO:47 and SEQ ID NO:2 (AP2) in a standard GenomeWalker™ PCR reaction using Expand Hi Fidelity DNA Polymerase (BMB, Indianapolis, Ind.) with the supplied buffer #2. The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C.

Twenty five microliters of the secondary PCR reaction was analyzed by agarose gel electrophoresis and PCR products are isolated, purified using the Qiaquick gel extraction kit (Qiagen, Valencia, Calif.) and eluted with 30 µL 10 mM Tris pH. 8.5. To add a HindIII restriction site to the 5' end of the 700282503 promoter fragment, 1 µL of the isolated DNA is amplified under standard Genome Walker™PCR conditions using Expand Hi Fidelity DNA Polymerase (BMB Indianapolis, Ind.) with the supplied buffer #2 in combination with primers SEQ ID NO:48 and SEQ ID No:3 (AP3). The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C.

Twenty five microliters of the tertiary PCR reaction is analyzed by agarose gel electrophoresis. A band is isolated, purified using the Qiaquick gel extraction kit (Qiagen, Valencia, Calif.) and eluted with 30 µL 10 mM Tris pH. 8.5. 5 µL of the purified band is ligated to 50 ng of pGEM-T-Easy vector (Promega, Madison, Wis., Cat. # A1360). DNA from individual clones was isolated using the Qiagen Plasmid Mini kit (Qiagen, Valencia, Calif. Cat. #12125) and sequenced using the M13 forward primers and M13 reverse primers. The sequence of the promoter is SEQ ID NO:86.

3h. 700282409 Clone Analysis and Promoter Isolation (Profilin 2)

To determine the distribution of the clone ID 700282409 transcripts in corn, RT-PCR is performed using the SEQ ID NO:49 and SEQ ID NO:50 primers following a standard RT-PCR protocol using cDNA derived from anther, 6 cm ear, glume/lemma/palea, husk, kernel from 4 cm ears, leaf, meristem, mature anther/pollen, microspores, rachis, root, and silk. Taq DNA polymerase from BMB (Indianapolis, Ind.) is used in combination with the supplied reaction buffer. Cycling parameters are as follows: 95° C. for 1 minute and 35 cycles of 95° C. 15 seconds, 50° C. 30 seconds and 72° C. 30 seconds followed by a 10 minute incubation at 72° C. Bands are amplified with cDNA derived from anther, glume/lemma/palea, meristem, microspore, silk, and pollen but not with cDNA derived from ear, husk, kernel, rachis, leaf, or root.

For the isolation of the clone ID 700282409 promoter, SEQ ID NO:51 is used in combination with SEQ ID NO:1 (AP1) in a standard GenomeWalker™ PCR reaction using Expand Hi Fidelity DNA Polymerase (BMB Indianapolis, Ind.) in conjunction with the supplied buffer #2. Each reaction contains 2 µL of a 1:2 dilution of the GenomeWalker™ libraries made according to the manufacturer's protocol (Clontech, Palo Alto, Calif.) using maize genomic DNA. The following cycling parameters are used: 94° C. 1 minute, 7 cycles of 94° C. 4 seconds, 70° C. 3 min, and 33 cycles 94° C. 4 seconds, 68° C. 3 minutes. For the nested, secondary PCR reaction, 1 µL of the primary reaction is used with SEQ ID NO:52 and SEQ ID No. 2 (AP2.) in a standard GenomeWalker™ PCR reaction using Expand Hi Fidelity DNA Polymerase (BMB, Indianapolis, Ind.) with the supplied buffer #2. The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C.

Twenty five microliters of the secondary PCR reaction is analyzed by agarose gel electrophoresis. The bands are isolated, purified using the Qiaquick gel extraction kit (Qiagen, Valencia, Calif.) and eluted with 30 µL 10 mM Tris pH. 8.5. To add a HindIII restriction site to the 5' end of the 700282409 promoter fragment, 1 µL of the isolated DNA is amplified under standard Genome Walker™ PCR conditions using Expand Hi Fidelity DNA Polymerase (BMB Indianapolis, Ind.) with the supplied buffer #2 in combination with primers SEQ ID NO:53 and SEQ ID NO:3 (AP3). The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C.

Twenty five microliters of the tertiary PCR reaction is analyzed by agarose gel electrophoresis. A band is isolated, purified using the Qiaquick gel extraction kit (Qiagen, Valencia, Calif.) and eluted with 30 µL 10 mM Tris pH. 8.5. Five microliters of the purified band is ligated to 50 ng of pGEM-T-Easy vector (Promega, Madison, Wis.). DNA from individual clones is isolated using the Qiagen Plasmid Mini kit (Qiagen, Valencia, Calif.) and sequenced using the M13 forward primers and M13 reverse primers. The sequence designated profilin 2 is shown in SEQ ID NO:87.

3i. 700282409 Clone Analysis and Promoter Isolation (Profilin 1)

All RT-PCR data for 700282409—profilin 1 is the same as the information for profilin 2 as described in Example 3h.

For the isolation of the clone ID 700282409 promoter, SEQ ID NO:51 is used in combination with SEQ ID NO:1 (AP1) in a standard GenomeWalker™ PCR reaction using Expand Hi Fidelity DNA Polymerase (BMB, Indianapolis, Ind.) in conjunction with the supplied buffer #2. Each reaction contains 1.5 µL of a 1:2 dilution of the GenomeWalker™ libraries made according to the manufacturer's protocol (Clontech, Palo Alto, Calif.) using maize genomic DNA. The following cycling parameters are used: 94° C. 1 minute, 7 cycles of 94° C. 4 seconds, 70° C. 3 min, and 33 cycles 94° C. 4 seconds, 68° C. 3 minutes. For the nested, secondary PCR reaction, 1 µL of the primary reaction is used with SEQ ID NO:54 with SEQ ID No:3 (AP3). The reactions are carried out under the following cycling conditions: 94° C. 1 minute, 5 cycles of 94° C. 4 seconds, 72° C. 3 minutes, and 20 cycles of 94° C. 4 seconds and 67° C. 3 minutes followed by 7 minutes at 67° C.

Twenty five microliters of the tertiary PCR reaction is analyzed by agarose gel electrophoresis. A is isolated, purified using the Qiaquick gel extraction kit (Qiagen, Valencia, Calif.) and eluted with 30 μL 10 mM Tris pH. 8.5. Five microliters of the purified band is ligated to 50 ng of pGEM-T-Easy vector (Promega, Madison, Wis.). DNA from individual clones is isolated using the Qiagen Plasmid Mini kit (Qiagen, Valencia, Calif.) and sequenced using the M13 forward primers and M13 reverse primers. The full length promoter sequence is shown in SEQ ID NO:88.

3j. 700352616 Clone Analysis and Promoter Isolation

To determine the distribution of the clone ID 700352616 transcripts in corn, RT-PCR is performed using the SEQ ID NO:55 and SEQ ID NO:56 primers following a standard RT-PCR protocol using cDNA derived from anther, 6 cm ear, glume/lemma/palea, husk, kernel from 4 cm ears, leaf, meristem, mature anther/pollen, microspores, rachis, root, and silk. Taq DNA polymerase from BMB (Indianapolis, Ind.) is used in combination with the supplied reaction buffer. Cycling parameters are as follows: 95° C. 1 minute and 35 cycles of 95° C. 15 seconds, 50° C. 30 seconds and 72° C. 30 seconds followed by 10 minutes at 72° C. Bands are amplified with cDNA derived from anther, glume/lemma/palea, and microspore but not with cDNA derived from ear, husk, kernel, rachis, leaf, pollen, silk, or root.

For the isolation of the clone ID 700352616 promoter, SEQ ID NO:58 is used in combination with SEQ ID NO:1 (AP1) in a standard Genome Walker PCR reaction using Expand Hi Fidelity DNA Polymerase (BMB, Indianapolis, Ind.) in conjunction with the supplied buffer #2. Each reaction contains 2 μL of a 1:2 dilution of the GenomeWalker™ libraries made according to the manufacturer's protocol (Clontech, Palo Alto, Calif.). The following cycling parameters are used: 94° C. 1 minute, 7 cycles of 94° C. 2 seconds, 72° C. 3 min, and 36 cycles 94° C. 2 seconds, 66° C. 3 minutes followed by a 4-minute incubation at 66° C. For the nested, secondary PCR reaction, 1 μL of a 1:50 dilution of the primary reaction is used with SEQ ID NO:59 and SEQ ID NO:2 (AP2) in a standard GenomeWalker™ PCR reaction using Expand Hi Fidelity DNA Polymerase (BMB Indianapolis, Ind.) with the supplied buffer #2. The reactions are carried out under the following cycling conditions: 94° C. 1 minute, 5 cycles of 94° C. 2 seconds, 72° C. 3 minutes, and 25 cycles of 94° C. 2 seconds and 67° C. 3 minutes followed by 4 minutes at 67° C.

Twenty five microliters of the secondary PCR reaction is analyzed by agarose gel electrophoresis. The bands are isolated, purified using the Qiaquick gel extraction kit (Qiagen, Valencia, Calif.), and eluted with 30 μL ddH2O. Five microliters of the purified band is ligated to 50 ng of pGEM-T-Easy vector (Promega, Madison, Wis.). DNA from individual clones is isolated using the Qiagen Plasmid Mini kit (Qiagen, Valencia, Calif.) and sequenced using the M13 forward primers and M13 reverse primers.

To add a HindIII restriction site to the 5' end and a BamH1 site at the 3' end of the 700352616 promoter fragment, 1 μL of the isolated DNA is amplified under standard Genome Walker™ PCR conditions using Expand Hi Fidelity DNA Polymerase (BMB, Indianapolis, Ind.) with the supplied buffer #2 in combination with primers SEQ ID NO:57 and SEQ ID NO.3 (AP3). The reactions are carried out under the following cycling conditions: 94° C. 1 minute, 3 cycles of 94° C. 2 seconds, 70° C. 3 minutes and 12 cycles 94° C. 2 seconds 67° C. 3 minutes followed by a 4-minute incubation at 67° C. Twenty five microliters of this PCR reaction is analyzed by agarose gel electrophoresis. The bands are isolated, purified using the Qiaquick gel extraction kit (Qiagen, Valencia, Calif.), and eluted with 30 μL ddH2O. Five microliters of the purified band is ligated to 50 ng of pGEM-T-Easy vector (Promega, Madison, Wis.). DNA from individual clones is isolated using the Qiagen Plasmid Mini kit (Qiagen, Valencia, Calif.). The promoter sequence is shown in SEQ ID NO:89.

The promoter is cloned into a plasmid vector such as shown in FIG. 1 (pMON19469).

3k. 700354681 Clone Analysis and Promoter Isolation

To determine the distribution of the clone ID 700354681 transcripts in corn, RT-PCR is performed using the SEQ ID NO:60 and SEQ ID NO:61 primers following a standard RT-PCR protocol using cDNA derived from anther, 6 cm ear, glume/lemma/palea, husk, kernel from 4 cm ears, leaf, meristem, mature anther/pollen, microspores, rachis, root, and silk. Taq DNA polymerase from BMB (Indianapolis, Ind.) is used in combination with the supplied reaction buffer. Cycling parameters are as follows: 95° C. 1 minute and 35 cycles of 95° C. 15 seconds, 50° C. 30 seconds and 72° C. 30 seconds followed by 10 minutes at 72° C. Bands are amplified with cDNA derived from anther, pollen, and microspore but not with cDNA derived from ear, glume/lemma/palea, husk, kernel, rachis, leaf, pollen, silk, or root.

For the isolation of the clone ID 700354681 promoter, SEQ ID NO:62 is used in combination with SEQ ID NO:1 (AP1) in a standard GenomeWalker™ PCR reaction using Expand Hi Fidelity DNA Polymerase (BMB, Indianapolis, Ind.) in conjunction with the supplied buffer #2. Each reaction contains 2 μL of a 1:2 dilution of the GenomeWalker™ libraries made according to the manufacturer's protocol (Clontech, Palo Alto, Calif.). The following cycling parameters are used: 94° C. 1 minute, 7 cycles of 94° C. 2 seconds, 72° C. 3 min, and 36 cycles 94° C. 2 seconds, 66° C. 3 minutes followed by a 4-minute incubation at 66° C. For the nested, secondary PCR reaction, 1 μL of a 1:50 dilution of the primary reaction is used with SEQ ID NO:63 and SEQ ID NO:2 (AP2) in a standard GenomeWalker™ PCR reaction using Expand Hi Fidelity DNA Polymerase (BMB, Indianapolis, Ind.) with the supplied buffer #2. The reactions are carried out under the following cycling conditions: 94° C. 1 minute, 5 cycles of 94° C. 2 seconds, 72° C. 3 minutes, and 25 cycles of 94° C. 2 seconds and 67° C. 3 minutes followed by 4 minutes at 67° C.

Twenty five microliters of the secondary PCR reaction is analyzed by agarose gel electrophoresis. The bands are isolated, purified using the Qiaquick gel extraction kit (Qiagen, Valencia, Calif.) and eluted with 30 μL ddH2O. Five microliters of the purified band is ligated to 50 ng of pGEM-T-Easy vector (Promega, Madison, Wis.). DNA from individual clones is isolated using the Qiagen Plasmid Mini kit (Qiagen, Valencia, Calif.) and sequenced using the M13 forward primers and M13 reverse primers.

To add a HindIII restriction site to the 5' end and Bgl II, BamH1 sites at the 3' end of the 700354681 promoter fragment, 1 μL of the clone harboring the promoter sequence is amplified under standard GenomeWalker™ PCR conditions using Expand Hi Fidelity DNA Polymerase (BMB, Indianapolis, Ind.) with the supplied buffer #2 in combination with primers SEQ ID NO:64 and SEQ ID NO:3 (AP3).

The reactions are carried out under the following cycling conditions: 94° C. 1 minute, 3 cycles of 94° C. 2 seconds, 70° C. 3 minutes and 12 cycles of 94° C. 2 seconds 67° C. 3 minutes followed by a 4-minute incubation at 67° C. A 25 µL aliquot of this PCR reaction is analyzed by agarose gel electrophoresis. The bands are isolated, purified using the Qiaquick gel extraction kit (Qiagen, Valencia, Calif.), and eluted with 30 µL ddH2O. Five microliters of the purified band is ligated to 50 ng of pGEM-T-Easy vector (Promega, Madison, Wis.). DNA from individual clones is isolated using the Qiagen Plasmid Mini kit (Qiagen, Valencia, Calif.). SEQ ID NO:90 is the promoter sequence for clone ID 700354681 Sequence analysis shows SEQ ID NO:90 to be a fragment of SEQ ID NO: 87.

The promoter band is purified using the Qiaquick gel extraction kit (Qiagen, Valencia, Calif.), and eluted with 30 µL ddH$_2$O. An aliquot of the purified band is ligated to an expression vector as shown in FIG. 1 (pMON19469) that is prepared for example by digesting 10 µg with BglII and HindIII, separating by agarose gel electrophoresis and isolating the vector band using the Qiaquick gel extraction kit (Qiagen, Valencia, Calif.), and eluted with 30 PL 10 mM Tris pH 8.5.

3l. 700353007 Clone Analysis and Promoter Isolation

To determine the distribution of the clone ID 700353007 transcripts in corn, RT-PCR is performed using the SEQ ID NO:65 and SEQ ID NO:66 primers following a standard RT-PCR protocol using cDNA derived from anther, 6 cm ear, glume/lemma/palea, husk, kernel from 4 cm ears, leaf, meristem, mature anther/pollen, microspores, rachis, root, and silk. Taq DNA polymerase from BMB (Indianapolis, Ind.) is used in combination with the supplied reaction buffer. Cycling parameters are as follows: 95° C. for 1 minute and 35 cycles of 95° C. 15 seconds, 50° C. 30 seconds and 72° C. 30 seconds followed by 10 minutes at 72° C. Bands are amplified with cDNA derived from anther, glume/lemma/palea, pollen, and microspore but not with cDNA derived from ear, husk, kernel, rachis, leaf, silk, or root.

For the isolation of the clone ID 700353007 promoter, SEQ ID NO:67 is used in combination with SEQ ID NO:1 AP1 in a standard Genome Walker PCR reaction using Expand Hi Fidelity DNA Polymerase (BMB, Indianapolis, Ind.) in conjunction with the supplied buffer #2. Each reaction contains 2 µL of a 1:2 dilution of the GenomeWalker™ libraries made according to the manufacturer's protocol (Clontech, Palo Alto, Calif.). The following cycling parameters are used: 94° C. 1 minute, 7 cycles of 94° C. 2 seconds, 72° C. 3 min, and 36 cycles 94° C. 2 seconds, 66° C. 3 minutes followed by 4 minute incubation at 66° C. For the nested, secondary PCR reaction, 1 µL of a 1:50 dilution of the primary reaction was used with SEQ ID NO:68 and SEQ ID NO:2 (AP2) in a standard GenomeWalker™PCR reaction using Expand Hi Fidelity DNA Polymerase (BMB, Indianapolis, Ind.) with the supplied buffer #2. The reactions are carried out under the following cycling conditions: 94° C. for 1 minute, 5 cycles of 94° C. 2 seconds, 72° C. 3 minutes, and 25 cycles of 94° C. 2 seconds and 67° C. 3 minutes followed by 4 minutes at 67° C.

Twenty five microliters of the secondary PCR reaction is analyzed by agarose gel electrophoresis. The bands are isolated, purified using the Qiaquick gel extraction kit (Qiagen, Valencia, Calif.) and eluted with 30 µl ddH2O. Five microliters of the purified band is ligated to 50 ng of pGEM-T-Easy vector (Promega, Madison, Wis.). DNA from individual clones is isolated using the Qiagen Plasmid Mini kit (Qiagen, Valencia, Calif.), and sequenced using the M13 forward primers and M13 reverse primers.

To add a HindIII restriction site to the 5' end and BglII, BamH1 sites at the 3' end of the 700353007 promoter fragment, 1 µL of the isolated DNA is amplified under standard Genome Walker™ PCR conditions using Expand Hi Fidelity DNA Polymerase (BMB, Indianapolis, Ind.) with the supplied buffer #2 in combination with primers SEQ ID NO:69 and SEQ ID NO:3 (AP3). The reactions are carried out under the following cycling conditions: 94° C. 1 minute, 3 cycles of 94° C. 2 seconds, 70° C. 3 minutes and 12 cycles 94° C. 2 seconds 67° C. 3 minutes followed by 4-minute incubation at 67° C. A 25 µL aliquot of this PCR reaction is analyzed by agarose gel electrophoresis. The bands are isolated, purified using the Qiaquick gel extraction kit (Qiagen, Valencia, Calif.), eluted and ligated to pGEM-T-Easy vector (Promega, Madison, Wis.). DNA from individual clones is isolated using the Qiagen Plasmid Mini kit (Qiagen, Valencia, Calif.). The sequence of the promoter fragment is SEQ ID NO:91.

The promoter fragment is cloned into a vector such as shown in FIG. 1 (pMON19469) containing the hsp70 intron/GUS cassette.

3m. 700352625 Clone Analysis and Promoter Isolation

To determine the distribution of the clone ID 700352625 transcripts in corn, RT-PCR is performed using the SEQ ID NO:70 and SEQ ID NO:71 primers following a standard RT-PCR protocol using cDNA derived from anther, 6 cm ear, glume/lemma/palea, husk, kernel from 4 cm ears, leaf, meristem, mature anther/pollen, microspores, rachis, root, and silk. Taq DNA polymerase from BMB (Indianapolis, Ind.) is used in combination with the supplied reaction buffer. Cycling parameters are as follows: 95° C. for 1 minute and 35 cycles of 95° C. 15 seconds, 50° C. 30 seconds and 72° C. 30 seconds followed by 10 minutes at 72° C. Bands are amplified with cDNA derived from anther, glume/lemma/palea, pollen, and microspore but not with cDNA derived from ear, husk, kernel, rachis, leaf, silk, or root.

For the isolation of the clone ID 700352625 promoter, SEQ ID NO:72 is used in combination with SEQ ID NO:1 (AP1) in a standard GenomeWalker™ PCR reaction using Expand Hi Fidelity DNA Polymerase (BMB, Indianapolis, Ind.) in conjunction with the supplied buffer #2. Each reaction contains 2 µL of a 1:2 dilution of the GenomeWalker™ libraries made according to the manufacturer's protocol (Clontech, Palo Alto, Calif.). The following cycling parameters are used: 94° C. 1 minute, 7 cycles of 94° C. 2 seconds, 72° C. 3 min, and 36 cycles 94° C. 2 seconds, 66° C. 3 minutes followed by 4 minute incubation at 66° C. For the nested, secondary PCR reaction, 1 µL of a 1:50 dilution of the primary reaction was used with SEQ ID NO:73 and SEQ ID NO. 2 (AP2) in a standard GenomeWalker™ PCR reaction using Expand Hi Fidelity DNA Polymerase (BMB, Indianapolis, Ind.) with the supplied buffer #2. The reactions are carried out under the following cycling conditions: 94° C. 1 minute, 5 cycles of 94° C. 2 seconds, 72° C. 3 minutes, and 25 cycles of 94° C. 2 seconds and 67° C. 3 minutes followed by 4 minutes at 67° C.

Twenty five microliters of the secondary PCR reaction is analyzed by agarose gel electrophoresis. The bands are isolated, purified using the Qiaquick gel extraction kit (Qiagen, Valencia, Calif.) and eluted with 30 µL ddH2O. Five microliters of the purified band is ligated to 50 ng of pGEM-T-Easy vector (Promega, Madison, Wis.). DNA from individual clones is isolated using the Qiagen Plasmid Mini kit (Qiagen, Valencia, Calif.), and sequenced using the M13 forward primers and M13 reverse primers.

To add a HindIII restriction site to the 5' end and a BamH1 site at the 3' end of the 700352625 promoter fragment, 1 μL of the isolated DNA was amplified under standard Genome Walker™ PCR conditions using Expand Hi Fidelity DNA Polymerase (BMB, Indianapolis, Ind.) with the supplied buffer #2 in combination with primers SEQ ID NO:74 and SEQ ID NO:3 (AP3). The reactions are carried out under the following cycling conditions: 94° C. 1 minute, 3 cycles of 94° C. 2 seconds, 70° C. 3 minutes and 12 cycles 94° C. 2 seconds 67° C. 3 minutes followed by 4-minute incubation at 67° C. Twenty five microliters of this PCR reaction is analyzed by agarose gel electrophoresis. The bands are isolated, purified and ligated to pGEM-T-Easy vector DNA (Promega, Madison, Wis.). DNA from individual clones is isolated using the Qiagen Plasmid Mini kit (Qiagen, Valencia, Calif.). The promoter sequence is shown in SEQ ID NO:92. The promoter fragment is cloned in an expression vector as shown in FIG. 1 (pMON19469).

3n. 700382630 Clone Analysis and Promoter Isolation

To determine the distribution of the clone ID 700382630 transcripts in corn, RT-PCR is performed using the SEQ ID NO:75 and SEQ ID NO:76 primers following a standard RT-PCR protocol using cDNA derived from anther, 6 cm ear, glume/lemma/palea, husk, kernel from 4 cm ears, leaf, meristem, mature anther/pollen, microspores, rachis, root, and silk. Taq DNA polymerase from BMB (Indianapolis, Ind.) is used in combination with the supplied reaction buffer. Cycling parameters are as follows: 95° C. for 1 minute and 35 cycles of 95° C. 15 seconds, 50° C. 30 seconds and 72° C. 30 seconds followed by 10 minutes at 72° C. Bands are amplified with cDNA derived from anther, glume/lemma/palea, pollen, and microspore but not with cDNA derived from ear, husk, kernel, rachis, leaf, silk, or root.

For the isolation of the clone ID 700382630 promoter, SEQ ID NO:77 is used in combination with SEQ ID NO:1 (AP1) in a standard GenomeWalker™ PCR reaction using Expand Hi Fidelity DNA Polymerase (BMB, Indianapolis, Ind.) in conjunction with the supplied buffer #2. Each reaction contains 2 μL of a 1:2 dilution of the GenomeWalker™ libraries made according to the manufacturer's protocol (Clontech, Palo Alto, Calif.). The following cycling parameters are used: 94° C. 1 minute, 7 cycles of 94° C. 2 seconds, 72° C. 3 min, and 36 cycles 94° C. 2 seconds, 66° C. 3 minutes followed by 4 minute incubation at 66° C. For the nested, secondary PCR reaction, 1 μL of a 1:50 dilution of the primary reaction is used with SEQ ID NO:78 and SEQ ID NO:3 (AP3) in a standard GenomeWalker™ PCR reaction using Expand Hi Fidelity DNA Polymerase (BMB, Indianapolis, Ind.) with the supplied buffer #2. The reactions are carried out under the following cycling conditions: 94° C. 1 minute, 5 cycles of 94° C. 2 seconds, 72° C. 3 minutes, and 25 cycles of 94° C. 2 seconds and 67° C. 3 minutes followed by 4 minutes at 67° C.

Twenty five microliters of the secondary PCR reaction is analyzed by agarose gel electrophoresis. The bands are isolated, purified, and ligated to pGEM-T-Easy vector (Promega, Madison, Wis.) DNA. DNA from individual clones is isolated using the Qiagen Plasmid Mini kit (Qiagen, Valencia, Calif.), and sequenced using the M13 forward primers and M13 reverse primers. The promoter sequence is shown in SEQ ID NO:93.

Example 4

Promoter Isolation and Cloning

The DNA fragments resulting from the nested PCR amplification described above are isolated and gel purified. A 25 μL aliquot of the secondary PCR is run on an agarose gel. The DNA fragment of the secondary PCR product is purified from the agarose gel using the Qiagen Kit following the conditions suggested by the manufacturer. The purified DNA is ligated to pGEM-T Easy vector (pGEM-T Easy Vector System I, Promega Corp., Madison, Wis.) following the conditions recommended by the manufacturer. An aliquot of the ligation reaction is transformed into a suitable *E. coli* host such as DH10B and the cells plated on selection medium (for DH10B, 100 g/mL carbenicillin). Bacterial transformants are selected, grown in liquid culture, and the plasmid DNA isolated using a commercially available kit such as the Qiaprep Spin Microprep Kit (Qiagen Corp., Valencia, Calif.). Purified plasmid containing the predicted insert size based on restriction enzyme analysis are sequenced using the dye terminator method in both directions using the M13 forward and reverse primers shown in SEQ ID NO:4 (M13 forward primer) and SEQ ID NO:5 (M13 reverse primer). Restriction enzymes are available from a number of manufacturers (see, for example, Boehringer Mannheim (Indianapolis, Ind.). The 5' flanking regions containing the promoter sequences are determined and shown in SEQ ID NOS:79-98. Engineering restriction sites for cloning into suitable vectors is done using standard molecular biology techniques known to those skilled in the art.

Example 5

Transient Analysis of Promoter Activity in Protoplasts and Microspores

For transient expression, promoter fragments are cloned into expression vectors such as pMON19469 shown in FIG. 1. Plasmid pMON19469 is an expression vector consisting of the following genetic components: P-e35S is the promoter for the 35S RNA from CaMV containing a duplication of the −90 to −300 region; HSP70 intron is the intervening sequence of the maize heat shock protein as described in U.S. Pat. Nos. 5,593,874 (herein incorporated by reference in its entirety) and 5,859,347 (herein incorporated by reference in its entirety); GUS: 1 is the coding region for beta-glucuronidase; nos 3' is the termination signal from the nopaline synthase gene; ori-M13 and ori-pUC are origins of replication; AMP is the coding region for ampicillin selection. If a translational start codon of a target promoter is identified, the fragment is cloned into pMON19469 in place of the P-e35S genetic element. If an AUG is not identified, the promoter fragment is cloned into an expression vector modified to enable translational fusions with a reporter gene such as β-glucuronidase (GUS) (Jefferson et al., EMBO J., 6:3901, 1987) or green fluorescent protein (GFP) as described in Pang et al. (Plant Physiol. 112:893, 1996).

The expression constructs are tested in a transient plant assay. A number of assays are available and known to those skilled in the art. Analysis of reporter genes in a protoplast system can be used to assess the activity of a regulatory element, such as a promoter operably linked to the reporter gene. A leaf protoplast isolation and electroporation protocol is followed essentially as described by Sheen (The Plant Cell 3:225-245, 1991) with the following modifications: the seed used is FR27RHM X FRMol7RHM from Illinois Foundation Seeds. The seed is surface sterilized for 2 minutes in 95% ethanol, rinsed twice with sterile water, 30 minutes in 50% bleach (Clorox) plus 2 drops of Tween-20, three rinses in sterile water followed by a 5-minute soak in benlate/captan solution to prevent fungal growth. The seeds are germinated in phytotrays containing 100 ml ½ MS media (2.2 g/L MS salts, 0.25% gelrite), 7 seeds per phytotray. The seeds are grown 5 days at 26° C. in 16/8 hour day/night photoperiod and 7 days in the dark at 28° C. The second leaf from each plant is sliced longitudinally using Feather No. 11 surgical blades. Digestion time is two hours and 10 minutes in the light at 26° C. After digestion, the plates are swirled two times at 80-100 rpm for 20 seconds each and the protoplast/enzyme solution is pipetted through a 190 μm tissue collector. Protoplasts are counted using a hemacytometer counting only protoplasts that are intact and circular. Ten to fifty micrograms of DNA containing the vector of interest is added per cuvette. Final protoplast densities at electroporation range from $3\times10^6$/mL to $4.5\times10^6$/mL. Electroporations are performed in the light using Bio-Rad Gene pulser cuvettes (Bio-Rad Hercules, Calif.) with a 0.4 cm gap and a maximum volume of 0.8 mL at 125 μFarads capacitance and 260 volts. The protoplasts are incubated on ice after resuspension in electroporation buffer and are kept on ice in cuvettes until 10 minutes after electroporation. The protoplasts are kept at room temperature for ten minutes before adding 7 mL of protoplast growth medium. The protoplast culture medium bas been described (Fromm et al., Methods in Enzymology 153, 351-366, 1987). Culture plates are layered with the growth medium and 1.5% Sea-Plaque agarose (FMC BioProducts, Rockland, Me.) to prevent protoplast loss. Samples are cultured in the light at 26° C., 16/8 day/night cycle, until harvested for the assay (typically 18-22 hours after electroporation). Samples are pipetted from the petri plates to 15 mL centrifuge tubes and harvested by centrifugation at 800-1000 rpm. The supernatant is removed and samples are assayed immediately for the gene of interest. Samples can also be frozen for later analysis.

For analysis of promoter activity in a wheat protoplast system, the method for isolation and preparation of wheat protoplasts is performed as described by Zhou et al. (Plant Cell Reports 12:612, 1993). The electroporation buffer used has been described (Li et al., 1995). The culture medium used is MS 1 MSM (4.4 g Gibco MS salts/L, 1.25 ml Thiamine HCL (0.4 mg/mL), 1 mL 2,4-D (1 mg/mL), 20 g/L sucrose, 0.15 mL asparagine (15 mg/mL), 0.75 g $MgCl_2$. 109 g/L 0.6M mannitol, pH5.5. Mustang protoplasts are used for protoplast isolation about four days after subculture. Briefly, 8 g of wheat cell suspension is poured into a culture tube, the cells are allowed to settle. The medium is removed and remaining cells are resuspended with 40 mL enzyme solution, transferred to a petri plate, wrapped in foil, and incubated at 26° C. for 2 hours on a rotator at 40 rpm. The suspension is centrifuged at 200 g for 8 min., washed twice with centrifugation between each wash, resuspended in 10 mL wash solution and stored on ice. The number of protoplasts is determined and the volume adjusted to a final concentration of $4\times10^6$ protoplasts/ml. About 0.75 mL of protoplasts is added to each electroporation cuvette and up to about 50 μg plasmid DNA of the vector in 50 μL solution is added to the protoplasts. The electroporation conditions are 960 μFarads and 160 volts using a Bio-Rad Gene Pulser (Bio-Rad Laboratories, Hercules, Calif.). The samples remain on ice for 10 minutes prior to and during electroporation. After electroporation, the samples are left on ice for about 10 minutes and removed and allowed to warm to room temperature for 10 minutes. The electroporated cells are pipetted into MS1 WSM medium and incubated in the dark for 18-22 hours at 24° C. The cells are harvested by centrifugation at 200-250 g for 8 minutes and frozen on dry ice for subsequent analysis of expression of the gene of interest.

In another transient assay system, barley microspores are used. For this assay shoots are collected and spikes are removed from the sheath and placed in 15×100 mm plates. Fifteen microliters of 0.3 M ice cold mannitol is added into each plate containing 10 spikes. The plates are sealed with parafilm and kept at 4° C. for 3-4 days. Pre-treated spikes are cut about 1-2 cm into a chilled blender cup (about 10 two-rowed spikes needed/plate). The spikes are covered with enough cold mannitol to create a slurry and blended at low speed in a Waring blender for 6-seconds. The slurry is filtered through cheesecloth or a nylon membrane and the filtrate is filtered through a 100μ mesh nylon membrane into a 50 mL centrifuge tube. The mixture is spun for 5 minutes at 900 rpm and the liquid is decanted and microspore pellet resuspended in 2 mL liquid FHG medium. The microspores are filtered through three layers of Whatman #2 filter paper into a filtering flask under vacuum. About 2 mL microspores are dropped on each filter set and the uppermost filter paper is transferred to solid medium (FHG+0.25 M mannitol+0.25 M sorbitol on a 15×100 mm plate). The plates are sealed with parafilm and incubated in the dark at 25° C. for 3-4 hours prior to particle bombardment. A number of methods of particle bombardment can be used (see, for example, Klein et al., Bio/Technology 6:559, 1988; Christou, Particle Bombardment for Genetic Engineering of Plants, Academic Press, 1996). After bombardment, the plates are sealed and kept at 25° C. for 20-24 hours. 0.3 M mannitol solution is used to wash microspores from the filter paper and the microspores are collected by centrifugation and analyzed for expression of the gene of interest. The FHG medium recipe is as follows: Macroelements (mg/L) include, 1900 mg KNO, 165 mg $NH_4NO_3$, 170 mg $KH_2PO_4$, 370 mg $MgSO_4$ 7 $H_2O$, 440 mg $CaCl_2$ $2H_2O$; Microelements (mg/L) include 40 mg FeNa.EDTA, 22.3 mg $MnSO_4.5H_2O$, 6.2 mg $H_3BO_3$, 8.6 mg $ZnSO_4$, 0.025 $CuSO_4.5H_2O$, 0.25 mg $NaMOO_4.2H_2O$.

Example 6

Transient Analysis of Promoter Activity in Wheat Reproductive Tissues

For analysis of promoter activity in wheat reproductive tissues such as wheat anthers and ovaries, constructs containing the potential promoter, the HSP70 intron and the GUS gene are bombarded into wheat anthers and ovaries from wheat spikes in which the boot is just beginning to open. One spike of anthers and ovaries is dissected per plate (1 liter plate medium containing 4.4 g MS salt, 40 g maltose, 40 g raffinose, 22.78 g mannitol, 1.95 g MES and 4 g phytagel at pH 5.8). Two and a half micrograms of each DNA sample (1 μg/μL) to be tested is precipitated with 12.5 μL tungsten, 5.0 μL 0.1M spermidine and 12.5 μL 1.0M calcium chloride for 40 minutes at room temperature. For gunpowder bombardments, 12.5 μL of the supernatant is removed and remainder of the sample is sonicated before each shot. Two and a half microliters of the DNA precipitant is bombarded per shot. For the helium gun bombardments, the precipitated DNA is spun down, washed with 70% EtOH and with 100% EtOH and resuspended in 40 μL 100% EtOH. Five microliters of the DNA is bombarded per plate.

For either method, each plate is shot twice, and two plates are assayed per DNA sample. After bombardment, the plates are incubated overnight at 24° C. in the dark. The next day the anther and ovaries are transferred to a GUS staining solution. To increase the penetration of the staining solution, the samples are put in a vacuum chamber for 10 minutes. Anthers and ovaries are incubated in the staining solution at 37° C. for 16-24 hours. The staining solution is replaced with 70% Ethanol, and the tissues are stored at 4° C. Staining is strictly qualitative, either there is expression or not. The staining indicates nothing of the tissue specificity of the potential promoters in stable plates, because the wheat ovary is a very promiscuous tissue that allows many active promoters to be expressed in this transient system.

Example 7

Promoter Activity from Transient Assay Analysis

In general, transcriptional regulatory elements necessary for promoter activity are located within a few hundred bases of the transcriptional start site. In many plant promoters, regulatory elements sufficient for driving heterologous gene expression in a spatial and temporal pattern that mimics the expression of the endogenous gene are located within 1000 base pairs 5' of the transcriptional start site. There are some genes, however, where transcriptional regulatory elements can be located kilobases away, 5' or 3' to the transcriptional start site.

The transient assay is a system well suited to determining if sufficient regulatory elements are present for transcription initiation. As described herein, a DNA fragment is operationally linked to a reporter gene of interest and that construct is "placed" (through particle bombardments, electroporation, etc) into cells, protoplasts or tissues. Expression of the reporter gene in the recipient cells indicates that enough regulatory sequences reside in the DNA fragment to initiate transcription. Thereby, the DNA fragment can be considered a promoter. The transient assay does not provide any data regarding the pattern of gene expression the promoter fragment would provide in vivo. A prediction of the promoter's activity can be made based on the pattern of the endogenous gene's activity, but the accuracy of this prediction is dependent on whether the promoter fragment contains all the necessary regulatory elements responsible for the proper expression of the endogenous gene.

A negative result in a transient assay does not necessarily indicate that a tested DNA fragment has no promoter activity. In addition to experimental error, some of the conditions which could result in a negative result are: 1). A translational start codon is located within the DNA fragment thereby blocking expression of the reporter gene; 2). The DNA fragment contains a transcriptional start site and a splice donor site, but lacks a splice acceptor site. Therefore, the reporter gene is not expressed because the message is not properly spliced; 3). Transcription factors specific to the function of the promoter region may not be present in the tissues used for the transient assay; or 4). The level of transcription is below the limits of detection of the assay.

To test the DNA fragments contained in Example 3 for promoter activity, SEQ ID NOS: 82, 83, 84, 85, 86, 87, 88, 89, 90, 91, 92, 93, 94, 95, 96, 97 and 98 are assayed by particle bombardment of barley microspores (see Example 5) or particle bombardment of wheat reproductive tissues (see Example 6). As described herein, the experimental cassette used to test each putative promoter fragment contains the fragment operationally linked to the hsp70 intron and the GUS gene. The experiment for each construct is carried out at least 2 times. A construct containing the e35S promoter operationally linked to the hsp70 intron and GUS gene is used as a positive control and a no-DNA bombardment is used as a negative control. The data are summarized in Table 2.

TABLE 2

Summary of transient assay data testing for promoter activity of the DNA fragments containing SEQ ID NOS: 82–98. In the first column are the Clone IDs of the EST sequences used to isolate the promoter fragments (see Example 3). The second column are the SEQ ID numbers of the fragments tested in the transient assay. The construct names are listed in the third column. Each construct contains a fragment operably linked to the hsp70 intron and GUS gene. The Fourth column indicates the transient assay used. The fifth column is the level of GUS activity detected based on a qualitative evaluation of the number and intensity of positively staining cells in the assay. Low indicates much lower than 35S, medium indicates slightly lower than 35S, and high indicates greater than or equal to 35S.

| Clone ID | SEQ ID # | Construct | Transient Assay | Level Detected |
| --- | --- | --- | --- | --- |
| 700353038 | 96 | pMON48133 | wheat reproductive tissue | low |
| | 98 | pMON48132 | wheat reproductive tissue | low |
| | 95 | pMON48131 | wheat reproductive tissue | low |
| | 97 | pMON48130 | wheat reproductive tissue | low |
| 700352826 | 94 | pMON48136 | wheat reproductive tissue | medium |
| 700354918 | 82 | pMON48134 | wheat reproductive tissue | not detected |
| 700353844 | 83 | pMON48137 | wheat reproductive tissue | medium |
| 700355306 | 84 | pMON53312 | wheat reproductive tissue | not detected |
| 700353142 | 85 | pMON53306 | wheat reproductive tissue | low |
| 700282503 | 86 | pMON53320 | wheat reproductive tissue | not detected |
| 700282409 | 88 | pMON53310 | wheat reproductive tissue | high |
| 700282409 | 87 | pMON53308 | wheat reproductive tissue | medium |
| 700352616 | 89 | pMON49324 | wheat reproductive tissue | low |
| | 89 | pMON49323 | wheat reproductive tissue | not detected |
| | 89 | pMON49322 | wheat reproductive tissue | not detected |
| 700354681 | 90 | pMON49300 | wheat reproductive tissue | high |
| 700353007 | 91 | pMON49332 | wheat reproductive tissue | low |
| | 91 | pMON49327 | wheat reproductive tissue | not detected |
| | 91 | pMON49326 | wheat reproductive tissue | low |
| | 91 | pMON49325 | wheat reproductive tissue | low |
| 700352625 | 92 | pMON49337 | wheat reproductive tissue | low |
| | 92 | pMON49330 | wheat reproductive tissue | low |
| | 92 | pMON49329 | wheat reproductive tissue | not detected |
| | 92 | pMON49328 | wheat reproductive tissue | low |
| 700382630 | 93 | pMON49336 | barley microspore | low |

7a: 700353038

For clone ID 700353038, two promoter fragments are isolated that comprise SEQ ID NOS:80 and 81. Two potential translational start codons (ATG) are identified at the 3' end of each fragment. Therefore, two new fragments are generated from each fragment which has 3' ends just upstream of one of the ATG's (see Example 3A). These new promoter fragments comprise SEQ ID NOS:95 and 96 (derived from SEQ ID NO:81) and SEQ ID NOS:97 and 98 (derived from SEQ ID NO:80). Each DNA fragment comprising each of SEQ ID NOS: 95, 96, 97, and 98 is operably linked to the hsp70 intron and the GUS gene to generate constructs pMON48131, pMON48133, pMON48130 and pMON48132, respectively. These constructs are tested in the wheat reproductive tissue transient assay. GUS activity is detected for each construct. The level of expression detected is much lower than seen with e35S but greater than that seen with the no DNA bombardments. These data indicate that SEQ ID NOS:95, 96, 97, and 98 contain promoter activity and translation initiated within the GUS gene.

7b: 700352826

The fragment comprising SEQ ID NO:79 has an internal HindIII site at position 416. SEQ ID NO: 94 contains the sequences 417-2213 of SEQ ID NO:79 (all sequences 3' of the HindIII site, inclusive). The fragment comprising SEQ ID NO:94 is operably linked to the hsp70 intron and the GUS gene to generate the construct pMON48136. This construct is tested for promoter activity using the wheat reproductive tissue transient assay. GUS activity is detected at a level slightly below that seen with the e35S positive control indicating that SEQ ID NO:94 has promoter activity.

7c: 700354918

The fragment comprising SEQ ID NO:82 is operably linked to the hsp70 intron and the GUS gene to generate the construct pMON48134. This construct is tested for promoter activity using the wheat reproductive tissue transient assay. GUS activity is not detected which could be due to any of the reasons described above.

7d: 700353844

The fragment comprising SEQ ID NO:83 is operably linked to the hsp70 intron and the GUS gene to generate the construct pMON48137. This construct is tested for promoter activity using the wheat reproductive tissue transient assay. GUS activity is detected at a level slightly below that seen with the e35S positive control indicating that SEQ ID NO:83 has promoter activity.

7e: 700355306

The fragment comprising SEQ ID NO:84 is operably linked to the hsp70 intron and the GUS gene to generate the construct pMON53312. This construct is tested for promoter activity using the wheat reproductive tissue transient assay. GUS activity is not detected which could be due to any of the reasons described above.

7f: 700353142

The fragment comprising SEQ ID NO:85 is operably linked to the hsp70 intron and the GUS gene to generate the construct pMON53306. This construct is tested in the wheat reproductive tissue transient assay. GUS activity is detected at a level of expression much lower than seen with e35S but greater than that seen with the no DNA bombardments indicating that SEQ ID NO:85 has promoter activity.

7g: 700282503

The fragment comprising SEQ ID NO:86 is operably linked to the hsp70 intron and the GUS gene to generate the construct pMON53320. This construct is tested for promoter activity using the wheat reproductive tissue transient assay. GUS activity is not detected which could be due to any of the reasons described above.

7h: 700282409 Profilin 2 and 700354681

The fragment comprising SEQ ID NO:90 is a smaller version of the putative promoter comprising SEQ ID NO:87. The fragment comprising SEQ ID NO:90 is operably linked to the hsp70 intron and the GUS gene to generate the construct pMON449300. The fragment comprising SEQ ID NO:87 is operably linked to the hsp70 intron and the GUS gene to generate the construct pMON53308. Both constructs are tested in the wheat reproductive tissue transient assay. GUS activity is detected with each fragment tested. GUS activity is detected at a level slightly below that seen with the e35S positive control with SEQ ID NO:87. Gus activity is detected at a level equal to that seen with the e35S positive control with SEQ ID NO:90. These data indicate that both SEQ ID NOS:87 and 90 contain promoter activity.

7i: 700282409 Profilin 1

The fragment comprising SEQ ID NO:88 is operably linked to the hsp70 intron and the GUS gene to generate the construct pMON53310. This construct is tested in the wheat reproductive tissue transient assay. Gus activity is detected at a level equal to that seen with the e35S positive control indicating that SEQ ID NO:88 has promoter activity.

7j: 700352616

The translational start codon is not readily identifiable in the EST sequence for clone ID 7003542616. Therefore, the fragment comprising SEQ ID NO:89 is placed in vectors designed to generated GUS fusions (see Example 5). Three constructs are generated, pMON49322, pMON49323, and pMON49324 each representing a different reading frame for a putative translational fusion between the sequences in SEQ ID NO:89 and GUS. All three constructs are tested in the wheat reproductive tissue transient assay. GUS activity is detected with only one construct, at a level of expression much lower than seen with e35S but greater than that seen with the no DNA bombardments. These data indicate that a translational start codon is located within SEQ ID NO:89 and that SEQ ID NO:89 has promoter activity.

7k: 700353007

The translational start codon is not readily identifiable in the EST sequence for clone ID 700353007. Therefore, the fragment comprising SEQ NO: ID 92 is placed in vectors designed to generate GUS fusions (see Example 5). Three constructs are generated, pMON49325, pMON49326, and pMON49327, each representing a different reading frame for a putative translational fusion between the sequences in SEQ ID NO:91 and GUS. All three constructs are tested in the wheat reproductive tissue transient assay. GUS activity is detected with two constructs, at a level of expression much lower than seen with e35S but greater than that seen with the no DNA bombardments. This indicates that translation does initiate off the translational start codon located within the GUS gene. To test that, SEQ ID NO:91 is tested using the conventional vector described in Example 5, which has an inframe STOP codon upstream of the GUS translational start codon. With this construct, pMON 49332, GUS activity is detected at a level of expression much lower than seen with e35S but greater than that seen with the no DNA bombardments. These data indicate that SEQ ID NO:91 has promoter activity.

7l: 700352625

The translational start codon is not readily identifiable in the EST sequence for clone ID 700352625. Therefore, the fragment comprising SEQ ID NO:92 is placed in vectors designed to generate GUS fusions (see Example 5). Three constructs are generated, pMON49328, pMON49329, and pMON49330, each representing a different reading frame for a putative translational fusion between the sequences in SEQ ID NO:92 and GUS. All three constructs are tested in the wheat reproductive tissue transient assay. GUS activity is detected with two constructs, at a level of expression much lower than seen with e35S but greater than that seen with the no DNA bombardments. This indicates translation is initiating at the translational start codon within the GUS gene. To test that, SEQ ID NO:92 is tested using the conventional vector described in Example 5, which has an in frame STOP codon upstream of the GUS translational start codon. With this construct, pMON49337, GUS activity is detected at a level of expression much lower than seen with e35S but greater than that seen with the no DNA bombardments indicating that SEQ ID NO:92 has promoter activity.

7m: 700382630

The fragment comprising SEQ ID NO:93 is operably linked to the hsp70 intron and the GUS gene to generate the construct pMON49336. This is tested in the barley microspore transient assay. GUS activity is detected at a level of expression much lower than seen with e35S but greater than that seen with the no DNA bombardments indicating that SEQ ID NO:93 has promoter activity.

Example 8

Promoter Activity Analysis in Plants

Figure 2:
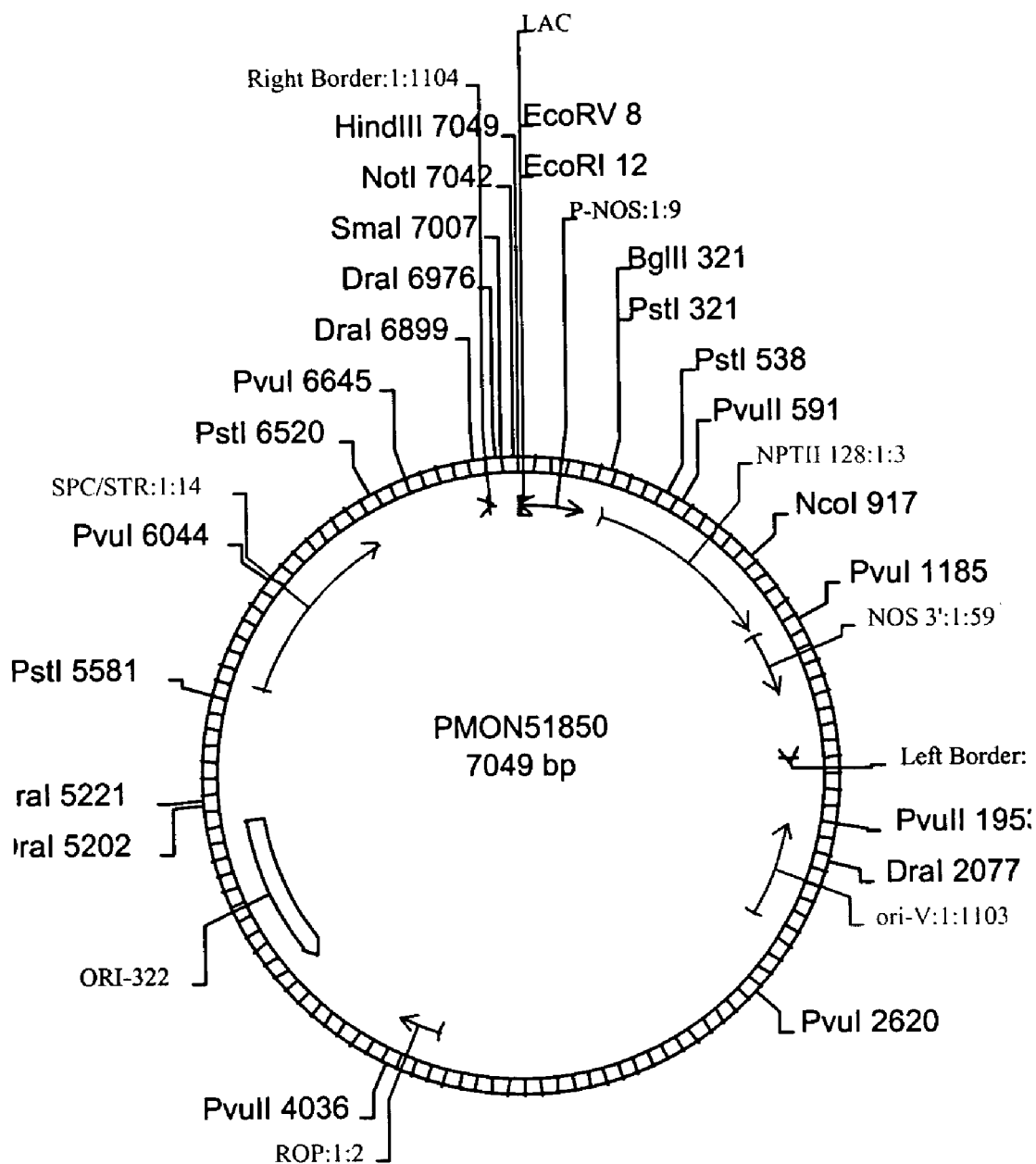
FIG. 2 is a plasmid map of pMON51850.

For stable plant transformation the 5' regulatory sequences are cloned into a plant transformation vector such as shown in FIG. 2. Plasmid pMON51850 is a double border (right and left T-DNA borders) plant transformation vector and contains the following genetic components: NOS 3' is the termination signal from the nopaline synthase gene; ori-322 and ori-V are origins of replication; kan is the coding region for kanomycin selection.

The promoter is operably linked to any gene of interest such as a glyphosate tolerance gene along with other regulatory sequences including, but not limited to, non-translated leaders and terminators as described above, and transformed into a target crop of interest via an appropriate delivery system such as Agrobacterium-mediated transformation (see, for example, U.S. Pat. No. 5,569,834, herein incorporated by reference in its entirety, U.S. Pat. No. 5,416,011, herein incorporated by reference in its entirety, U.S. Pat. No. 5,631,152, herein incorporated by reference in its entirety, U.S. Pat. No. 5,159,135, herein incorporated by reference in its entirety and U.S. Pat. No. 5,004,863, herein incorporated by reference in its entirety) or particle bombardment methods (see, for example, Patent Applns. WO 92/15675. WO 97/48814 and European Patent Appln. 586,355, and U.S. Pat. Nos. 5,120,657, 5,503,998, 5,830,728 and 5,015,580, all of which are herein incorporated by reference in their entirety). A large number of transformation and regeneration systems and methods are available and well-known to those skilled in the art. The stably transformed plants and progeny are subsequently analyzed for expression of the gene in tissues of interest by any number of molecular, immunodiagnostic, biochemical, and/or field evaluation methods known to those skilled in the art.

The results from the transient assay analysis described in Examples 7 are qualitative regarding the promoter activity of the DNA fragments tested. Although these promoters are predicted to be active in male reproductive tissues, the transient assay analysis does not demonstrate any support for this. To determine the promoter activity in male reproductive tissues, the promoter fragments are cloned upstream of a gene of interest (either GUS or the MS2 coat protein), placed in a plant transformation vector and transformed into plants. Tissues from R0 plants are harvested and assayed for the gene of interest.

Detection of GUS activity in male reproductive tissues is described in Example 5. For the detection of the MS2 coat protein, anther extracts are analyzed by immunodetection on Western Blots or ELISA analysis. For western blots, the T7 tag monoclonal and horse radish peroxidase conjugated antibody (Novagen, Madison, Wis.) is used to detect MS2 protein expression in anther tissues. Total protein is extracted (extraction buffer containing 1×PBS and 0.01% Tween-20) from anther, 10 μg of total protein sample is separated on a 10-20% polyacrylamide gradient gel (Bio-RAD, Hercules, Calif.) and transferred onto ECL nitrocellulose membrane (Amersham, Arlington, Ill.). A 1:5000 dilution of primary antisera is used to detect ACOX protein using the ECL detection system (Amersham, Arlington, Ill.). A 15 Kd protein is detected.

For ELISA quantification of MS2 coat protein levels in anthers, crude anther extracts containing 1 ug total protein is added to a 96-well Nunc-Immuno MaxiSorb plate coated with 100 μl of purified polyclonal anti-MS2 coat protein IgG antibody (0.1 ng/μL) in coating buffer (15 mM $Na_2CO_3$, 35 mM $NaHCO_3$, pH 9.6). The plate is sealed and incubated at 37° C. for one hour. The plate is then rinsed three times with washing buffer (1×PBS, 0.05% Tween 20, pH7.4). Fifty microliters of the anther extract containing 1 μg of total protein is added to a well, followed by addition of 50 μl of a 1:10,000 dilution of anti-T7 tag monoclonal and HSP conjugated antibody (Novagen). The loaded plate is incubated at 37° C. for one hour then rinsed three times with washing buffer. To develop the plate, 100 μl of substrate (a 1:1 mixture of $H_2O_2$ and TMB (3,3'-5,5'-tetra methyl benzidine), Kirgeggard and Perry, #50-76-03, Gaithersburg, Md.) is added to each well and the plate is incubated at room temperature for 3-5 min. One hundred microliters of stop solution (3M $H_3PO_4$) is added to terminate the reaction. The plate is read on a Spectra Max 340 (Molecular Devices, Sunnyvail, Calif.) at 450 nm.

Plasmids can be transformed into either monocot or dicot plants. The promoter fragments are derived from corn (Zea mays). Therefore, activity in a dicot plant would indicate a broad spectrum of plants in which the promoter is active. The dicot plant Arabidopsis thaliana offers several advantages as a model system to study promoter systems: ease of transformation, quick life cycle, and multiple stages of floral development on each plant. Monocot promoters that are active in Arabidopsis anthers are likely to be active in many monocot and dicot species. To test this, some promoters which are active in Arabidopsis are also tested in monocot plants. As shown below and summarized in Table 3, all promoter fragments tested that are active in Arabidopsis are also active in monocots.

TABLE 3

Summary of promoter activity in stably transformed plants. In the first column are the Clone IDs of the EST sequences used to isolate the promoter fragments (see Example 3). The second column shows the SEQ ID numbers of the fragments tested in the transient assay. The third column lists the introns used in the constructs. No introns are used in constructs for dicot transformation. The fourth column lists the reporter genes used in the constructs. The fifth column show the construct names. In the sixth column are the organisms transformed. The seventh column shows the type of assay used to detect the reporter gene. The eighth column shows the number of plants assayed. The ninth column shows the number of plants showing male expression and the last column describes any other tissues where the reporter protein is detected.

| Clone ID | SEQ ID | Intron | Gene Assayed | Construct | Organism | Assay Type | Number of Plants Assayed |
| --- | --- | --- | --- | --- | --- | --- | --- |
| 700353038 | 98 | none | GUS | pMON48183 | Arabidopsis | GUS activity | 4 |
|  | 98 | hsp70 intron | MS2 coat protein | pMON42438 | rice | Western | 5 |
| 700352826 | 94 | none | GUS | pMON48185 | Arabidopsis | GUS activity | 4 |
| 700353844 | 83 | none | GUS | 48186 | Arabidopsis | GUS activity | 1 |
|  | 83 | hsp70 intron | MS2 coat protein | 42439 | rice | Western | 3 |
| 700282409 | 88 | hsp70 intron | MS2 coat protein | 42938 | rice | Western | 5 |
|  | 88 | hsp70 intron | MS2 coat protein | 42938 | wheat | Elisa | 4 |
|  | 88 | hsp70 intron | MS2 coat protein | 42938 | wheat | Western | 4 |
|  | 88 | none | GUS | 48194 | Arabidopsis | GUS activity | 4 |
|  | 88 | hsp70 intron | MS2 coat protein | 52006 | wheat | Western | 6 |
|  | 88 | hsp70 intron | GUS | 53322 | wheat | GUS activity | 11 |
| 700354681 | 90 | hsp70 intron | MS2 coat protein | 42914 | rice | Western | 5 |
|  | 90 | hsp70 intron | MS2 coat protein | 42914 | wheat | Western | 19 |
|  | 90 | hsp70 intron | MS2 coat protein | 42936 | wheat | Elisa | 1 |
|  | 90 | hsp70 intron | MS2 coat protein | 42936 | wheat | Western | 3 |
|  | 90 | none | GUS | 51818 | Arabidopsis | GUS activity | 7 |
| 700353007 | 91 | hsp70 intron | MS2 coat protein | 52003 | wheat | Elisa | 2 |
|  | 91 | hsp70 intron | MS2 coat protein | 52003 | wheat | Western | 2 |
| 700352625 | 92 | hsp70 intron | MS2 coat protein | 52021 | wheat | Elisa | 1 |

8a. 700353038

To test for anther activity in dicot plants the fragment comprising SEQ ID NO: 98 is placed upstream of the GUS gene and put into a plant transformation vector resulting in the construct pMON48183. This construct is used to transform *Arabidopsis thaliana*. Two of four independent events show expression in the male reproductive tissues specifically. No GUS expression is detected in other floral tissues, stem or leaf. To test for anther activity in monocot plants, the fragment comprising SEQ ID NO:98 is placed upstream of the hsp70 intron/MS2 coat protein gene cassette and put into a plant transformation vector resulting in the construct pMON42438. This construct is used to transform *Oryza sativum* (rice). Anthers from five independent R0 rice plants are assayed by Western Blot for MS2 coat protein. All 5 plants are positive for MS2 coat protein. These data indicate that SEQ ID NO:98 can act as an anther enhanced promoter in both monocots and dicots.

8b. 700352826

To test for anther activity in dicot plants the fragment comprising SEQ ID NO:94 is placed upstream of the GUS gene and put into a plant transformation vector resulting in the construct pMON48185. This construct is used to transform *Arabidopsis thaliana*. Four of four independent events show expression in the male reproductive tissues. GUS expression is also detected in immature seed, seedlings and cut stems but not detected leaves, roots or other floral organs. These data indicate that SEQ ID NO:94 can act as an anther enhanced promoter in dicots. Because it is monocot-derived promoter, it is likely to be active in monocot anthers as well.

8c. 700353844

To test for anther activity in dicot plants the fragment comprising SEQ ID NO:83 is placed upstream of the GUS gene and put into a plant transformation vector resulting in the construct pMON48186. This construct is used to transform *Arabidopsis thaliana*. One event is obtained and it shows expression in the male reproductive tissues specifically. No GUS expression is detected in other floral tissues, leaves, or stems. To test for anther activity in monocots, the fragment comprising SEQ ID NO:83 is placed upstream of the hsp70 intron/MS2 coat protein gene cassette and put into a plant transformation vector resulting in the construct pMON42439. This construct is used to transform *Oryza sativum*. Anthers from three independent R0 rice plants are assayed by Western Blot for MS2 coat protein. Two of three plants are positive for MS2 coat protein. These data indicate that SEQ ID NO:83 can act as an anther enhanced promoter in both monocots and dicots.

8d: 700282409

To test for anther activity in dicot plants, the fragment comprising SEQ ID NO:88 is placed upstream of the GUS gene and put into a plant transformation vector resulting in the construct pMON48194. This construct is used to transform *Arabidopsis thaliana*. Two of four events show GUS expression in the anthers. One of four events has detectable GUS expression in roots but no other GUS expression is detected in other tissues.

To test for anther activity in monocot plants, the fragment comprising SEQ ID NO:88 is placed upstream of the hsp70 intron/MS2 coat protein gene cassette and put into a plant transformation vector resulting in the constructs pMON42938 and pMON52006. The construct pMON42938 is used to transform *Oryza sativum* (rice) and *Triticum aesitivum* (wheat). Anthers from five independent R0 rice plants are assayed by Western Blot for MS2 coat protein. Two of five plants are positive for MS2 coat protein. Anthers from four independent R0 wheat plants were assayed by ELISA for MS2 coat protein. Two of four plants are positive for MS2 coat protein. Anthers from four independent R0 wheat plants are assayed by Western Blot for MS2 coat protein but expression is below the limits of detection for each event. The construct pMON52006 is used to transform wheat. Anthers from six independent R0 wheat plants are assayed by Western Blot for MS2 coat protein. Three of six plants are positive for MS2 coat protein. These data indicate that SEQ ID NOS: 88 can act as an anther enhanced promoter in both monocots and dicots.

8e: 700354681

Because SEQ ID NO: 90 is a subfragment of SEQ ID NO: 87, only SEQ ID NO: 90 was tested. The fragment comprising SEQ ID NO:90 is placed upstream of the GUS gene and put into a plant transformation vector resulting in the construct pMON51818. This construct is used to transform *Arabidopsis thaliana*. Five of seven events show GUS expression in the anthers. GUS expression is not detected in other floral tissues.

The fragment comprising SEQ ID NO:90 is placed upstream of the hsp70 intron/MS2 coat protein gene cassette and put into a plant transformation vector resulting in the constructs pMON42914 and pMON42936. The construct pMON42914 is used to transform *Oryza sativum* (rice) and *Triticum aesitivum* (wheat). Anthers from five independent R0 rice plants are assayed by Western Blot for MS2 coat protein. Four of five plants are positive for MS2 coat protein. Anthers from nineteen independent R0 wheat plants are assayed by Western for MS2 coat protein. Fourteen of nineteen plants were positive for MS2 coat protein. The construct pMON42936 is used to transform wheat. Anthers from three independent R0 wheat plants are assayed by Western Blot for MS2 coat protein. One of three plants is positive for MS2 coat protein. These data indicate that SEQ ID NO: 90 can act as an anther enhanced promoter in both monocots and dicots. Because SEQ ID NO: 90 acts as an anther enhanced promoter, it is probable that SEQ ID NO: 87 also acts as an anther enhanced promoter.

8f. 700353007

To test for anther activity in monocot plants, the fragment comprising SEQ ID NO:91 is placed upstream of the hsp70 intron/MS2 coat protein gene cassette and put into a plant transformation vector resulting in the construct pMON52003. This construct is used to transform *Triticum aesitivum* (wheat). Anthers from two independent R0 wheat plants are assayed by Western Blot for MS2 coat protein. MS2 coat protein is not detected in either event. Anthers from two independent R0 wheat plants are assayed by ELISA for MS2 coat protein. MS2 coat protein is not detected in either event. At this time the data obtained have not been able to demonstrate if this particular construct containing SEQ ID NO:91 is active in anther in transgenic wheat as the number of the events evaluated is very low. Further evaluations are needed.

8g: 700352625

To test for anther activity in monocot plants, the fragment comprising SEQ ID NO:92 is placed upstream of the hsp70 intron/MS2 coat protein gene cassette and put into a plant transformation vector resulting in the construct pMON520021. This construct is used to transform *Triticum aesitivum* (wheat). Anthers from one R0 wheat plant is assayed by Western Blot for MS2 coat protein. MS2 coat protein is not detected. At this time the data obtained have not been able to demonstrate if this particular construct containing SEQ ID NO:92 is active in anther in transgenic wheat as the number of the events evaluated is very low. Further evaluations are needed.

Example 9

Identification of Cis Elements and Engineering Novel Promoters

Cis acting regulatory elements necessary for proper promoter regulation can be identified by a number of means. In one method, deletion analysis is carried out to remove regions of the promoter and the resulting promoter fragments are assayed for promoter activity. DNA fragments are considered necessary for promoter regulation if the activity of the truncated promoter is altered compared to the original promoter fragment. Through this deletion analysis, small regions of DNA can be identified which are necessary for positive or negative regulation of transcription. Promoter sequence motifs can also be identified and novel promoters engineered to contain these cis elements for modulating expression of operably linked transcribable sequences. See for example U.S. Pat. No. 5,223,419, herein incorporated by reference in its entirety, U.S. Pat. No. 4,990,607, herein incorporated by reference in its entirety, and U.S. Pat. No. 5,097,025, herein incorporated by reference in its entirety.

An alternative approach is to look for similar sequences between promoters with similar expression profiles. Promoters with overlapping patterns of activity can have common regulatory mechanisms. Several computer programs can be used to identify conserved, sequence motifs between promoters, including, but not limited to, MEME, SIGNAL SCAN, or GENE SCAN. These motifs can represent binding sites for transcription factors which act to regulate the promoters. Once the sequence motifs are identified, their function can be assayed. For example, the motif sequences can be deleted from the promoter to determine if the motif is necessary for proper promoter function. Alternatively, the motif can be added to a minimal promoter to test whether it is sufficient to activate transcription. Suspected negative regulatory elements can be tested for sufficiency by adding to an active promoter and testing for a reduction in promoter activity. Some cis acting regulatory elements may require other elements to function. Therefore, multiple elements can be tested in various combinations by any number of methods known to those skilled in the art.

Once functional promoter elements have been identified, promoter elements can be modified at the nucleotide level to affect protein binding. The modifications can cause either higher or lower affinity binding which would affect the level of transcription from that promoter.

Promoter elements can act additively or synergistically to affect promoter activity. In this regard, promoter elements from different 5' regulatory regions can be placed in tandem to obtain a promoter with a different spectrum of activity or different expression profile. Accordingly, combinations of promoter elements from heterologous sources or duplication of similar elements or the same element can confer a higher level of expression of operably linked transcribable sequences. For example, a promoter element can be multimerized to increase levels of expression specifically in the pattern affected by that promoter element.

The technical methods needed for constructing expression vectors containing the novel engineered 5' regulatory elements are known to those of skill in the art. The engineered promoters are tested in expression vectors and tested transiently by operably linking the novel promoters to a suitable reporter gene such as GUS and testing in a transient plant assay. The novel promoters are operably linked to one or more genes of interest and incorporated into a plant transformation vector along with one or more additional regulatory elements and transformed into a target plant of interest by a suitable DNA delivery system. The stably transformed plants and subsequent progeny are evaluated by any number of molecular, immunodiagnostic, biochemical, phenotypic, or field methods suitable for assessing the desired agronomic characteristic(s).

The invention claimed is:

1. An isolated nucleic acid comprising the sequence of SEQ ID NO:90, or a fragment thereof that regulates transcription of an operably linked DNA sequence.

2. A promoter comprising the nucleic acid sequence of SEQ ID NO:90.

3. The promoter of claim 2 wherein said promoter confers enhanced expression of operably linked genes in male reproductive tissues.

4. The promoter of claim 3 wherein said promoter confers enhanced expression of operably linked genes in anthers.

5. The promoter of claim 4 wherein said promoter confers enhanced expression of operably linked genes in wheat anthers.

6. A cell comprising a DNA construct comprising the isolated nucleic acid sequence of claim 1 operably linked to a transcribable DNA sequence and a 3' non-translated region.

7. A transgenic plant comprising a DNA construct comprising the isolated nucleic acid sequence of claim 1 operably linked to a transcribable DNA sequence and a 3' non-translated region.

8. A method of regulating transcription of a DNA sequence comprising operably linking the DNA sequence to the isolated nucleic acid sequence of claim 1.

9. A method of making a transgenic plant comprising introducing into a cell of a plant a DNA construct comprising the isolated nucleic acid sequence of claim 1 operably linked to a transcribable DNA sequence and a 3' non-translated region.

* * * * *